United States Patent
Brock et al.

(10) Patent No.: US 7,371,210 B2
(45) Date of Patent: *May 13, 2008

(54) FLEXIBLE INSTRUMENT

(75) Inventors: David L. Brock, Natick, MA (US);
Woojin Lee, Hopkinton, MA (US);
Gary Rogers, Wenham, MA (US);
Barry Weitzner, Acton, MA (US)

(73) Assignee: Hansen Medical, Inc., Mountain View, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 10/012,586

(22) Filed: Nov. 16, 2001

(65) Prior Publication Data

US 2002/0087049 A1 Jul. 4, 2002

Related U.S. Application Data

(60) Continuation-in-part of application No. 09/827,503, filed on Apr. 6, 2001, now Pat. No. 6,432,112, which is a continuation of application No. 09/746,853, filed on Dec. 21, 2000, now Pat. No. 6,692,485, which is a division of application No. 09/375,666, filed on Aug. 17, 1999, now Pat. No. 6,197,017, which is a continuation of application No. 09/028,550, filed on Feb. 24, 1998, now abandoned, application No. 10/012,586, which is a continuation-in-part of application No. 09/783,637, filed on Feb. 14, 2001, now abandoned, which is a continuation of application No. PCT/US00/12553, filed on May 9, 2000, application No. 10/012,586, which is a continuation-in-part of application No. PCT/US01/11376, filed on Apr. 6, 2001, and a continuation-in-part of application No. 09/746,853, and a continuation-in-part of application No. 08/927,503, which is a continuation-in-part of application No. PCT/US00/12553, filed on May 9, 2000.

(60) Provisional application No. 60/313,496, filed on Aug. 21, 2001, provisional application No. 60/313,497, filed on Aug. 21, 2001, provisional application No. 60/313,495, filed on Aug. 21, 2001, provisional application No. 60/293,346, filed on May 24, 2001, provisional application No. 60/279,087, filed on Mar. 27, 2001, provisional application No. 60/276,151, filed on Mar. 15, 2001, provisional application No. 60/276,217, filed on Mar. 15, 2001, provisional application No. 60/276,086, filed on Mar. 15, 2001, provisional application No. 60/276,152, filed on Mar. 15, 2001, provisional application No. 60/269,200, filed on Feb. 15, 2001, provisional application No. 60/269,203, filed on Feb. 15, 2001, provisional application No. 60/257,868, filed on Dec. 21, 2000, provisional application No. 60/257,816, filed on Dec. 21, 2000, provisional application No. 60/257,867, filed on Dec. 21, 2000, provisional application No. 60/257,869, filed on Dec. 21, 2000, provisional application No. 60/195,264, filed on Apr. 7, 2000, provisional application No. 60/133,407, filed on May 10, 1999.

(51) Int. Cl.
*A61B 1/00* (2006.01)
*A61B 19/00* (2006.01)

(52) U.S. Cl. .................. 600/114; 600/146; 606/130

(58) Field of Classification Search ................ 600/114, 600/101, 109, 104, 146, 139, 117, 118; 606/1, 606/130, 159, 180; 604/95, 159; 128/898
See application file for complete search history.

(56) References Cited

U.S. PATENT DOCUMENTS

| | | |
|---|---|---|
| 3,414,137 A | 12/1968 | Fortin |
| 4,604,016 A | 8/1986 | Joyce |
| 4,654,024 A | 3/1987 | Crittenden et al. |
| 4,750,475 A * | 6/1988 | Yoshihashi .................. 600/153 |
| 4,853,874 A | 8/1989 | Iwamoto et al. |
| 4,941,454 A | 7/1990 | Wood et al. |
| 4,977,886 A | 12/1990 | Takehana et al. |
| 4,979,949 A | 12/1990 | Matsen, III et al. |
| 5,052,402 A | 10/1991 | Bencini et al. |
| 5,072,361 A | 12/1991 | Davis et al. |
| 5,078,140 A | 1/1992 | Kwoh |

| | | | | | | |
|---|---|---|---|---|---|---|
| 5,084,054 A | 1/1992 | Bencini et al. | | 5,878,193 A | 3/1999 | Wang et al. |
| 5,086,401 A | 2/1992 | Glassman et al. | | 5,907,664 A | 5/1999 | Wang et al. |
| 5,116,180 A | 5/1992 | Fung et al. | | 5,928,248 A | 7/1999 | Acker |
| 5,154,717 A | 10/1992 | Matsen, III et al. | | 5,931,832 A | 8/1999 | Jensen |
| 5,172,700 A | 12/1992 | Bencini et al. | | 5,954,692 A | 9/1999 | Smith et al. |
| 5,184,601 A | 2/1993 | Putman | | 5,957,941 A | 9/1999 | Ream |
| 5,217,003 A | 6/1993 | Wilk | | 5,964,717 A | 10/1999 | Gottlieb et al. |
| 5,236,432 A | 8/1993 | Matsen, III et al. | | 5,971,976 A | 10/1999 | Wang et al. |
| 5,238,002 A | 8/1993 | Devlin et al. | | 5,976,122 A | 11/1999 | Madhani et al. |
| 5,238,005 A | 8/1993 | Imran | | 6,001,108 A | 12/1999 | Wang et al. |
| 5,271,381 A | 12/1993 | Ailenger et al. | | 6,007,550 A | 12/1999 | Wang et al. |
| 5,287,861 A | 2/1994 | Wilk | | 6,007,560 A | 12/1999 | Gottlieb et al. |
| 5,299,288 A | 3/1994 | Glassman et al. | | 6,024,695 A | 2/2000 | Taylor et al. |
| 5,339,799 A * | 8/1994 | Kami et al. ................. 600/117 | | 6,036,636 A | 3/2000 | Motoki et al. |
| 5,347,987 A | 9/1994 | Feldstein et al. | | 6,058,323 A | 5/2000 | Lemelson |
| 5,350,355 A | 9/1994 | Sklar | | 6,063,095 A | 5/2000 | Wang et al. |
| 5,368,015 A * | 11/1994 | Wilk ......................... 600/104 | | 6,080,170 A * | 6/2000 | Nash et al. ................. 606/159 |
| 5,372,147 A | 12/1994 | Lathrop, Jr. et al. | | 6,080,181 A | 6/2000 | Jensen et al. |
| 5,382,885 A | 1/1995 | Salcudean et al. | | 6,096,004 A | 8/2000 | Meglan et al. |
| 5,389,100 A | 2/1995 | Bacich et al. | | 6,102,850 A | 8/2000 | Wang et al. |
| 5,397,323 A | 3/1995 | Taylor et al. | | 6,106,511 A | 8/2000 | Jensen |
| 5,402,801 A | 4/1995 | Taylor | | 6,120,433 A | 9/2000 | Mizuno et al. |
| 5,409,019 A | 4/1995 | Wilk | | 6,126,635 A | 10/2000 | Simpson et al. |
| 5,410,638 A | 4/1995 | Colgate et al. | | 6,132,368 A | 10/2000 | Cooper |
| 5,417,210 A | 5/1995 | Funda et al. | | 6,132,441 A | 10/2000 | Grace |
| 5,429,144 A | 7/1995 | Wilk | | 6,156,005 A | 12/2000 | Theron |
| 5,447,149 A | 9/1995 | Kikawada et al. | | 6,171,234 B1 | 1/2001 | White et al. |
| 5,480,422 A | 1/1996 | Ben-Haim | | 6,179,856 B1 | 1/2001 | Barbere |
| 5,497,784 A | 3/1996 | Imran | | 6,197,017 B1 | 3/2001 | Brock et al. |
| 5,515,478 A | 5/1996 | Wang | | 6,206,903 B1 | 3/2001 | Ramans |
| 5,520,644 A | 5/1996 | Imran | | 6,221,070 B1 | 4/2001 | Tu et al. |
| 5,524,180 A | 6/1996 | Wang et al. | | 6,223,100 B1 | 4/2001 | Green |
| 5,540,649 A | 7/1996 | Bonnell et al. | | 6,231,565 B1 | 5/2001 | Tovey et al. |
| 5,553,198 A | 9/1996 | Wang et al. | | 6,233,504 B1 | 5/2001 | Das et al. |
| 5,572,999 A | 11/1996 | Funda et al. | | 6,246,200 B1 | 6/2001 | Blumenkranz et al. |
| 5,606,979 A | 3/1997 | Hodgson | | 6,269,819 B1 | 8/2001 | Oz et al. |
| 5,618,294 A | 4/1997 | Aust et al. | | 6,283,921 B1 | 9/2001 | Nix et al. |
| 5,624,398 A | 4/1997 | Smith et al. | | 6,290,675 B1 | 9/2001 | Vujanic et al. |
| 5,626,553 A | 5/1997 | Frassica et al. | | 6,292,681 B1 | 9/2001 | Moore |
| 5,626,595 A | 5/1997 | Sklar et al. | | 6,309,397 B1 | 10/2001 | Julian et al. |
| 5,631,973 A | 5/1997 | Green | | 6,312,435 B1 | 11/2001 | Wallace et al. |
| 5,632,758 A | 5/1997 | Sklar | | 6,319,227 B1 | 11/2001 | Mansouri-Ruiz |
| 5,634,897 A | 6/1997 | Dance et al. | | 6,325,808 B1 | 12/2001 | Bernard et al. |
| 5,636,634 A | 6/1997 | Kordis et al. | | 6,331,181 B1 | 12/2001 | Tierney et al. |
| 5,649,956 A | 7/1997 | Jensen et al. | | 6,346,072 B1 | 2/2002 | Cooper |
| 5,657,429 A | 8/1997 | Wang et al. | | 6,352,503 B1 * | 3/2002 | Matsui et al. ................ 600/104 |
| 5,667,476 A | 9/1997 | Frassica et al. | | 6,364,888 B1 | 4/2002 | Niemeyer et al. |
| 5,674,279 A | 10/1997 | Wright et al. | | 6,369,834 B1 | 4/2002 | Zilles et al. |
| 5,754,741 A | 5/1998 | Wang et al. | | 6,371,907 B1 | 4/2002 | Hasegawa et al. |
| 5,759,153 A | 6/1998 | Webler et al. | | 6,375,471 B1 | 4/2002 | Wendlandt et al. |
| 5,762,458 A | 6/1998 | Wang et al. | | 6,377,011 B1 | 4/2002 | Ben-Ur |
| 5,784,542 A * | 7/1998 | Ohm et al. ................. 700/260 | | 6,385,509 B2 | 5/2002 | Das et al. |
| 5,792,135 A | 8/1998 | Madhani et al. | | 6,394,998 B1 | 5/2002 | Wallace et al. |
| 5,800,333 A | 9/1998 | Liprie | | 6,398,726 B1 | 6/2002 | Ramans et al. |
| 5,800,423 A | 9/1998 | Jensen | | 6,398,755 B1 | 6/2002 | Belef et al. |
| 5,807,377 A | 9/1998 | Madhani et al. | | 6,432,112 B2 | 8/2002 | Brock et al. |
| 5,808,665 A * | 9/1998 | Green ......................... 348/65 | | 6,436,107 B1 | 8/2002 | Wang et al. |
| 5,810,880 A | 9/1998 | Jensen et al. | | 6,441,577 B2 | 8/2002 | Blumenkranz et al. |
| 5,814,038 A | 9/1998 | Jensen et al. | | 6,451,027 B1 | 9/2002 | Cooper et al. |
| 5,815,640 A | 9/1998 | Wang et al. | | 6,459,926 B1 | 10/2002 | Nowlin et al. |
| 5,821,920 A | 10/1998 | Rosenberg et al. | | 6,463,361 B1 | 10/2002 | Wang et al. |
| 5,823,993 A | 10/1998 | Lemelson | | 6,468,265 B1 | 10/2002 | Evans et al. |
| 5,825,982 A | 10/1998 | Wright et al. | | 6,490,490 B1 | 12/2002 | Uchikubo et al. |
| 5,827,313 A | 10/1998 | Ream | | 6,491,691 B1 | 12/2002 | Morley et al. |
| 5,828,197 A | 10/1998 | Martin et al. | | 6,491,701 B2 | 12/2002 | Tierney et al. |
| 5,833,656 A * | 11/1998 | Smith et al. .............. 604/95.01 | | 6,493,608 B1 | 12/2002 | Niemeyer |
| 5,845,646 A | 12/1998 | Lemelson | | 6,496,099 B2 | 12/2002 | Wang et al. |
| 5,855,553 A | 1/1999 | Tajima et al. | | 6,517,565 B1 | 2/2003 | Whitman et al. |
| 5,855,583 A | 1/1999 | Wang et al. | | 6,522,906 B1 | 2/2003 | Salisbury, Jr. et al. |
| 5,860,992 A | 1/1999 | Daniel et al. | | 6,554,844 B2 | 4/2003 | Lee et al. |
| 5,861,024 A | 1/1999 | Rashidi | | 6,565,554 B1 | 5/2003 | Niemeyer |
| 5,868,755 A | 2/1999 | Kanner et al. | | 6,587,750 B2 | 7/2003 | Gerbi et al. |
| 5,876,325 A * | 3/1999 | Mizuno et al. ................ 600/102 | | 6,594,552 B1 | 7/2003 | Nowlin et al. |

| | | |
|---|---|---|
| 6,620,173 B2 | 9/2003 | Gerbi et al. |
| 6,645,196 B1 | 11/2003 | Nixon et al. |
| 6,676,684 B1 | 1/2004 | Morley et al. |
| 6,685,698 B2 | 2/2004 | Morley et al. |
| 6,692,485 B1 | 2/2004 | Brock et al. |
| 6,699,235 B2 | 3/2004 | Wallace et al. |
| 6,720,988 B1 | 4/2004 | Gere et al. |
| 6,726,675 B1 | 4/2004 | Beyar |
| 6,726,699 B1 | 4/2004 | Wright et al. |
| 6,728,599 B2 | 4/2004 | Wang et al. |
| 6,770,081 B1 | 8/2004 | Cooper et al. |
| 6,783,524 B2 | 8/2004 | Anderson et al. |
| 6,788,018 B1 | 9/2004 | Blumenkranz |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,972 B2 | 11/2004 | Snow |
| 6,817,974 B2 | 11/2004 | Cooper et al. |
| 6,837,883 B2 | 1/2005 | Moll et al. |
| 6,840,938 B1 | 1/2005 | Morley et al. |
| 6,852,107 B2 | 2/2005 | Wang et al. |
| 6,860,877 B1 | 3/2005 | Sanchez et al. |
| 6,911,916 B1 | 6/2005 | Wang et al. |
| 6,936,001 B1 | 8/2005 | Snow |
| 6,936,056 B2 * | 8/2005 | Nash et al. .................. 606/159 |
| 6,951,535 B2 | 10/2005 | Ghodoussi et al. |
| 6,994,708 B2 | 2/2006 | Manzo |
| 7,025,064 B2 | 4/2006 | Wang et al. |
| 7,090,683 B2 * | 8/2006 | Brock et al. ................. 606/130 |
| 2002/0087151 A1 | 7/2002 | Mody et al. |

FOREIGN PATENT DOCUMENTS

| | | |
|---|---|---|
| EP | 0 683 016 A1 | 5/1995 |
| EP | 0776738 A2 | 4/1997 |
| WO | WO 93/14704 | 5/1993 |
| WO | WO98/25666 | 6/1998 |
| WO | WO00/60521 | 10/2000 |
| WO | WO 00/67640 | 11/2000 |
| WO | WO 02/074178 | 2/2002 |

OTHER PUBLICATIONS

Ikuta, et al., "Shape Memory Alloy Servo Actuator System With Electric Resistance Feedback And Application For Active Endoscope", 1988 IEEE, CH2555-1/88/0000/0427-430.

M.W. Thring, "Robots And Telechirs: Manipulators With Memory; Remote Manipulators; Machine Limbs For the Handicapped", First published in 1983 by Ellis Horwood Limited.

* cited by examiner

*Primary Examiner*—Pedro Philogene
(74) *Attorney, Agent, or Firm*—Vista IP Law Group, LLP

(57) ABSTRACT

A remote control flexible instrument system, employing a shaft which supports a tool, is described in which the has proximal and distal ends with at least a portion thereof extending through a lumen of the human body so as to locate the shaft at an internal target site. A master station including an input device provides control of the instrument situated at a slave station. The master station can control at least one degree-of-freedom of the flexible instrument. A controller intercouples the master and slave stations and is operated in accordance with a computer algorithm that receives a command from the input device for controlling at least one degree-of-freedom of the catheter so as to respond in accordance with action at the input device. The flexible instrument further comprises a controlled flexible segment along the shaft, for controlled bending at the flexible segment to guide the shaft and to dispose the tool at an operative site.

86 Claims, 23 Drawing Sheets

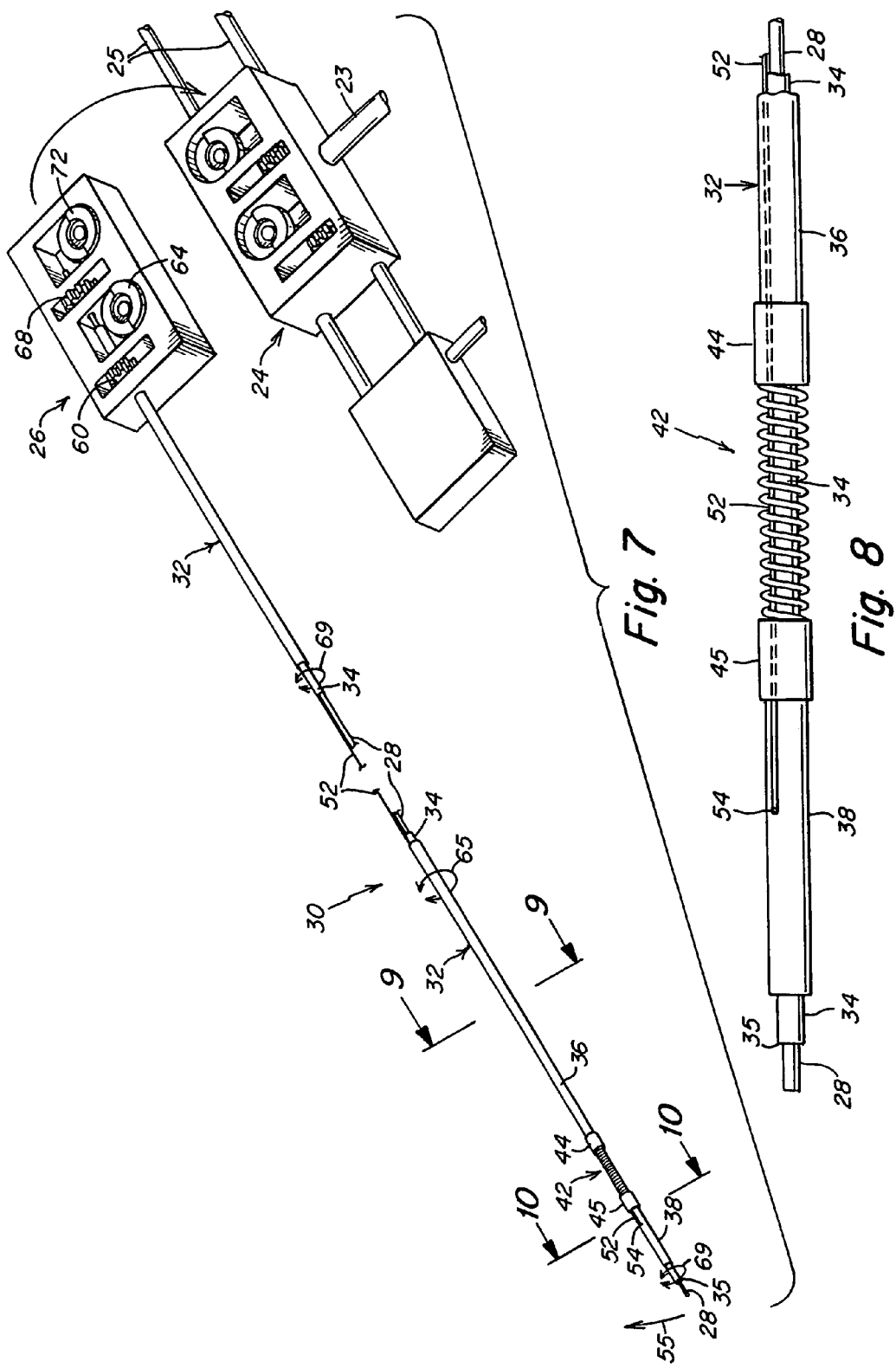

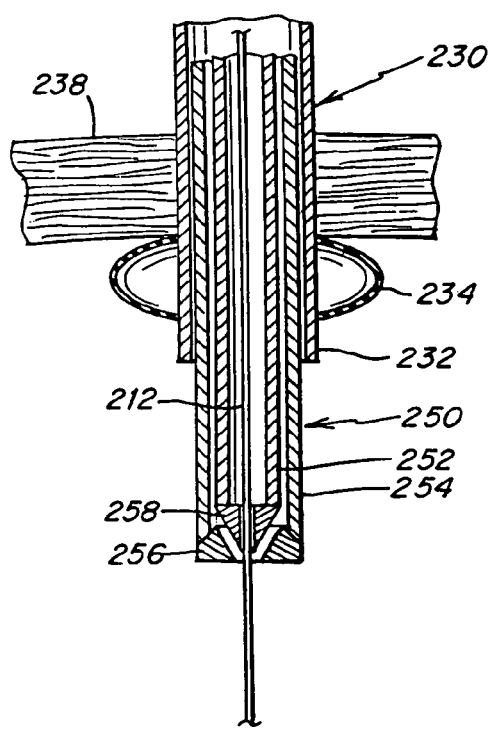
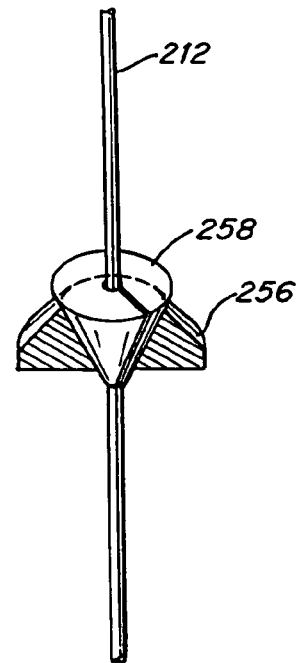
Fig. 21  Fig. 22
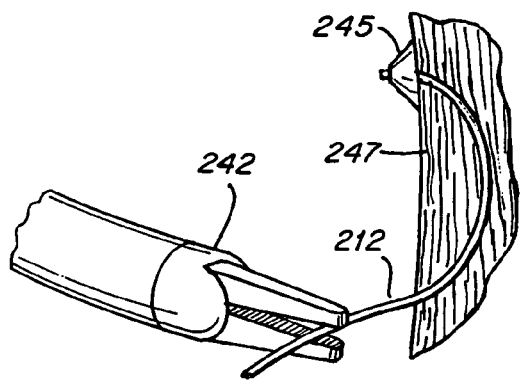
Fig. 23
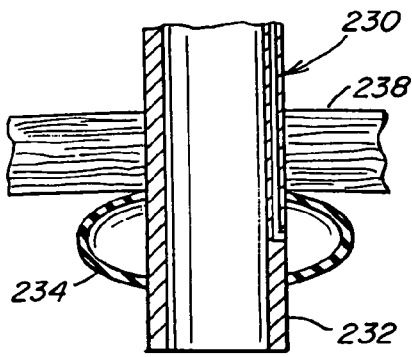
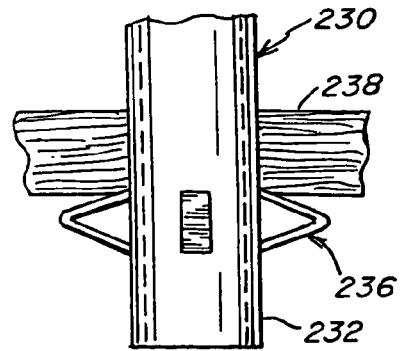
Fig. 24  Fig. 25

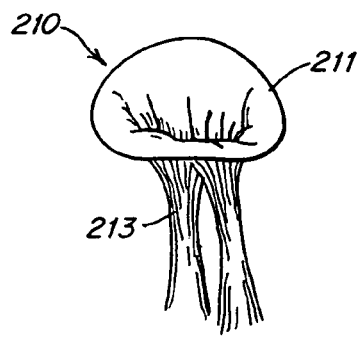
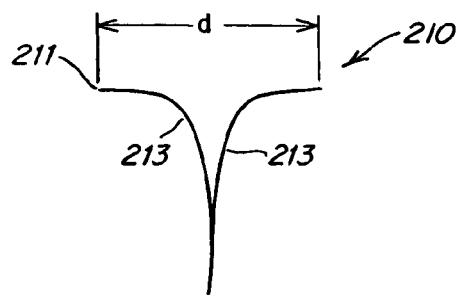
Fig. 26  Fig. 27
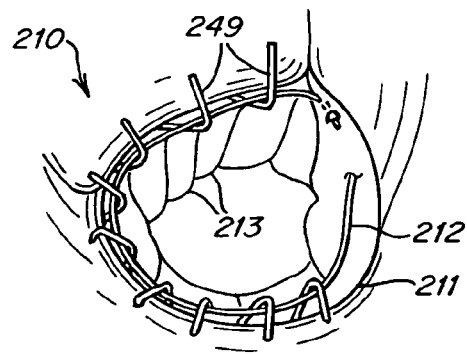
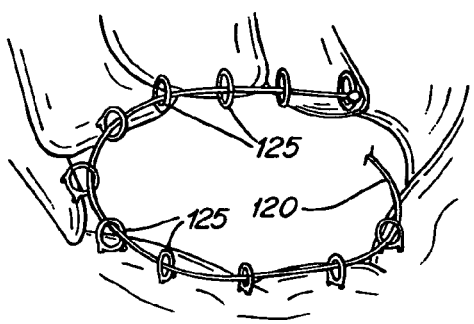
Fig. 28  Fig. 29
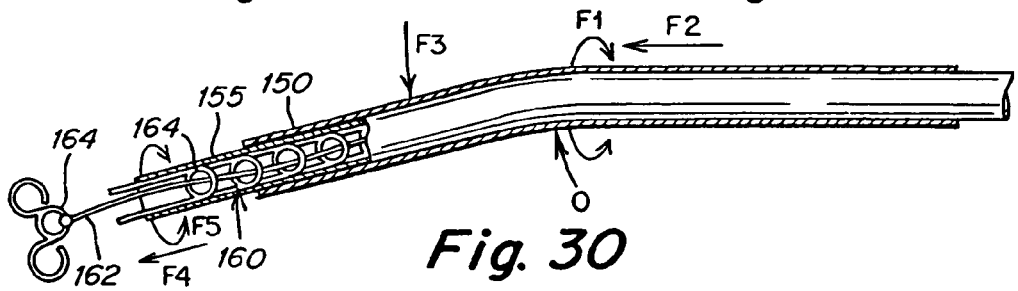
Fig. 30
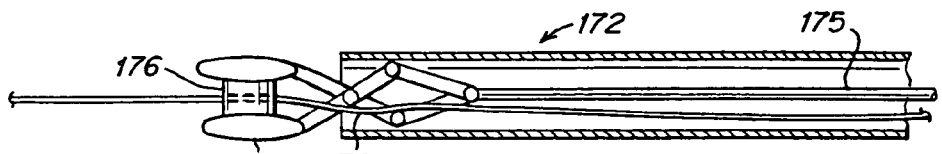
Fig. 30A
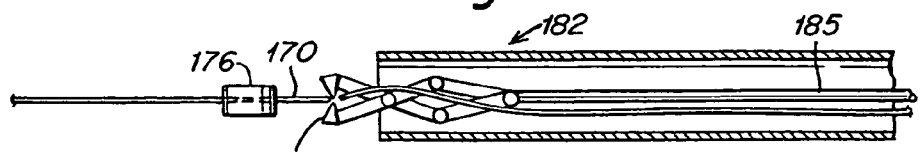
Fig. 30B

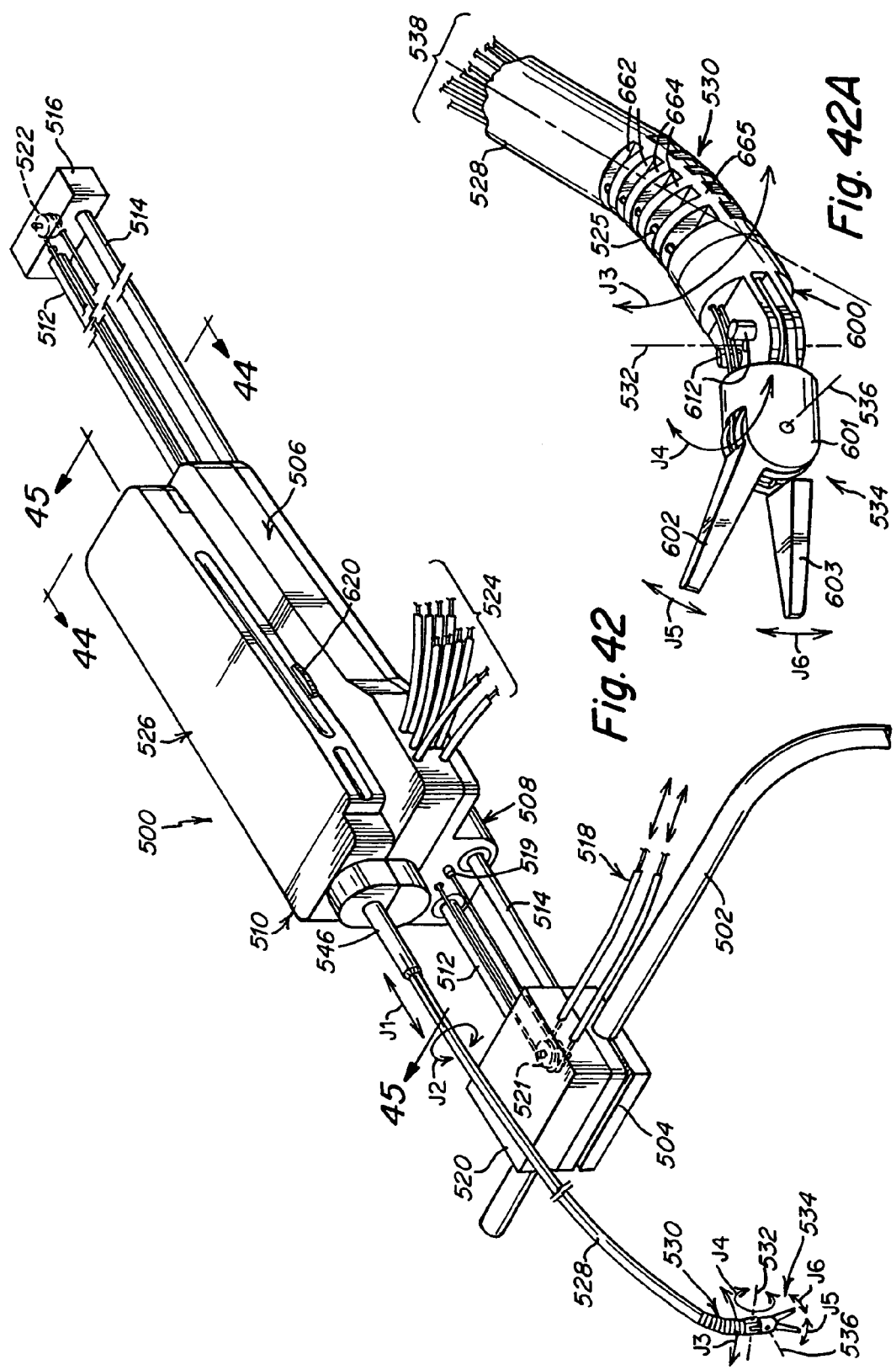

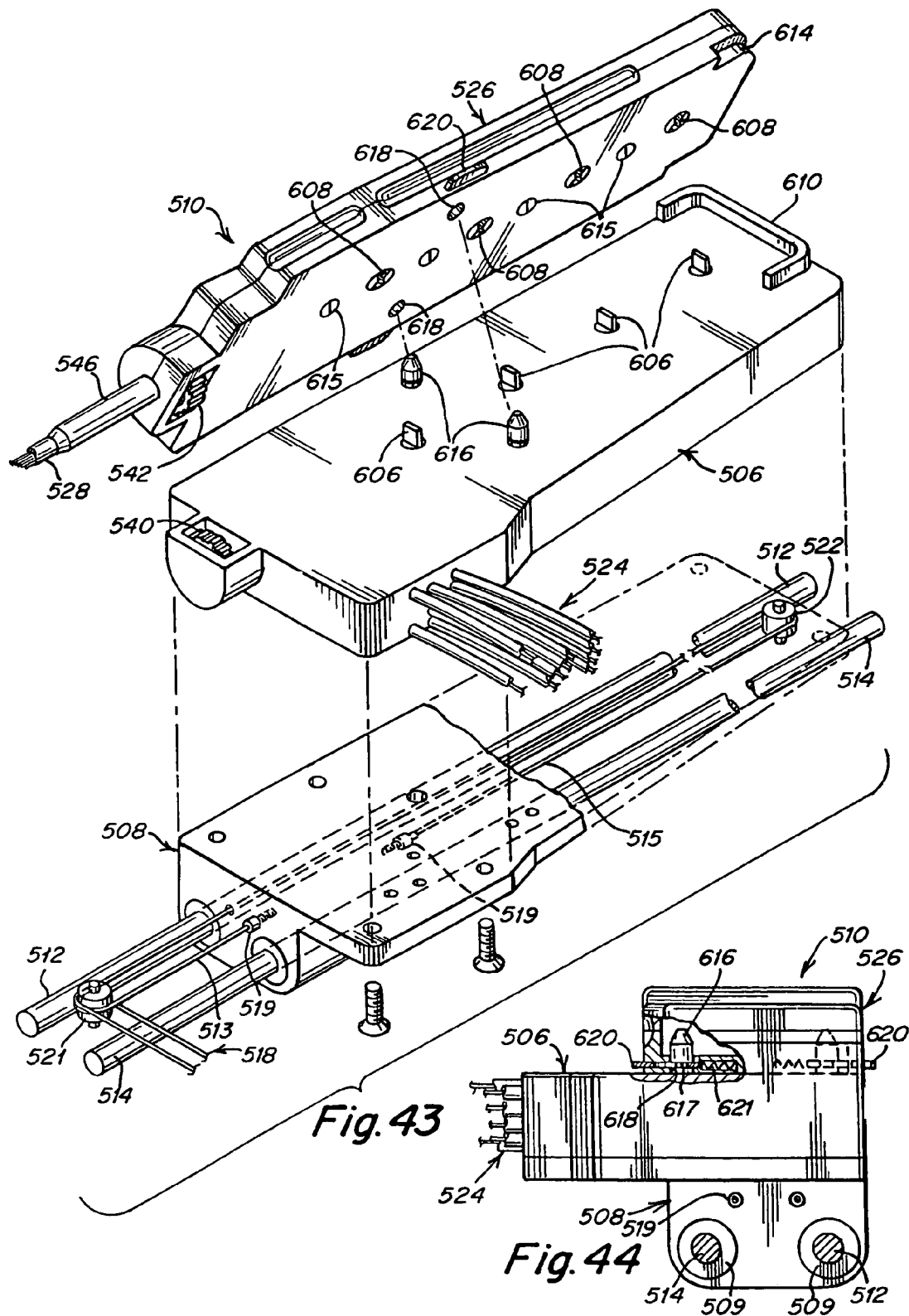

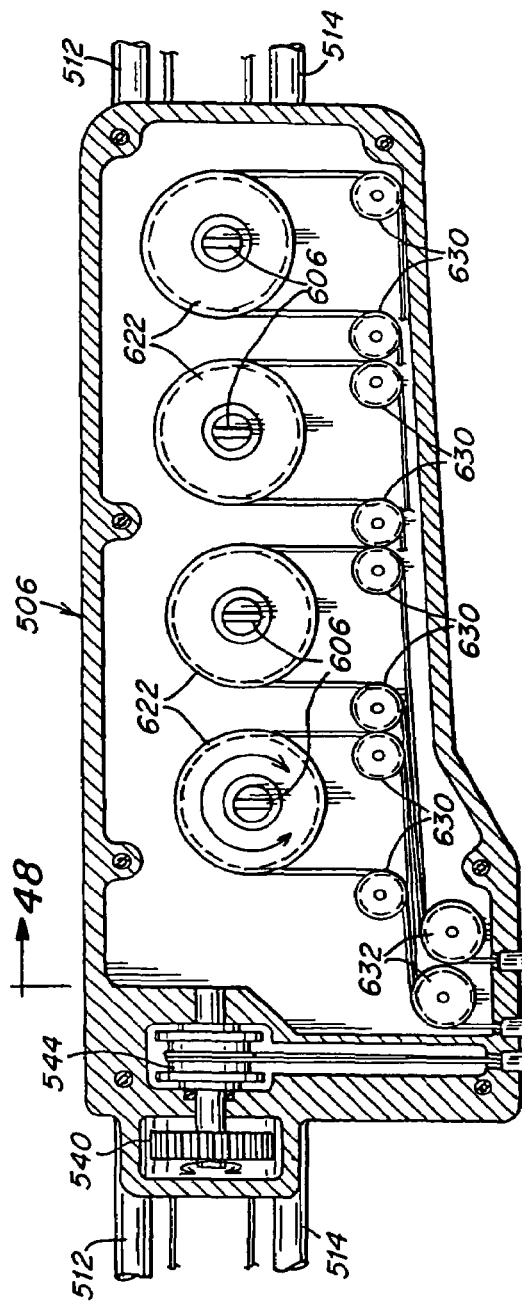
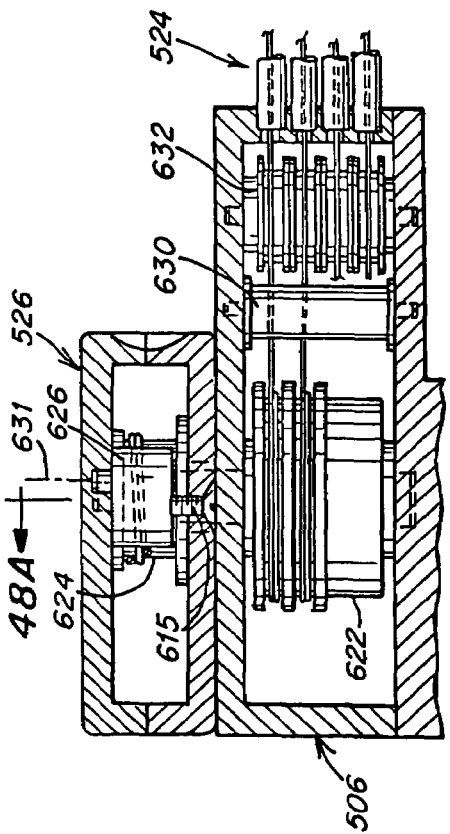
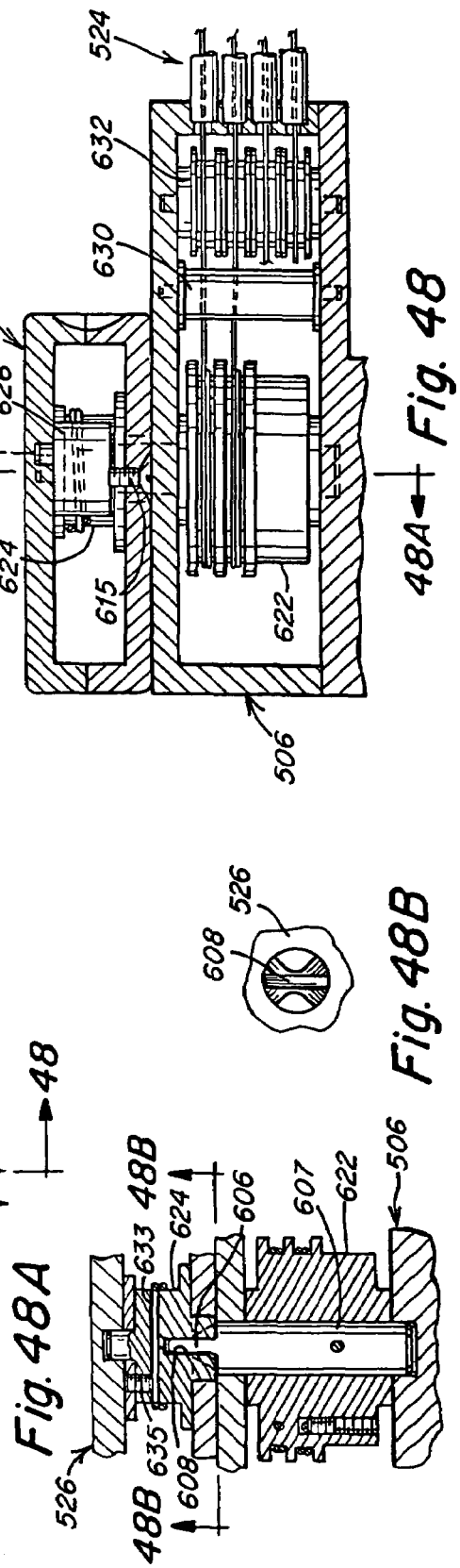
Fig. 47
Fig. 48
Fig. 48A
Fig. 48B

FLEXIBLE INSTRUMENT

CROSS REFERENCE TO RELATED APPLICATIONS

This application is a continuation-in-part of and claims the benefit of priority from U.S. application Ser. No. 09/827,503, filed Apr. 6, 2001 now U.S. Pat. No. 6,432,112, which is a continuation of U.S. application Ser. No. 09/746,853, filed Dec. 21, 2000 now U.S. Pat. No. 6,692,485, which is a divisional of U.S. application Ser. No. 09/375,666, now U.S. Pat. No. 6,197,017, filed Aug. 17, 1999, which is a continuation of U.S. application Ser. No. 09/028,550 filed Feb. 24, 1998, now abandoned. This application is also a continuation-in-part of and claims the benefit of priority from U.S. application Ser. No. 09/783,637, filed Feb. 14, 2001 now abandoned, which is a continuation of PCT/US00/12553 filed May 9, 2000, which claims the benefit of priority of U.S. provisional patent application Ser. No. 60/133,407, filed May 10, 1999, now abandoned. This application is also a continuation-in-part of and claims the benefit of priority from PCT/US01/11376 filed Apr. 6, 2001 which claims priority to U.S. application Ser. Nos. 09/746,853 filed Dec. 21, 2000 now U.S. Pat. No. 6,692,485 and 09/827,503 filed Apr. 6, 2001. This application is also a continuation-in-part of and claims the benefit of priority from U.S. application Ser. Nos. 09/746,853 filed Dec. 21, 2000 and 09/827,503 filed Apr. 6, 2001. This application is also a continuation-in-part of and claims the benefit of priority from U.S. application Ser. No. 09/827,643 filed Apr. 6, 2001 which claims priority to, inter alia, U.S. provisional application Ser. No. 60/257,869 filed Dec. 21, 2000 and U.S. provisional application Ser. No. 60/195,264 filed Apr. 7, 2000 and is also a continuation-in-part of PCT/US00/12553 filed May 9, 2000 from which U.S. application Ser. No. 09/783,637 filed Feb. 14, 2001 claims priority.

This application also claims the benefit of priority under 35 U.S.C. §§119 and 120 to U.S. Provisional Application Ser. No. 60/293,346 filed May 24, 2001, U.S. Provisional Application Ser. No. 60/279,087, filed Mar. 27, 2001, U.S. Provisional Application Ser. No. 60/313,496 filed Aug. 21, 2001, U.S. Provisional Application Ser. No. 60/313,497 filed Aug. 21, 2001, U.S. Provisional Application Ser. No. 60/313,495 filed Aug. 21, 2001, U.S. Provisional Application Ser. No. 60/269,203 filed Feb. 15, 2001, U.S. Provisional Application Ser. No. 60/269,200 filed Feb. 15, 2001, U.S. Provisional Application Ser. No. 60/276,151 filed Mar. 15, 2001, U.S. Provisional Application Ser. No. 60/276,217 filed Mar. 15, 2001, U.S. Provisional Application Ser. No. 60/276,086 filed Mar. 15, 2001, U.S. Provisional Application Ser. No. 60/276,152 filed Mar. 15, 2001, U.S. Provisional Application Ser. No. 60/257,816 filed Dec. 21, 2000, U.S. Provisional Application Ser. No. 60/257,868 filed Dec. 21, 2000, U.S. Provisional Application Ser. No. 60/257,867 filed Dec. 21, 2000, U.S. Provisional Application Ser. No. 60/257,869 filed Dec. 21, 2000.

The disclosures of all of the foregoing applications and U.S. Pat. No. 6,197,017 are all incorporated herein by reference in their entirety.

This application further incorporates by reference in its entirety the disclosures of the following U.S. patent applications which are being filed concurrently on the same date herewith, having the following titles and Ser. Nos. 10/014,143—Surgical Instrument; 10/012,845—Surgical Instrument; 10/008,964—Surgical Instrument; 10/013,046—Surgical Instrument; 10/011,450—Surgical Instrument; 10/008,487—Surgical Instrument; 10/008,871—Surgical Instrument; 10/023,024—Flexible Instrument; 10/023,024—Flexible Instrument; 10/011,371—Flexible Instrument; 10/011,449—Flexible Instrument; 10/010,150—Flexible Instrument; 10/022,038—Flexible Instrument; and 10/012,586—Flexible Instrument.

FIELD OF THE INVENTION

The present invention relates in general to a remote controlled flexible instrument comprising a flexible shaft, for introduction into a body cavity or body vessel to perform a medical procedure.

BACKGROUND OF THE INVENTION

Catheters are used extensively in the medical field in various types of procedures, including invasive procedures. Minimally invasive surgery involves operating through small incisions, through which instruments are inserted. These incisions are typically 5 mm to 10 mm in length. Minimally invasive surgery is typically less traumatic than conventional surgery, due, in part, to the significant reduction in incision size. Furthermore, hospitalization is reduced and recovery periods shortened as compared with conventional surgery techniques. Catheters may be tailored to a particular size or form, depending on the incision and the size of the body cavity or lumen.

Due to the small size of the incision, the bulk of the surgery is not visible. Although the surgeon can have visual feedback from the surgical site via a video camera or endoscope inserted into the patient, or via radiological imaging or ultrasonic scanning, the ability to control the relatively simple laparoscopic instruments remains difficult. Even with good visual feedback, the surgeon's tactile and positional senses are physically removed from the operative site, rendering endoscopic procedures slow and clumsy.

Current instrumentation, with forceps, scissors, etc., inserted into the body at the end of long slender push rods is not fully satisfactory. The use of such conventional instrumentation increases operative time, and potentially heightens risk. For example, tissue may be injured when the laparoscopic tool moves outside the visual field. Moreover, there are limitations on the type and complexity of procedures that may be performed laparoscopically due, in part, to the limitations on the instruments that are used.

Development work has been undertaken to investigate the use of robotic work in surgery. Typically, these robotic systems use arms that reach over the surgical table and manipulate surgical instruments. The known robotic systems are large, clumsy to operate and relatively expensive to manufacture. The presence of a robot at the surgical site is problematic particularly when the robot is large and may impede access to the patient during surgery.

SUMMARY OF THE INVENTION

The present invention features, at least in part, an improved, remote controlled surgical system that does not impede access to the patient during surgery, yet is simple to operate. The present invention provides a surgical instrument system particularly adapted for a variety of medical procedures, including minimally invasive surgery.

One aspect of the present invention provides a surgical instrument comprising a shaft having at least one controllably flexible segment and a tool mounted at a distal end of the shaft. The tool is insertable into a subject. The instrument further comprises a shaft mount drivably coupled to the shaft at a proximal end of the shaft where the shaft mount is then drivably coupled to the tool through the shaft. The instrument also comprises a drive unit drivably coupled to the shaft mount. The drive unit is operable from a location remote from the subject to control flexure of the flexible segment so as to control disposition of the tool at an operative site.

Another aspect of the present invention provides a remotely controllable surgical instrument comprising a user input device for inputting a command. A slave station receives the command from the input device. The user input device is remotely disposed from the slave station. The slave station further comprises a mechanically drivable mechanism comprising a shaft having a proximal end, a distal end supporting a tool and a flexible portion between the proximal and distal ends. An electronic signal link is between the user input device and the slave station receives a the command from the input device being communicated via the link, for controlling bending of the flexible portion so as to controllably position the tool at an operative an site of a subject.

Another aspect of the present invention provides a remotely controllable catheter comprising a tube having a proximal end and a distal end. At least a segment of the tube is controllably flexible. The catheter also comprises a drivable bending mechanism mechanically coupled to and interactive with a controllably flexible segment of the tube. A computer remote from and interconnected to the bending mechanism has a computer for receiving input from the user. The program directs the bending mechanism to controllably flex the flexible segment of the tool according to the user input.

Another aspect of the present invention provides a catheter comprising a shaft having proximal and distal ends and at least one flexible segment along a length of the shaft. The distal end is insertable within a body cavity or a vessel. A tool is supported at the distal end of the shaft for performing a medical procedure. At least two cables extend along the shaft between the proximal and distal ends. At least one of the cables is associated with the flexible segment to the shaft and at least another of the cables is associated with a tool. An electronic control mechanism is drivably coupled to the cables where the electronic control mechanism is capable of communicating drive signals from a user input device to the cable to affect bending of the flexible segment and operation of the tool.

One aspect of the present invention provides a medical device comprising disposable mechanically drivable mechanism drivably coupled to a tool via a disposable shaft for insertion into a body vessel or cavity along a selected length of the shaft. The tool is operable to carry out a medical procedure and the shaft is disposable together with the mechanically drivable mechanism. A receiver receives a mechanically drivable mechanism. The medical device further comprises a drive unit coupled to the receiver.

Another aspect of the present invention provides a medical device comprising a disposable implement comprising a disposable flexible shaft supporting a tool at its distal end for insertion into a subject, and a disposable first drive interface drivably coupled with a tool to the shaft. The medical device further comprises a second drive interface, for drivably coupling the disposable implement with a drive unit. The second drive interface is drivably engageable with a disposable implement via the first drive interface.

Another aspect of the present invention provides a disposable medical device comprising a disposable flexible shaft having a proximal end and a distal end. A disposable mechanically drivable interface is connected to the proximal end of the shaft. A tool is mounted at the distal end of the shaft. The device further comprises at least one disposable cable drivably interconnected between the mechanically drivable interface in the tool. The mechanically drivable interface is interconnected to a remotely disposed electronic control mechanism which controls drive operation of the device.

Another aspect of the present invention provides a disposable electronically controlled surgical instrument comprising a disposable flexible elongated shaft having a proximal end and a distal end on which is mounted a tool. The proximal end of the shaft is connected to a mechanically drivable interface. The disposable shaft includes at least one disposable cable drivably interconnected between the mechanically drivable interface and the tool. The mechanically drivable interface is interconnected to a remotely disposed electronic control mechanism which controls drive operation of the device.

One aspect of the present invention provides a medical device comprising a flexible guide shaft having a distal end disposed at a predetermined location in the subject. The device comprises a flexible inner shaft having a proximal end and a distal end supporting at its distal end a tool. The inner shaft is insertable into the guide shaft so as to dispose a tool at an operative site. The device further comprises a drive unit coupled to the inner shaft for providing controlled actuation of the tool. The drive unit is remote controllably drivable by a user via a manually controllable device.

Another aspect of the present invention provides a medical device comprising a flexible inner shaft inserted within a flexible guide shaft. A tool is disposed at a distal end of the inner shaft for insertion into a subject. A drive unit is coupled with an inner shaft and a guide shaft independently. The drive unit is capable of independently effecting movement of each shaft to at least one degree of freedom. A user input interface is remote from the drive unit, where the input inference face is for remote controllably manipulating the inner and guide shaft.

Another aspect of the present invention provides a medical device comprising a flexible guide shaft having a distal end disposed at a predetermined location in a subject. A flexible disposable inner shaft has a proximal end and a distal end supporting at its distal end a tool. The inner shaft is insertable to the guide shaft so as to dispose the tool at an operative site. The drive unit is coupled with the inner shaft for providing controlled actuation of the tool and controlled deformation of one or more flexible portions of the inner shaft. The drive unit is remote controllably drivable by the user via a manually controllable device. The proximal end of the inner shaft includes a mechanically operative element drivably couplable to the drive unit. The mechanically operative element is disposable together with the tool as a unit.

One aspect of the present invention provides a medical device comprising a mechanically drivable mechanism coupled with a shaft including a flexible segment, where a distal end of the shaft supports a tool insertion into a subject. A drive unit is coupled with a mechanically drivable mechanism and disposed remotely from the sterile field. The drive unit is for intercoupling drive from the drive unit to the drivable mechanism. The drive unit is capable of activating the flexible segment via the mechanically drivable mechanism for actuation of the tool and positioning of the tool at the operative site within the subject.

Another aspect of the present invention provides an apparatus for use in a body cavity or vessel comprising a catheter having a proximal end and a distal end for placement in the body cavity or vessel. A tool is positioned at the distal end of the catheter. A flexible segment is positioned between the distal and proximal ends of the catheter. Cables extend from a drive unit through the flexible segment. The drive unit is operable from a remote site and capable of bending the flexible segment via the cables for actuation of the tool.

Another aspect of the present invention provides a remotely driven surgical instrument comprising an elongate flexible shaft having a proximal end and a distal end supporting a surgical tool. The shaft is insertable into a subject for disposition of the tool at an operative site of the subject. An electronically controllable drive unit is mounted in a location remote from the subject. The remote drive unit includes one or more motors drivably interconnected to the proximal end of a flexible shaft by one or more motor driven cables, which are readily drivably interconnectable to and disconnectable from the proximal end of the flexible shaft.

One aspect of the present invention provides a robotic medical system comprising a flexible instrument having flexible and distal ends with at least one flexible segment extending through a lumen of the human body. The at least one flexible segment is controllably bendable so as to locate a distal end of the shaft at an internal target site. A tool is carried at the distal end of the shaft for performing a procedure. A master station includes an input device. A slave station includes a receiver for the catheter for controlling through the receiver at least one degree of freedom of the catheter. A controller is coupled between the master station and the slave station and is operated in accordance with computer algorithm that receives a command from the input device and for controlling the at least one degree of freedom of the catheter so as to respond in accordance with action at the input device.

Another aspect of the present invention provides a method of remotely controlling a catheter comprising providing a flexible shaft having a distal end supporting a tool. The shaft includes at least one controlled flexible segment about the distal end capable of controlled vending for positioning the tool at an operative site. The method comprises inserting the shaft into an anatomic lumen where the flexible shaft is adapted to conform to the configuration of the anatomic lumen. The method comprises mechanically driving, via a drive unit, a cabling system extending through the shaft and the at least one flexible segment. The at least one controlled flexible segment is activated by operating the drive unit from a location remote from the shaft so as to affect bending of the at least one flexible segment and thereby effect positioning of the tool to a target site.

Another aspect of the present invention provides a flexible instrument system comprising a flexible shaft having a proximal end and a distal end. The distal end supports a tool. The shaft is insertable into a subject so as to dispose the tool at an operative site. A mechanically drivable mechanism is disposed at the proximal end of the shaft. The mechanically drivable mechanism is capable of offering the tool via at least one flexible segment positioned along the shaft. A receiver is supported in a fixed portion of the subject for receiving and storing the shaft via the mechanically drivable mechanism in a position to maintain the tool at the operative site. A computation system receives electrical control signals from a user input device for controlling the shaft.

Another aspect of the present invention provides a flexible instrument system comprising a medical implement having sufficient flexibility along a length thereof so as to at least flex and conform to a pathway in an anatomic vessel or cavity as the implement is inserted therein. The medical implement comprises a tool for performing a medical procedure and a flexible shaft having proximal and distal ends. The shaft supports the tool at the distal end and is insertable go into a subject so as to dispose the tool at an operative site via controlled bending of at least one flexible segment positioned along the shaft. The medical implement also comprises a mechanically drivable mechanism disposed at the proximal end of the shaft. The system comprises a drive unit intercoupled with a medical implement and includes at least a first cable intercoupled with a tool and at least a second cable intercoupled with a shaft for controlling a bend at the at least one flexible segment.

Another aspect of the present invention provides a flexible instrument system comprising a drive unit for controlling operation of a medical implement. A mechanical actuation system extends from the drive unit. The medical implement has sufficient flexibility to conform to a pathway in an anatomic vessel or cavity as the implement inserted therein. The medical implement comprises a flexible shaft having proximal and distal ends where the flexible shaft is insertable into a subject so as to dispose the distal end at an operative site. The shaft further comprises at least one controlled flexible segment actuating a controlled bend. The medical implement also comprises a mechanically drivable mechanism disposed at a proximal end of the flexible shaft.

One aspect of the present invention provides a system for preparing a cardiac valve comprising a flexible guide shaft extending from a site outside a patient to an area about the cardiac valve. A flexible inner shaft supports at its distal end a remotely controlled tool for performing a cardiac repair procedure. The inner shaft is received in the guide shaft for disposing the tool at the area about the cardiac valve. A retainer is positioned at the area of the cardiac valve. The retainer is attached to an annulus of the cardiac valve and is closable via the tool to draw the annulus into a smaller diameter.

Another aspect of the present invention provides the method of repairing a mitral valve of the heart. The method comprises extending a guide shaft from a site outside the patient to a site adjacent the mitral valve. The method comprises inserting a fiber through the guide shaft and securing the fiber about an annulus of the mitral valve while the heart is beating. The securing step includes introducing through the guide shaft a flexible inner shaft having a remotely controlled distal tool for securing the fiber about the annulus leaving opposite ends of the fiber exposed. The method for this comprises applying a force to the fiber ends so as to draw the annulus into a tighter diameter.

Another aspect of the present invention provides a system for remotely repairing a cardiac valve comprising a guide catheter extending through an area of the human body where a distal end of the guide catheter is disposed at an area about the cardiac valve. A fiber extends about a diameter of an annulus of the cardiac valve. The fiber is engaged with a diameter of the annulus and capable of drying the annulus to a smaller diameter. The system comprises a flexible working catheter received by the guide catheter, where the working catheter includes a tool engageable with a fiber. A remote manipulator is controlled from a site remote from the body, for controlling the tool.

Another aspect of the present invention provides a method of repairing a mitral valve of the heart, comprising extending a guide shaft from a site outside the patient to a site about the mitral valve. The method comprises providing a ring of a first diameter where the ring is deformable and capable of matching a desired predetermined diameter of an annulus of the mitral valve. The ring is engaged with a guide shaft via a flexible inner shaft received by the guide shaft. The ring is secured about the mitral valve annulus while the heart is beating. The securing step includes engaging the ring about a circumference of the annulus via a remotely controlled tool supported at a distal end of the inner shaft. The annulus is drawn into the predetermined diameter.

Another aspect of the present invention provides a method of repairing a cardiac valve comprising providing a balloon supported on a catheter. A plurality of peripherally disposed anchor pins is supported from an outer surface of the lumen where the anchor pins are tethered to each other. The balloon is passed in a deflated state to an area about the cardiac valve. The method comprises inflating the balloon to thrust the anchor pins into an annulus of the cardiac valve. The tether is tightened to pull the peripherally disposed pins into a smaller diameter.

Another aspect of the present invention provides a method for repairing a cardiac valve comprising providing a balloon and supporting and passing the balloon in a deflated state to an area about the cardiac valve. A plurality of peripherally disposed anchor pins is disposed and arranged about an outer surface of the balloon. A tether is provided for intercoupling the anchor pins. The balloon is inflated once it is positioned at the area about the cardiac valve, to thrust the anchor pins into a ring defining a base of the cardiac valve. A tether is tightened to pull the peripherally disposed pins into a smaller diameter.

Another aspect of the present invention provides a system for remotely repairing a cardiac valve comprising a flexible guide shaft extending to an area of the human body so as to locate a distal end thereof at an area about the cardiac valve. A delivery member, for supporting an array of securing pieces at a distal end thereof, extends through the flexible guide member. The array of securing pieces is intercoupled by a cable. A remote manipulator is controlled from a slight remote from the body, for controlling the delivery member to expel the securing pieces in sequence about the cardiac valve annulus as the valve is functioning. The remote manipulator is capable of controlling a tightening of the cable to draw the annulus into a smaller diameter.

Another aspect of the present invention provides a flexible instrument system for repairing an anatomic body part comprising a shaft having sufficient flexibility along the length thereof so as to readily flex and conform to a pathway in the anatomy as the shaft is inserted therein. A drivable mechanism is disposed at a flexible end of the shaft controlling a tool supported at a distal end of the shaft. The shaft is insertable into a subject so as to dispose the distal end of the shaft at an internal site of an anatomical body part. A retainer is attached to an annulus at the anatomic body part where the retainer is closable so as to draw the annulus into a smaller diameter.

BRIEF DESCRIPTION OF THE DRAWINGS

Numerous other objects, features and advantageous of the invention should now become apparent upon a reading of the following detailed description taken in conjunction with the accompanying drawings in which:

FIG. 7 is a more detailed perspective view of the catheter apparatus;

FIG. 8 is an enlarged view of a portion of the catheter apparatus particularly at the distal end section thereof;

FIG. 21 is a more detailed cross-sectional drawing of the portion of the mechanical member, particularly the means for tightening the retaining means;

FIG. 22 shows further details of the structure of FIG. 21;

FIG. 23 is a schematic illustration of a section of the mitral valve ring showing the fiber and the securing of one end of the fiber;

FIG. 24 illustrates somewhat further detail of a means for retaining the catheter in position;

FIG. 25 is a diagram illustrating alternate means for holding the catheter in place;

FIG. 26 illustrates a view of a mitral valve;

FIG. 27 is a schematic diagram of the mitral valve indicating the ring area and leaflets;

FIG. 28 is a schematic illustration showing the mitral valve construction and a mechanical member for retaining and tightening;

FIG. 29 is schematic diagram of another technique for mitral valve repair employing a wire to be tightened like a lasso;

FIG. 30 is a schematic diagram illustrating a catheter and tool construction containing a tether cable and anchor elements within the inner catheter;

FIG. 30A shows a cable termination tool for crimping;

FIG. 30B shows a tool for cutting;

FIG. 42 is a perspective view of another embodiment of the present invention;

FIG. 42A is an enlarged detail perspective view of the tool;

FIG. 43 is an exploded perspective view of, in particular, the interlocking modules of the flexible instrument system of FIG. 42;

FIG. 44 is a partially broken away rear elevational view of the interlocking modules as seen along line 44-44 of FIG. 42;

FIG. 47 is a cross-sectional plan view taken through the base module of the system of FIG. 42, and as taken along line 47-47 of FIG. 45;

FIG. 48 is a cross-sectional end view taken along line 48-48 of FIG. 47;

FIG. 48A is a cross-sectional view taken along line 48A-48A of FIG. 48;

FIG. 48B is a fragmentary plan view of a drive wheel engagement slot by itself as taken along line 48B-48B of FIG. 48A.

DETAILED DESCRIPTION

The present invention provides a system for remotely controlling a flexible instrument for use in medical applications, typically for operative or other medical procedures. The flexible instrument comprises a shaft or a tube of sufficient dimensions for passing through a small incision or natural body lumen or cavity and ultimately, for positioning a distal end of the shaft within the body at an internal target (operative) site. The flexible instrument can also support a tool at its distal end to allow more intricate medical procedures. A user or surgeon can control the position of the shaft from a master station, allowing operation from another part of the operating room, or even from another room or another building. In one aspect of the invention, the shaft can comprise one or more flexible segments, which a user can controllably bend, providing finer control in directing the shaft toward the target site. The control can result in, for example, a deflection or turning of the shaft, for guiding this shaft through or within various body cavities or lumens. The controllable bending is also useful for more precise positioning of a distal end of the flexible instrument at a desired operative site.

Preferably, the flexible instrument is used to perform minimally invasive procedures. "Minimally invasive procedure," refers herein to a surgical procedure in which a surgeon operates through small cut or incision, the small incision being sufficiently necessary to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, if necessary, so as to locate the catheter at an internal target site for a particular surgical or medical procedure. Examples of such minimally invasive procedures include intravascular procedures, such as the repair of a cardiac valve. The introduction of the flexible instrument into the anatomy may be by percutaneous or surgical access to a lumen or vessel, or by introduction through a natural orifice in the anatomy.

Figure 1:
FIG. 1 is a simplified block diagram illustrating basic components of a system constructed in accordance with the present invention.

FIG. 1 is a block diagram schematically illustrating the three main components of the remote control system of the present invention. A surgeon or user can input control actuations at master station 1, typically through an input device (not shown). Slave station 3 is separate and remote from the master station and controls the motion of the flexible instrument, in accordance with the user input from master station 1. Master station 1 and slave station 3 may be in relatively close proximity to each other, such as in the same operating room, or can be displaced from each other by miles. Controller 2 provides a telecommunications or electronic communications link coupled between the master station and the slave station. Controller 2 typically includes a computer. Controller 2 receives a command from the input device of master station 1 and relays this command to slave station 3.

Figure 6:
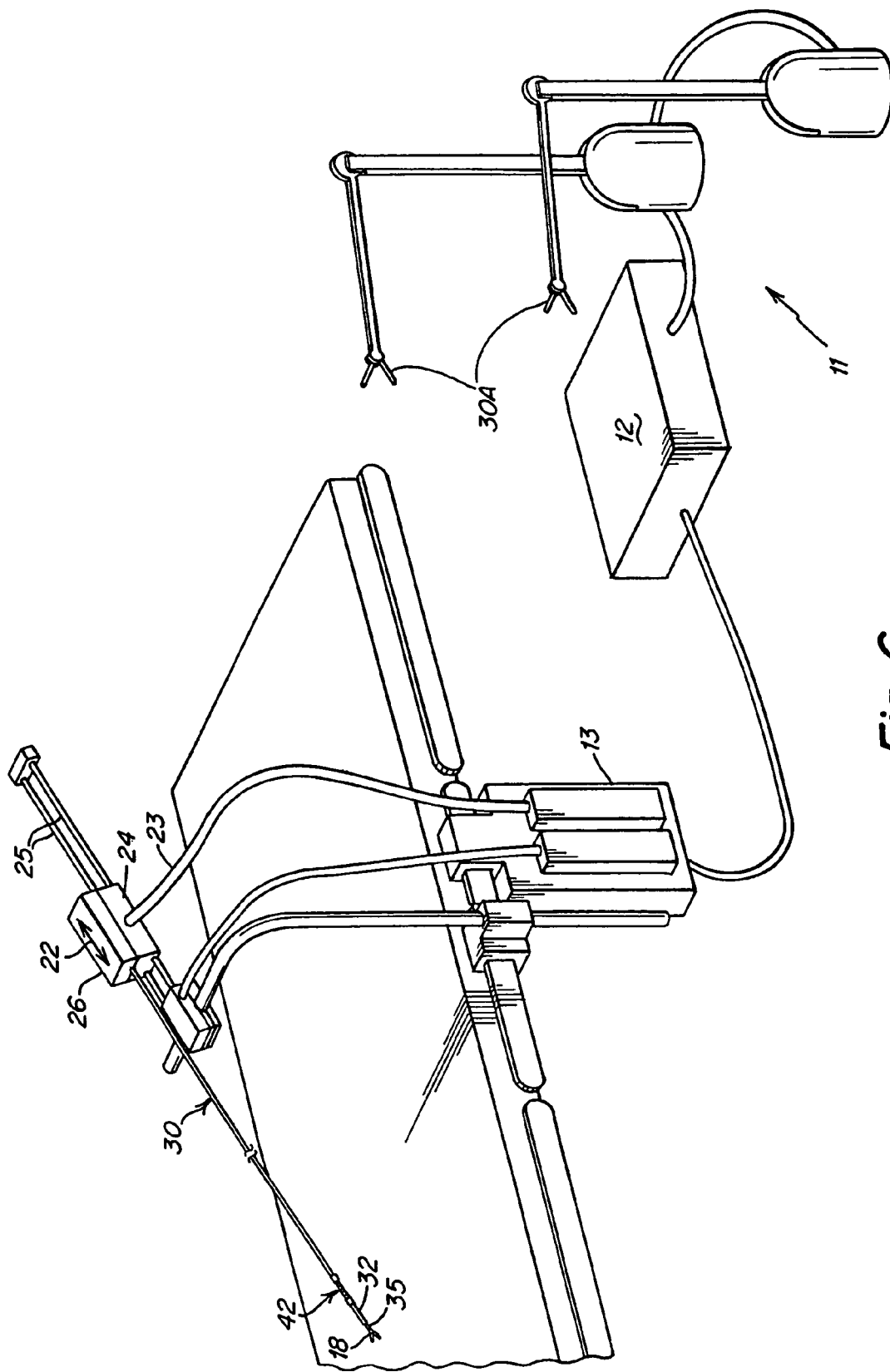
FIG. 6 is a perspective view of one embodiment of a system embodying the catheter apparatus of the present invention.
Figure 9:
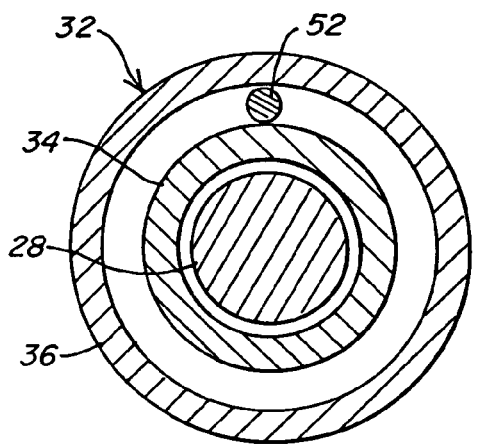
FIG. 9 is a cross-sectional view through the catheter apparatus as taken along line 9-9 of FIG. 7.
Figure 10:
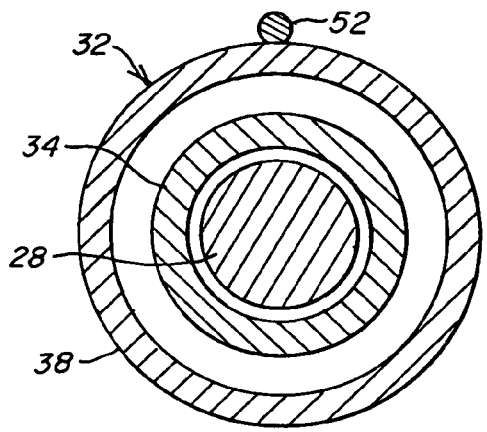
FIG. 10 is a cross-sectional view through the catheter apparatus as the distal end section thereof, as taken along line 10-10 of FIG. 7.

FIG. 6 is a schematic of the remote control system of the present invention. The system includes: (1) A master station comprising a user interface or surgeon's interface 11; (2) A slave station comprising a flexible instrument including shaft 30 which supports tool 18. Shaft 30 is connected to and is controllable from mechanically drivable mechanism 26, which in turn is engageably received by receiver 24, both of which are mechanically driven by drive unit 13, (alternatively mechanical drive 13); and (3) a controller or computation system 12 to translate a user's commands from user interface 11 to drive unit 13, which then drives the articulations of shaft 30 and tool 18. FIG. 6 illustrates a system where a user or surgeon can control shaft 30 and tool 18 by manipulating interface handles 30A of user interface 11. The movement of handle 30A causes responsive movement of tool 18 through the coordinating action of computation system 12. For example, tool 18 can be a pair of graspers, scissors, staplers, etc. and manipulation of handle 30A can cause the jaws of tool 18 to open and close.

Surgeon's interface 11 is in electrical communication with computing system 12, which is, in turn, in electrical communication with drive unit 13. In one embodiment, drive unit 13 comprises a plurality of motors. The drive unit 13 is in mechanical communication with shaft 30 via conduit 23, which houses a plurality of mechanical cables driven by the plurality of motors in drive unit 13. In one embodiment, drive unit 13 is solely in mechanical communication with shaft 30. Because of the mechanical communication with shaft 30, the electromechanical components in drive unit 13 are disposed in an area remote from the operative site, and preferably in an area outside the sterile field. Preferably, objects that are difficult to sterilize, e.g. motors or electromechanical components, are kept at a sufficient distance from the patient to avoid contamination. This distance is readily ascertainable by doctors, nurses, and other appropriate medical professionals. In one embodiment, the sterile field has the rest surface of the operating table as its lower boundary. Thus, drive unit 13 is preferably located below the plane of the sterile field, i.e. below the rest surface of the operating table. The patient or subject may be further protected from drive unit 13 with a sterile barrier, such as a sterile cloth. With respect to the drive unit, such as drive unit 13 in FIG. 6, reference is made to co-pending provisional application No. 60/279,087, which is incorporated by reference herein. In accordance with the system of FIG. 6, all of the drive motors in drive unit 13 are disposed away from the sterile field and thus the need for a sterile barrier is eliminated. Furthermore, since all of the motors and electronics are within a single, self-contained unit, design, testing and manufacturing of the system is greatly simplified.

Accordingly, one aspect of the present invention provides a drive unit capable of remotely driving articulation of a flexible instrument, where the drive unit is remote from the subject and the flexible instrument. The slave station of the present invention employs, to a large part, a mechanical arrangement that is effected remotely and includes mechanical cables and flexible conduits coupling to a remote motor drive unit. This provides the advantage that the instrument is purely mechanical and does not need to be contained within a sterile barrier. The instrument may be autoclaved, gas sterilized or disposed in total or in part.

In FIG. 6, drive unit 13 mechanically drives the flexible instrument (comprising shaft 30 and tool 18) through conduit 23, receiver 24 and mechanically drivable mechanism 26 (alternatively known as mechanically drivable interface or shaft mount). Conduit 23 houses a plurality of separate mechanical cables to mechanically connect drive unit 13 with receiver 24. The mechanical cables physically contact and drive the motions of shaft 30 and tool 18. Conduit 23 is engageable and disengageable with drive unit 13, i.e. attachable and detachable (see discussion of FIG. 49, below). Although two conduits 23 are depicted here, it is understood that more or fewer conduits may be used, depending on the particular application. In one embodiment, drive unit 13 comprises a plurality of motors, which drive the mechanical cables extending through conduit 23 and terminating at receiver 24. Receiver 24 interlockably receives mechanically drivable interface 26, which engages a separate set of cables extending through shaft 30 and at least one cable line operating tool 18. Thus, engaging drivable interface 26 with receiver 24 provides a mechanical (physical) connection from drive unit 13 to control certain motions of shaft 30 and tool 18. Receiver 24, which is supported by a carriage, is capable of moving along a linear path represented by the arrow 22 via rails 25.

Cables in conduit 23 also mechanically drives the translation of receiver 24 along rails 25. The rails, and thus the linear translation extend at an acute angle with respect to the operating table, as well as the subject. This angular arrangement disposes the flexible instrument system in a convenient position over the patient. This arrangement also minimizes the number of components that operate within the sterile field, as drive unit 13 is maintained at a location remote from the sterile field.

Figure 49:
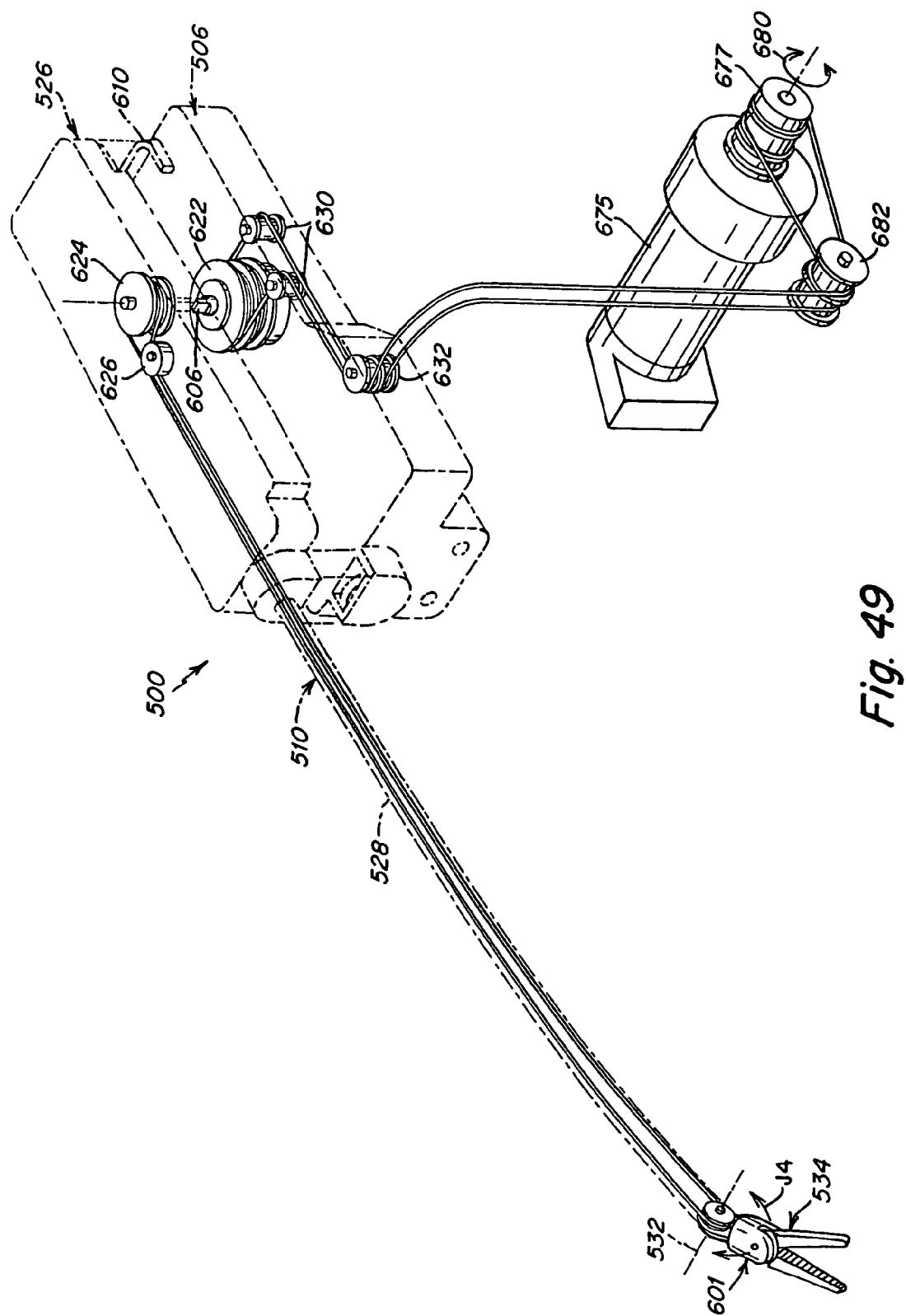
FIG. 49 is a schematic perspective view showing mechanical cabling between the drive unit and the flexible instrument system.

FIG. 49 shows a schematic perspective view of the cabling pathway for mechanically coupling one of an array of motors of a drive unit with a tool supported on a distal end of a shaft. In general, the cabling pathway comprising a plurality of mechanical cables extends from the drive unit to the receiver. Another separate set of mechanical cables connects the mechanically drivable mechanism, situated at a proximal end of the shaft, to the tool and any controlled flexible segments positioned along the shaft. Interlocking the receiver with the mechanically drivable mechanism results in connecting the two separate sets of mechanical cables, thereby extending the cabling pathway from the drive unit to the distal end of the shaft. Thus, each of the mechanically drivable mechanism and the receiver can be considered as a coupler, which interlocks or couples with each other.

More specifically, FIG. 49 shows drive motor 675 positioned within a drive unit, such as drive unit 13 of FIG. 6. The first cabling pathway comprises a set of cabling, which engages with and extends from drive motor 675 through idler pulley 682. The cables continue through idler pulleys 630 and 632 to drive wheel 622, which resides in receiver 506 (equivalent to receiver 24 of FIG. 6). A second separate set of cables extends about the drive wheel 624, guided by cam 626 and continues through flexible instrument shaft 528. Tool 534 links to shaft 528 via joint 601, which provides a wrist pivot about axis 532 in the direction of arrows J4. The two separate sets of cables are interlocked by interlocking drive wheel 622 of receiver 506 with drive wheel 624 of mechanically drivable mechanism 526 (equivalent to drivable mechanism 26 of FIG. 6). Specifically, the interlocking involves slotting a blade 606 into a corresponding slot within wheel 624 (see further discussion of FIG. 43 below).

In one embodiment, the interlocking mechanism can comprise a magnetic attachment, where a first series of magnets in the mechanically drivable mechanism interacts with a second series of magnets in the receiver. Each series of magnets can couple with the mechanical cables.

FIG. 49 also shows the output of motor 675 at a coupler pulley 677, which is adapted to rotate with an output shaft of the motor. The rotational arrow 680 indicates this rotation.

For the sake of simplicity, FIG. 49 only illustrates one cabling pathway. It can be appreciated that several other cabling pathways can be constructed and arranged to control other motions of the shaft and tool through other motors of the drive unit.

Regarding the interface 11, computer system 12 and drive unit 13, reference is also made to co-pending application PCT Serial No. PCT/US00/12553 filed May 9, 2000, and U.S. Provisional Application Ser. No. 60/279,087 filed Mar. 27, 2001, both of which are incorporated by reference herein in their entirety.

A more detailed discussion of the master station, the slave station and computation system or controller 12 is provided below.

Master Station

Figure 2:
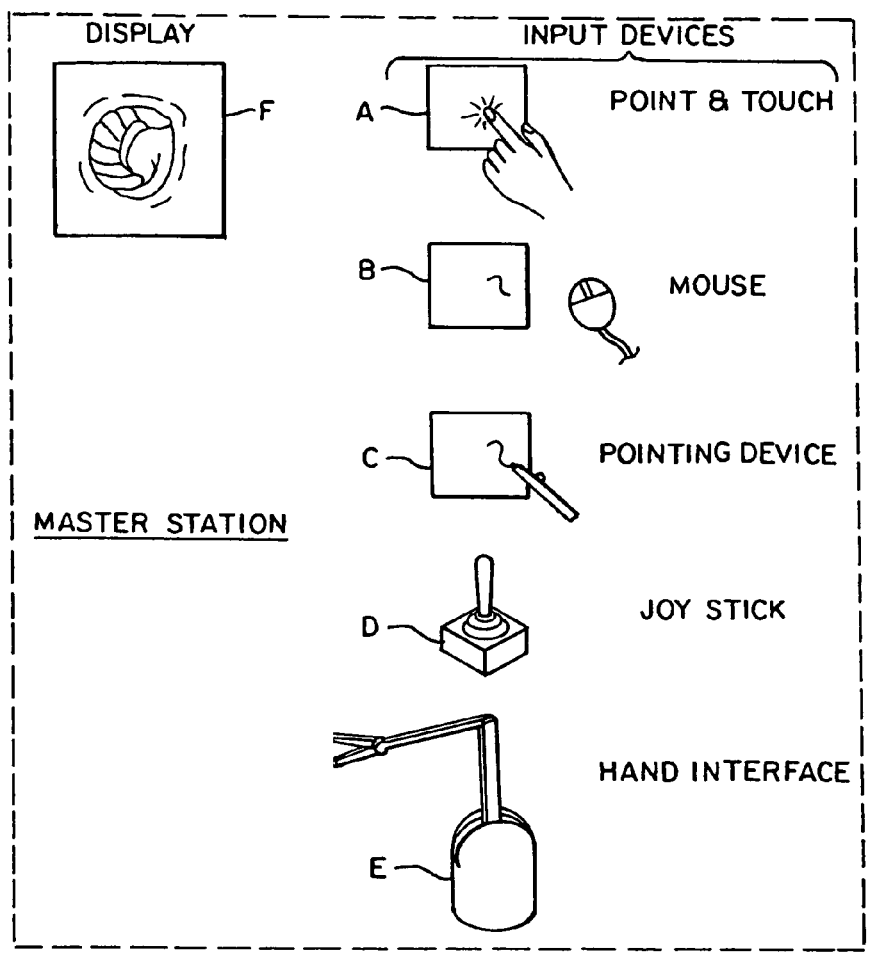
FIG. 2 illustrates further details of input devices at the master unit.

FIG. 2 schematically depicts the components of master station 1. Master station 1 can include any one or a combination of input devices A-E and a display F. Input device A is a point-and-touch device. Input device B is a computer mouse. Input device C is a pointing device that may employ a pen or stylus. Input device D is a joystick. Input device E is a hand interface, that provides finer control of the shaft, or a tool positioned at the distal end of the shaft.

In one embodiment, input device E features handles that control the motion of the shaft and a tool. Referring back to FIG. 6, the master station features input device 11 comprising handles 30A. Handles 30A are held by the surgeon, who can then torque, translate or rotate catheter member 30 and tool 18 by performing the corresponding motions on handles 30A. A rotation of a handle 30A via rotation of the surgeon's hand can control rotation of, for example, the outer shaft 32 about the co-axis. Flexing or bending of flexible section 42 can be controlled by the surgeon flexing his hand at the wrist and activating flex cable 52, as shown in FIG. 8 (see discussion of FIG. 8, below). A surgeon can manipulate tool 18 by, for example, closing and opening the jaws of handles 30A to simulate opening and closing of jaws of tool 18.

Reference may also be made to copending application Ser. No. 10/008,457, filed of even date herewith, which discloses other details of a master station input device (master positioner) that may be used in carrying out the control described herein.

Display F provides a direct video image of the site surrounding the distal end of the shaft. An endoscope supporting a camera is inserted into the body of a subject, providing the video feed of the operative site. The camera can be mounted on or housed at the distal end of the shaft. The camera can provide a view of the operative site, or may be positioned away from the site to provide additional perspective on the surgical operation.

Other detection systems may be used for providing different images useful in assisting the surgeon in performing the medical procedure. Thus, various signals may be utilized in conjunction with or in alternative to the video image, such as ultrasound (echocardiography, Doppler ultrasound), angiography, electrophysiology, radiology or magnet resonance imaging (MRI). Also, an audio signal could be used for guiding the shaft. These detection techniques can be operated with the flexible instrument of the present invention to enhance guidance of the shaft to the site as well as manipulation at the site.

In association with the input devices of FIG. 2, there are various feedback techniques can be used for feeding certain parameters sensed at the slave station back to the master station. The following are parameters that may be sensed, including but not limited to:
1. Force.
2. Position.
3. Vibration.
4. Acoustics, auditory.
5. Visual.
6. Neurological stimulus.
7. Electropotential
8. Biochemical sensing.

Controller

As discussed previously, FIG. 6 illustrates a computer system 12, which interfaces the surgeon interface 11 and drive unit 13 of the slave station. The drive unit 13 contains a series of motors that control cables coupled by way of conduit 23 to control certain movements of the catheter apparatus. The controller 12, depicted in FIG. 6 essentially links the slave station to the surgeon interface. The user input device electronically sends commands, which are translated by the controller and sent to drive unit 13. Drive unit 13 then mechanically effects the motion of the shaft, particularly the flexible segment and the tool.

Figure 14:
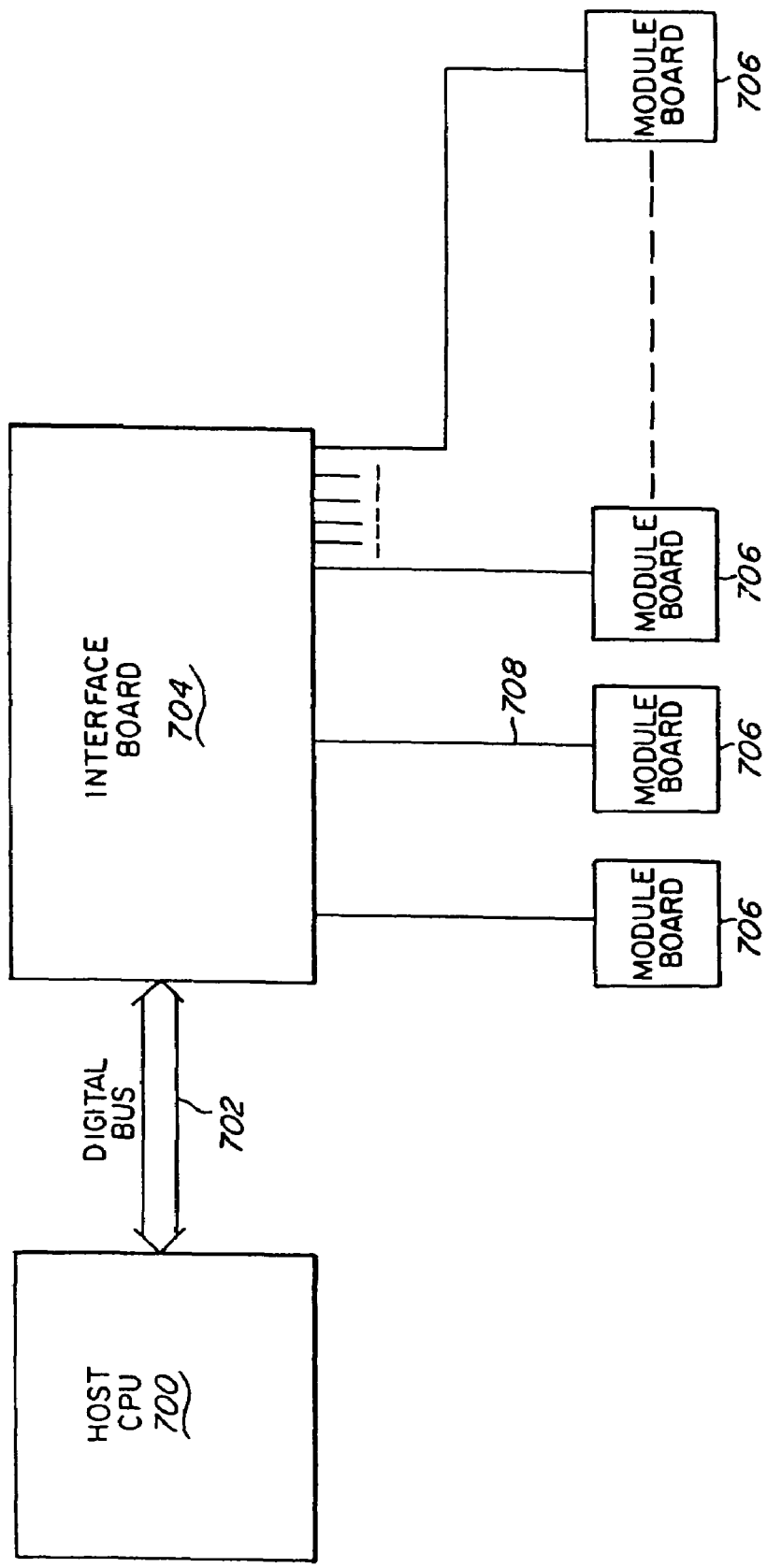
FIG. 14 is a block diagram of the controller used with the telerobotic system of this invention.
Figure 15:
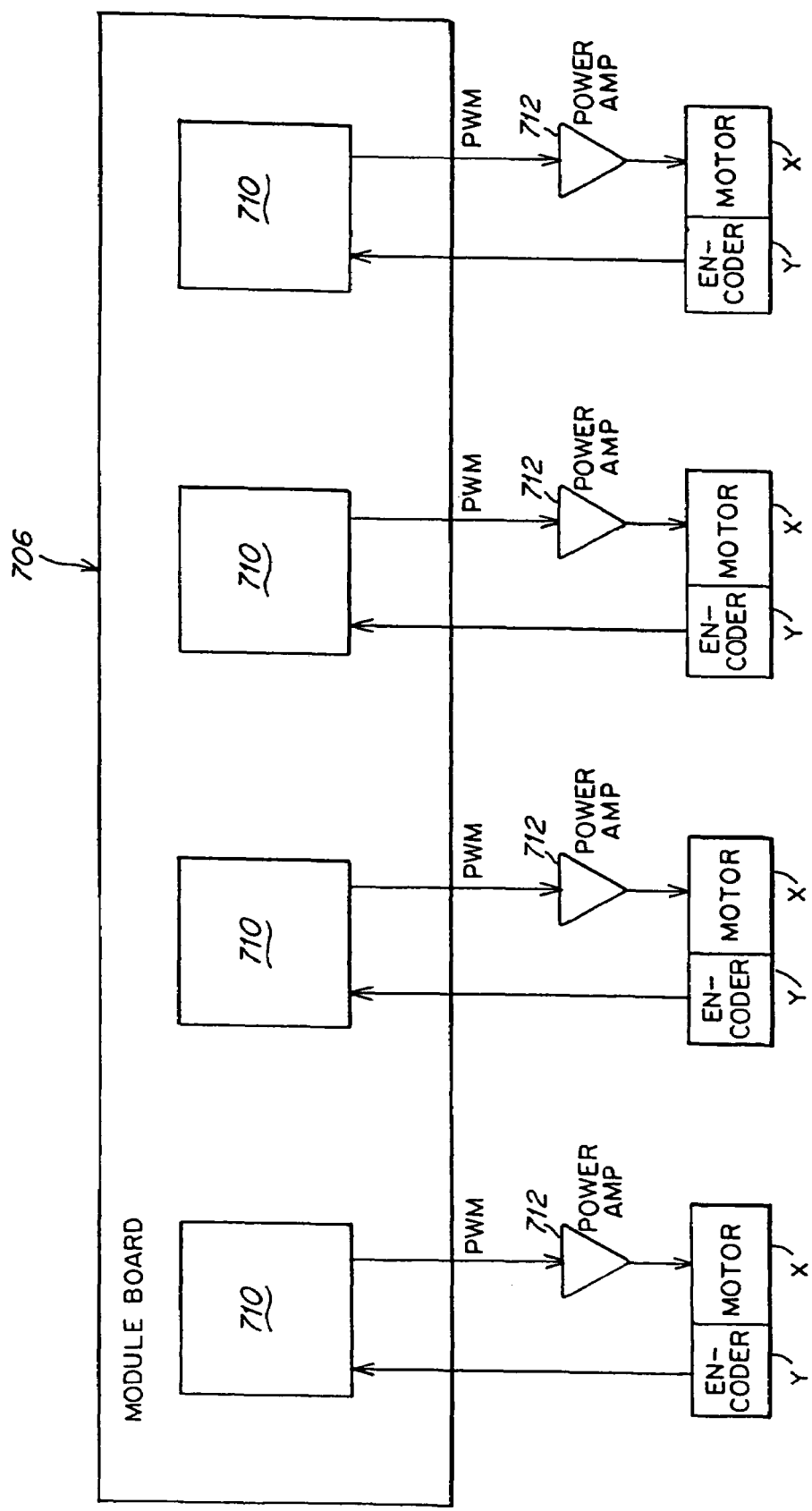
FIG. 15 is a block diagram of further details of the controller particularly details of the module board.

FIGS. 14 and 15 are block diagrams of an embodiment of a motor control system that may be employed in a drive unit of the present invention. Regarding the master station side, there is at least one position encoder associated with each of the degrees-of-motion or degrees-of-freedom. At least some of these motions are associated with a motor that may be represented by a combination of motor and encoder on a common shaft. Thus, controlling the motor ultimately controls such parameters as a force feedback to the master station. The present system can comprise a multiaxis, high performance motor control system, which can support anywhere from 8 to 64 axes simultaneously using either eight-bit parallel or pulse width modulated (PWM) signals. The motors themselves may be direct current, direct current brushless or stepper motors with a programmable digital filter/commutator. Each motor accommodates a standard incremental optical encoder.

The block diagram of FIG. 14 represents the basic components of the system. Host computer 700 is connected by digital bus 702 to interface board 704. Host computer 700 can be, for example, an Intel microprocessor based personal computer (PC) at a control station preferably running a Windows NT program communicating with the interface board 704 by way of a high-speed PCI bus 702 (5.0 KHz for eight channels to 700 Hz for 64 channels) The PC communicates with a multi-channel controller electronic card, providing up to 28 axes of motion control, each with a 1.5 kHz sampling rate. The controller is efficient, scalable and robust.

Communication cables 708 intercouple interface board 704 to eight separate module boards 706. Interface board 704 can be a conventional interface board for coupling signals between digital bus 702 and individual module boards 706. Each module board 706 includes four motion control circuits 710, as illustrated in FIG. 15. Each circuit 710 can be, for example, a Hewlett-Packard motion control integrated circuit, such as an IC identified as HCTL1100.

FIG. 15 depicts a further sub unit of this system, particularly a power amplifier sub unit 712. Power amplifier sub unit 712 is based on National Semiconductor's H-bridge power amplifier integrated circuits for providing PWM motor command signals. Power amplifier 712 is associated with each of the blocks 710, which couples to a motor X. Associated with motor X is encoder Y. Although the connections are not specifically set forth, it is understood that signals intercouple between block 710 and interface 704 as well as via bus 702 to host computer 700.

The motor control system may be implemented in two ways. In the first method the user may utilize the four types of control modes provided by the motor control sub unit 706: positional control; proportional velocity control; trapezoidal profile control; and integral velocity control. The use of any one of these modes can involve simply specifying desired positions or velocities for each motor, and necessary control actions are computed by motion control IC 710 of the motor control sub unit, thereby greatly reducing the complexity of the control system software. However, in the case where none of the onboard control modes are appropriate for the application, the user may choose the second method in which the servo motor control software is implemented at the PC control station. Appropriate voltage signal outputs for each motor are computed by the PC control station and sent to the motor control/power amplifier unit (706, 712). Even if the computation load is mostly placed on the PC control station's CPU, the use of high performance computers as well as high speed PCI bus for data transfer can overcome this problem.

Figure 16:
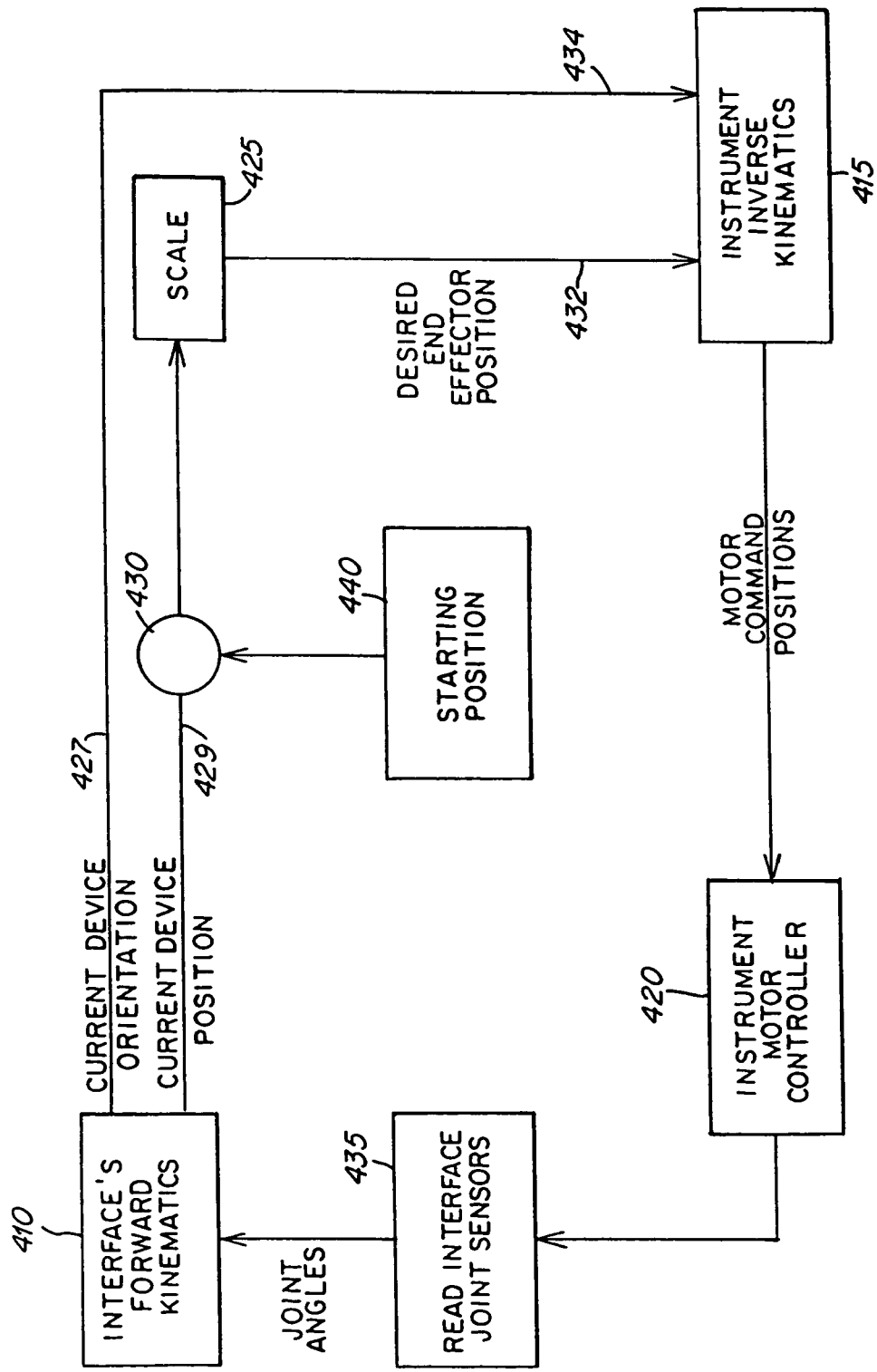
FIG. 16 is a block diagram of the control algorithm in accordance with the present invention.

FIG. 16 describes the overview of the control algorithm for the present invention, mapping out motions of the catheter to that of the surgeon's interface handle in three-dimensional space. Such precise mapping can create the feel of the tool being an extension of the surgeon's own hands. The control algorithm can assume that both the surgeon's interface as well as the catheter always starts at a predefined position and orientation, and once the system is started, it repeats a series of steps at every sampling. The predetermined positions and orientations, relate to the initial positioning at the master station.

First, the joint sensors (box 435), which are optical encoders in the present embodiment, of the surgeon's interface system are read, and via forward kinematics (box 410) computation of the interface system, the current positions (see line 429) and orientations (see line 427) of the interface handle can be performed. The translational motion of the surgeon's hand motion is scaled (box 425) whereas the orientations are kept identical, resulting in desired positions (see line 432) and orientations (see line 434) of the catheter's tool. The results are then inputted into the inverse kinematics algorithms for the catheter's tool, and finally the necessary joint angles and insertion length of the catheter system are determined. The motor controller (box 420) then commands the corresponding motors to positions such that the desired joint angles and insertion length are achieved.

FIG. 16 provides an initial start position for the handle, indicated at box 440. The output of box 440 couples to a summation device 430. The output of device 430 couples to scale box 425. Initial handle position 440 is established by first positioning the handles at the master station so as to establish an initial master station handle orientation in three dimensional space. Initial handle position 440 is then compared to the current handle position at device 430. The output from device 430 is then scaled by box 425 to provide the desired tool position on line 432 coupled to the catheter inverse kinematics box 415.

Slave Station

The slave station comprises a flexible instrument, e.g. a shaft optionally supporting a tool at its distal end, for insertion into a subject. In one embodiment, the flexible instrument is a catheter. "Catheter" as defined herein refers to a shaft adapted for, but not necessarily limited to, insertion into a subject, and more particularly for insertion into natural body lumens, canals, vessels, passageways, cavities or orifices. The shaft is typically tubular, but any elongate shaft may be adaptable for insertion into the subject. The shaft can be solid or hollow. A subject can be a human, an animal, or even individual organs or tissues that are dead or living.

The introduction of the flexible instrument into the human or animal body, may be by percutaneous or surgical access to a lumen or vessel, or by introduction through a natural orifice in the body. In this regard, examples of natural lumens include body vessels such as a blood vessel (artery, chamber of the heart or vein), urinary system vessels (renal collection ducts, calix, ureter, bladder or urethra), hepato-billiary vessels (hepatic and pancreatic ducts, chyle ducts; common or cystic duct), gastrointestinal tract (esophagus, stomach, small and large intestine, cecum and rectum), gynecological tract (cervix, uterus, fallopian tube or milk ducts and mammary canals of breast), nasopharynx (eustacean tube, sinuses, pharynx, larynx, trachea, bronchus, bronchiole, tear duct) seminal vesicle, spinal canal, or ventricles of the brain. Examples of a natural orifice include oral, rectal, nasal, otic, optic, or urethral orifices.

The shaft can be constructed from a standard 9 French (2.67 mm diameter) coronary guiding catheter.

The shaft may support various forms of tools, typically at its distal end. As depicted in FIG. 6, a user can manipulate tool 18 along a single axis of motion where tool 18 is, for example, a grasper, scissors or general mechanism (such as a stapler or clip applier). It is easily understood by those of ordinary skill in the art, however, that tools may be located at a position other than the distal end of the shaft. Preferably the tools aid in carrying out various surgical or medical procedures, including, but not limited to:

1. Grasp;
2. Cut/lyse/puncture;
3. fill/drain;
4. Secure (suture, staple, anchor);
5. Implant, i.e., any procedure that leaves an object in the body after withdrawal of the flexible instrument;
6. Remove;
7. Deliver e.g. drug/therapeutic agents;
8. Hemostasis;
9. Anastomosis;
10. Repair/reconstruct;
11. Dilate/constrict/occlude;
12. Retraction, e.g. backward or inward movement of an organ or part;
13. Coagulate;
14. Laser application;
15. Heat/cool;

Exemplary objects implanted in a subject include staples, tacks, anchors, screws, stents, sutures, and a variety of other objects implanted by physicians and medical professionals.

The procedure of delivering (procedure 7, above) can further include delivery of agents including, but not limited to:

1. Adhesives.
2. Cryonics.
3. Drugs.
4. Biologic agents.
5. Radioactive elements.
6. Bulking agents.

Furthermore, the flexible instrument can be used as a sensor. Parameters that may be sensed include, but are not limited to:

1. Force.
2. Pressure.
3. Electrophysiological signals.
4. Chemical, oxygen, Ph, blood gas.
5. Temperature.
6. Vibration.

The slave station also comprises a drive unit capable of articulating the flexible instrument, particularly the shaft and the tool. The drive unit is to drivably coupled to a receiver for receiving the mechanically drivable mechanism. In one embodiment, this coupling occurs via cables. The drive unit is electronically controllable from the master station, as there is an electronic link between the drive unit and a user input device of the master station.

When the receiver receives the mechanically drivable mechanism, the drive unit then has a direct pathway for controlling operation of the shaft and tool. If the shaft has a controlled flexible segment, the drive unit is capable of activating or bending the flexible segment via the mechanically drivable mechanism, for actuation of the shaft, the tool and positioning of the tool at an operative site within the subject. In one embodiment, drive unit is capable of bending the flexible segment via a first set of cables which couple the drive unit to the receiver, and a second set of cables which drivably couple the mechanically drivable mechanism to the flexible segment and the tool.

One aspect of the present invention provides a remote controlled outer (guide) catheter having a distal end disposed at or in an area about an operative site, preferably in the immediate area of an operative site. A coaxial inner (working) catheter nested within the outer catheter can then be used to perform the surgical or medical procedure. Previous surgical procedures involve insertion of a trocar or cannula into the subject at a relatively short depth to provide an opening for receipt of the catheter, which is then guided to the operative site. Typically the catheter is not disposed at the immediate area around the operative or target site. Thus, if the surgeon needs a second catheter, the first catheter must be withdrawn and the second catheter is guided to the target site. Such repeated insertions can aggravate trauma experienced by the patient.

The feature of the present invention, on the other hand, employs an outer catheter disposed at the target site, which allows more than one shaft to be inserted and withdrawn with minimal irritation or trauma experienced at the passageway leading to the operative site. In one embodiment, the outer catheter housing a coaxial inner catheter is disposed at the target site. The inner catheter can immediately function at the operative site. If a second inner catheter is required, the first inner catheter can be quickly withdrawn through the outer guide catheter and the second inner catheter inserted through the outer catheter with minimal injury to the subject.

Figure 3:
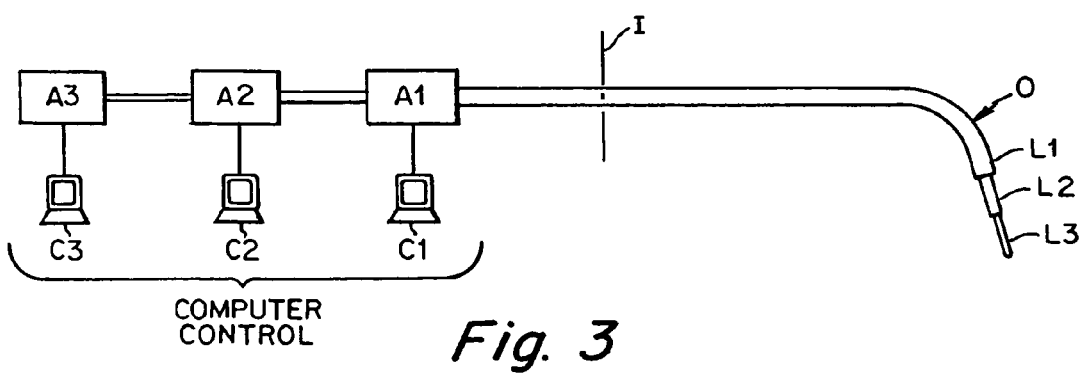
FIG. 3 is a schematic diagram illustrating one embodiment of the present invention in which the flexible instrument system includes multiple separate nested catheters.

A feature of this aspect of the present invention allows coaxial multiple shafts to be remote controlled independently of each other. FIG. 3 depicts a system of remote controlled coaxial catheters. This system employs three coaxial or nested catheters L1-L3. Dashed line I represents an incision or entry point of the patient. FIG. 3 also illustrates computer controls C1-C3, which are outside of and remote from the patient. "Remote from the patient" refers herein to any location outside the sterile field. Computer controls C1-C3 are associated with corresponding actuators A1, A2 and A3, (i.e. drive units) which in turn are associated with shafts L1-L3, respectively. Thus, in FIG. 3, for example, the controller C1 controls an actuator A1 which, in turn, controls a certain action or movement of the outer shaft L1. Those of ordinary skill in the art would readily appreciate that only one computer can be used with software capable of independently controlling actuators A1-A3. In another embodiment, shafts L1-L3 can be independently controlled by one actuator, which independently drives specific cables leading to each of shafts L1-L3. Ultimately, the present invention allows shafts L1-L3 to be remote controlled independently from each other. For example, shaft L1 can remain stationary while shaft L2 undergoes linear translations or rotations about the co-axis. The distal end of shaft L3 can also carry out these motions as well as a bend or flex independent of shafts L1 or L2. Shaft L2 can be controlled to, for example, provide a rotational movement so as to enable rotation of a distal tool. The control of a tool supported at a distal end of a shaft is independent of the motions of shafts L1-L3. Alternatively, all shafts L1-L3 can undergo a simultaneous bend or deflection at a single operative segment or flexible segment, labeled as O in FIG. 3.

FIG. 7 illustrates the outer and inner shafts. In FIG. 7, shaft 30 comprises an outer shaft 32 housing and coaxial with inner shaft 34. Outer shaft 32 and inner shaft 34 extend from and within mechanically drivable interface 26. Interface 26 mechanically couples a drive unit (shown in FIG. 6) with shaft 30. Interface 26 further comprises a series of control elements, such as pulleys 64 and 72, which run cable lines 52 and 28, and gears 60 and 68 for controlling rotation of the shafts.

The rotation of outer shaft 32 and inner shaft 34 about the co-axis can be controlled independently. Control element 60, or gear 60 in interface 26 encircles outer shaft 30 and controls the rotational position of guide shaft 32 in the direction indicated by rotational arrow 65. Gear 68 in interface 26 encircles inner shaft 34. Control element 68 controls the rotational position of the inner shaft 34 in the direction indicated by rotational arrow 69. Rotational arrows 65 and 69 indicate rotation about the "shaft lumen axis", i.e. the axis tangential to the cross section of the shaft lumen.

If a tool were supported at the distal end of inner shaft 34, control element 68 would control the rotational position of the tool about the shaft lumen axis as well. If the distal end were flexed, the shaft would curve and rotation of the shaft would cause the tool to trace a circle, and not cause the tool to rotate about its internal axis. As described below, another control can be positioned in the mechanically drivable interface for solely controlling the tool independent of the shaft controls.

Another aspect of the present invention provides a remote controlled flexible instrument capable of controlled bending, as controlled by a user at a master station. A flexible instrument comprises a shaft having at least one section that is flexible. "Flexible" refers herein to a material that is inherently and sufficiently deformable to readily pass atraumatically through a natural body lumen, cavity, vessel, orifice and the like. In one embodiment, the shaft is sufficiently flexible to readily flex and/or conform to a pathway in an anatomic vessel, lumen, cavity or the like. Non-flexible or rigid catheters can be distinguished from flexible instruments by the following test. By knowing the dimensions of a rigid catheter and the point of entry into the subject, one can calculate the position of the catheter end point inside the subject. In contrast, even if the dimensions and point of entry of a flexible shaft were known, the position of its end point within the subject cannot be calculated with precision because the flexible shaft may bend.

Flexible instruments of the present invention can also be distinguished from other known catheters that mimic bending motions solely through a series of rigid sections linked by joints. Thus, a "bend" is not the result of a deformation of the catheter material but by the pivoting or rotation of two rigid sections about a joint. In contrast, flexible instruments of the present invention include at least one flexible segment that is bendable without requiring the use of joints. The bending is remotely controlled, allowing deflection at these flexible segments away from the lumen axis of the segment. Bending in this sense is possible by choice of inherent flexibility of the instrument coupled with an induced deflection at the flexible segment. Inherent flexibility can be achieved by choice of a deformable material, such as Inherent flexibility can also be achieved by designed construction using a more rigid material, for example carving out segments of the material, i.e. slotting the material, such that the material is sufficiently thin for bending. Of course, the flexible instrument can comprise rotatable or pivotable joints, but the flexible capability is not the result of employing such joints, but by the deformability of the shaft material. In one embodiment, the bending is remotely controlled via a drive unit drivably coupled to the receiver for receiving a mechanically drivable mechanism or shaft mount. The shaft mount is then drivably coupled to the controlled flexible segment, thereby providing a drivable bending mechanism Those of ordinary skill in the art can appreciate that the shaft can be tailored for a particular body lumen. Factors of the shaft construction include resiliency of the walls of the lumen, curvature of the passageway, location of the target site, diameter of the lumen, etc. For example, a shaft for passing through a colon can be, but is not necessarily, manufactured from a material that is less deformable than a shaft for passing through a small, delicate blood vessel. Lumens that present passageways of high curvature may also require a more easily deformable, and thus more flexible, shaft than does a relatively straight lumen. Deformability of the shaft can also be tailored by varying the dimensions, particularly the diameter, of the shaft.

In this aspect of the invention, a user can controllably bend or flex at least a section of the flexible instrument. In one embodiment, this controlled bend can be provided by a shaft having at least one flexible segment, alternatively a controlled flexible segment. By manipulating controls at the master station, a user can induce a bend in the shaft at the flexible segment. Preferably, the bend at the flexible segment is actuated mechanically, thus distinguishing this aspect of the present invention from prior art catheters where the bends are induced electrically. For example, U.S. Pat. No. 5,238,005 describes a bending mechanism caused by varying the electrical resistance through a catheter material having a negative coefficient. Heating one area of a catheter by increasing its electrical resistance results in contraction of that area, causing the catheter to deflect toward the contracted area. In contrast, the present catheter responds to mechanical forces.

FIGS. 7 and 8 illustrate one embodiment of a controlled flexible segment. FIG. 7 shows controlled flexible segment 42 residing between proximal end 36 and distal end 38 of shaft 30. It is understood, however, that flexible segment 42 can be positioned on any portion of shaft 30. FIG. 8 provides an expanded view of flexible segment 42 and illustrates one construction of flexible segment 42. Here, flexible segment 42 is constructed by providing inner shaft 34 as a flexible material nested within outer shaft 32. Outer shaft 34 is split into rigid proximal and distal sections 36 and 38, both encircling inner shaft 34. Thus, flexible segment 42 is the gap between proximal and distal sections 36 and 38. Shrink-wrap pieces 44 and 45 extend over the respective facing ends of the proximal and distal shaft sections 36 and 38 and adhere these facing ends to the flexible inner shaft.

Alternatively, flexible segment 42 may be in the form of a metal coil of diameter similar to the diameter of outer shaft sections 36 and 38.

Although FIG. 8 illustrates outer shaft 32 as being rigid, it can be appreciated that outer shaft 32 can be constructed of a flexible material as well, although its flexibility is preferably less than that of inner shaft 34.

Referring to both FIGS. 7 and 8, the bending of flexible segment 42 is controlled through flex wire 52 extending from mechanically drivable mechanism 26 and through flexible segment 42, terminating at point 54 of distal end 38 (see FIG. 8). Flex wire 52 is preferably disposed between inner shaft 34 and outer shaft 32. FIG. 8 shows termination point 54 residing on the outer surface of distal end 38, although conceivably other surfaces of distal end 38 can serve as termination points. The other end wire 52 resides within drivable mechanism 26 on control pulley 64. Turning pulley 64 has the effect of pulling wire 52 in a direction parallel to shaft 30 pointing towards drivable mechanism 26. Because wire 52 is terminated at 54, this pull causes the distal shaft section 38 to deflect in a direction indicated by the arrow 55, as shown in FIG. 7.

Figure 11:
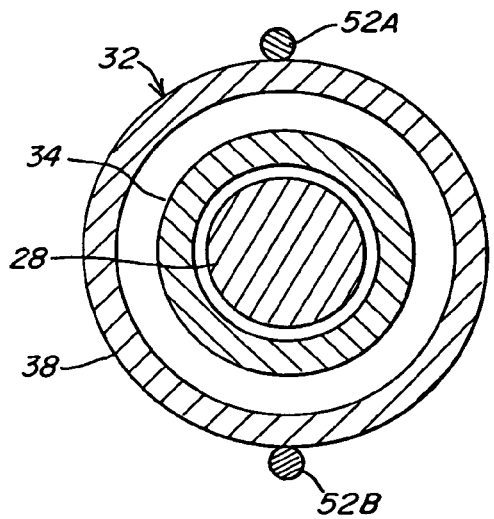
FIG. 11 is a cross-sectional view similar to that illustrated in FIG. 9 for an alternate embodiment of the invention depicting dual-direction flexing.

More than one flex wire can be spaced about the circumference of outer shaft 32 to allow bending along multiple directions different from arrow 55 yet orthogonal to shaft 30. For example, FIG. 11 illustrates an embodiment where two cables actuate bending the bending. FIG. 11 is a cross-sectional view of outer shaft 32 receiving inner shaft 34 at termination point 52. Two cables 52A and 52B terminate on outer 32 on opposite sides of distal shaft section 38. Cables 52A and 52B may be manipulated so as to deflect the distal shaft section in opposite directions, in a manner described previously. Those of ordinary skill in the art can readily appreciate that employing multiple cables results in a shaft capable of deflecting in any number of directions.

Figure 12:
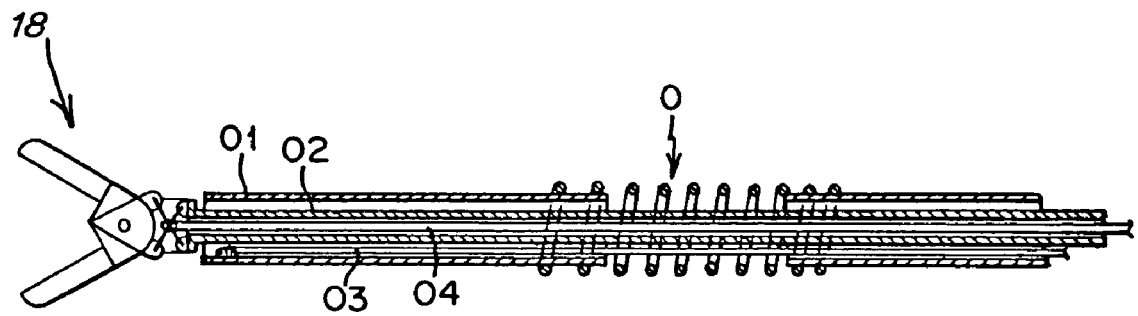
FIG. 12 is one design of tool construction in accordance with the present invention employing inner and outer catheters and inner and outer cables.

If inner shaft 34 supports a tool at its distal end, the bending motions, along with the rotation about the co-axis, serves to place the tool at any place in three-dimensional space. Another control element, i.e. pulley 72 controls cable 28, which extends through the hollow area of inner shaft 34, thereby allowing control of a specific tool operation. Depending on the complexity of the device, one or more cables leading to the tool may be required. In one embodiment, FIG. 12 depicts a distal end of shaft 30, showing operative segment O (e.g. flexible segment 42) and tool 18. FIG. 12 shows two coaxial catheters including an outer shaft O1 (such as outer shaft 32) and inner shaft O2 (such as inner shaft 34). Also disclosed are two stainless steel cables, including outer cable O3 and inner cable O4. Outer shaft O1 provides translational and rotary motion. Outer cable O3, which is disposed between outer and inner shafts O1 and O2, provides the lateral rotation (or yaw motion) of tool 18. Inner shaft O2 rotates tool 18 and inner cable O4 actuates the jaws of tool 18. The tool of FIG. 12 provides a single degree-of-freedom in order to actuate a gripper, scissors or generic mechanism (such as a stapler or clip applier). An example may be a bidirectional gripper 5 mm in length and 2.67 in diameter.

In one embodiment, the system comprising the flexible instrument comprises tool or mini-tool (18), the operative segment (42), the catheter stem (32, 34), the coupler (24, 26) comprising the mechanically drivable mechanism 26 and the receiver 24, the drive unit (13), the controller (12) and the surgeon's interface (11). The coupler provides a translational degree-of-freedom achieved by using a sliding mechanism, i.e. rails 25, onto which the coupler is mounted, as illustrated in FIG. 6. The operative or controlled flexible segment provides a number of articulations in order to position and orient tool 18. The catheter (30) has four (4) degrees-of-freedom, i.e. one translation and three rotations, as shown in FIG. 7. A fifth degree-of-freedom may be provided by the actuation of the mini-tool, as tool 18 can provide at least a single axis of motion for a grasper, scissors or general mechanism (such as a stapler or clip applier). The combination of one translation and two rotations allows the operative segment to arbitrarily position the mini-tool in three dimensional space. A final degree-of-freedom rotates the mini-tool axially.

Figure 13:
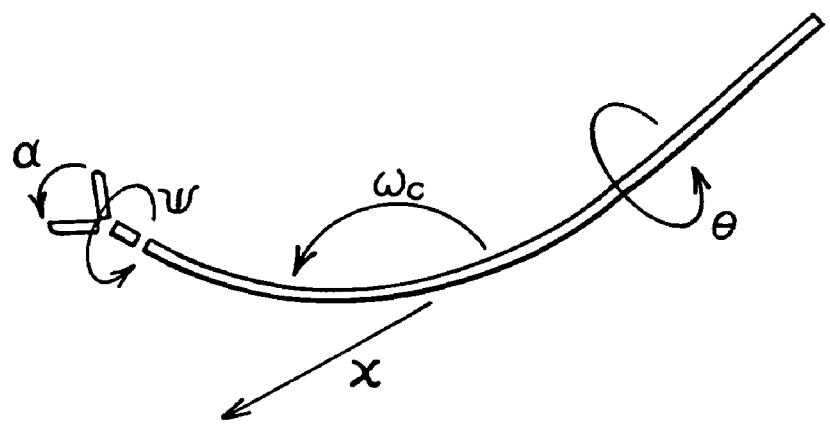
FIG. 13 is a schematic diagram of the tool or mini-tool showing certain parameters relating to position control.

The following describes the mathematical mapping of the physician's command input to the motion of the catheter system. FIG. 13 schematically illustrates the various degrees of freedom by which the catheter can be manipulated, particularly the axial and lateral rotations, or the translation motion allowing independent control of the tool position within the surgical space, as well as axial rotation of the tool. For example, the system of FIG. 6 provides a physician with seven independent command inputs, including position ($\chi_i$, $\gamma_i$, $z_i$), orientation ($\theta_i$, $\omega_i$, $\psi_i$) and tool grip angle $\alpha_i$. The controller calculates the position of the five (5) independent degrees-of-freedom of the catheter system, given by ($\chi_c$, $\theta_c$, $\omega_c$, $\psi_c$, $\alpha_c$), by determining the position (x, y, z) of the tool, given by $\chi = \chi_c + r \cos \omega_c$, $\gamma = -r \sin \omega_c \sin \theta_c$, $z = r \sin \omega_c \cos \theta_c$ $\psi = \psi_c$ $\alpha = \alpha_c$, where $\chi_c$, $\theta_c$, $\omega_c$, $\psi_c$, $\alpha_c$ are the independent inputs to the catheter system, and r is the distance from the lateral joint to tip of the mini-tool. The resulting position is $\chi_c = \chi - r \cos \psi_c$, $\theta_c = \tan^{-1}(-y/z)$, $\omega_c = \sin^{-1}(z/r \cos \theta_c)$, $\psi_c = \psi$, $\alpha_c = \alpha$. If $\lambda$ is chosen as a scaling value, the following mapping between command input and independent catheter input is $x_c = \lambda x_i - r \cos \omega_c$ $\theta_c = \tan^{-1}(-y_i/z_i)$, $\omega_c = \sin^{-1}(\lambda z_i/r \cos \theta_c)$, $\psi_c = \psi$, $\alpha_c = \alpha$. It is noted that the axial rotation and grip position are not scaled.

FIG. 42 is a perspective view of another embodiment of the slave station for a remote controlled flexible instrument. FIG. 42 depicts flexible instrument system 500 supported from support bracket 502, which extend to the operating table (see FIG. 6). Usually the support bracket is supported from the side of the operating table and may be adjustable in position relative to the operating table, to dispose system 500 in a convenient position over the patient. In one embodiment, bracket 502 is secured to the operating table at one end. The other end of bracket 502 supports the entire flexible instrument by means of a two-piece structure similar to that described in copending U.S. Provisional Application Ser. No. 60/279,087 filed Mar. 27, 2001. A knob may be provided on support base 504, not shown in FIG. 42. Once the support base 504 is fixed to the support bracket 502, then the flexible instrument system is maintained in a fixed position at base 504, providing a stable and steady structure during the medical procedure. Like FIG. 6, system 500 can be positioned at an acute angle with respect to the operating table.

Flexible instrument system 500 comprises flexible instrument 510 having a shaft 528 extending to mechanically drivable mechanism 526, which interlocks with base (or receiver) 506. Base 506 is supported on carriage 508. Carriage 508 in turn is adapted for linear translation and supported by elongated rails 512 and 514. Rails 512 and 514 terminate at one end via end piece 516, which provides further support. Support base 504 terminates rails 512 and 514 at their other end. Carriage 508 includes bearings or bushings 509 that support the carriage from rails 512 and 514.

Flexible instrument system 500 employs two separate cable bundles for mechanically driving the flexible instrument along rails 512 and 514. Pulley 521 (dotted outline), residing within carriage control module 520, receives a first pair of cables 518. Pulley 521 also receives a second set of cable (see cabling sections 513 and 515 of corresponding FIG. 43), which runs through carriage 508 to a further pulley 522 supported by end piece 516. The second set of cables controls the translational motion of carriage 508 and terminates at point 519 (see FIG. 45).

FIG. 42 also shows a set of cables 524 for driving control elements, e.g. pulleys within receiver 506. These control elements move the shaft and the tool in several degrees-of-freedom. Arrow J1 indicates the linear translation via module 520. Rotational arrow J2 indicates rotation of flexible shaft 528 of flexible instrument 510 about the inner axis parallel with the shaft length. Arrow J3 represents the flexing or bending of flexible shaft 528 at controlled flexible segment 530. In this embodiment, flexible segment 530 is positioned directly adjacent tool 534 at the distal end of shaft 528. Arrow J4 represents the pivot action of a wrist joint, which links tool 534 to shaft 528, about axis 532. In this embodiment, tool 534 is exemplified as a grasper, and arrows J5 and J6 represent the opening and closing actions of the tool jaws. Motions indicated by arrows J2-J6 are controlled from cabling 524 originating at receiver 506.

FIG. 42A provides an enlarged perspective view of the distal end of shaft 528 including flexible segment 530 and tool 534. Tool 534 comprises upper grip or jaw 602 and lower grip or jaw 603, both supported from link 601. Base 600 is affixed to or integral with flexible shaft 528. Link 601 is rotatably connected to base 600 about axis 532. A pivot pin may be provided for this connection. Upper and lower jaws 602 and 603 are rotatably connected to link 601 about axis 536 and again, a pivot pin can provide this connection.

FIG. 42A shows eight cables at 538 extending through the hollow inside of shaft 528 for control of tool 534 and flexible segment 530. Two of these cables operate the bend of flexible segment 530, two cables operate one of the jaws 602, two cables operate the other of the jaws 603 and the last two cables operate the wrist action about the axis 532. All of these cables travel through the hollow shaft 528 and through appropriate holes in flexible segment 530, e.g. wire 525, as well as holes in base 600. Each of these pairs of cables operates in concert to open and close jaws, pivot about the wrist, and bend flexible segment 530.

One pair of cables travels through shaft 528 and through appropriate holes in the base 600, wrapping around a curved surface of the link 601 and then attaching to the link. Tension on this pair of cables rotates the link 601 along with the upper and lower grips or jaws 602 and 603 about axis 532.

Two other pairs of cables also extend through the shaft 528 and through holes in the base and then pass between fixed posts 612. These posts constrain the cables to pass substantially through axis 532, which defines rotation of link 601. This construction essentially allows free rotation of link 601 with minimal length changes in the cables passing to jaws 602 and 603. Thus, the cables actuating jaws 602 and 603 are essentially decoupled from the motion of link 601 and are not effected by any rotation of link 601. Cables controlling jaw movement terminate on jaws 602 and 603. These cables permit independent operation of the jaws 602 and 603 in respective clockwise and counter clockwise directions with respect to axis 536. A similar set of cables is present on the under-side of the link 601 (not shown). Each of the jaws 602 and 603, as well as the link 601, may be constructed of metal. Alternatively, link 601 may be constructed of a hard plastic material. Base 600 may also be constructed of a plastic material and may be integral with shaft 528.

Bending of flexible segment 530 is provided via diametrically disposed slots 662, which define spaced ribs 664. Flexible segment 530 also has a longitudinally extending wall 665 through which cabling may extend, particularly for the operation of the tool. One of the pairs of cables of bundle 538 controlling flexible segment 530 terminates where base 600 intercouples with shaft 528. This pair of cables works in concert to cause bending as indicated by arrow J3, i.e. in a direction orthogonal to the pivoting provided at wrist axis 532. In FIG. 42A only one cable 525 of two is illustrated.

FIG. 43 is an exploded prospective view showing carriage 508, receiver 506 and drivable mechanism 526. Carriage 508 is adapted for motion along rails 512 and 514. Pulleys 521 and 522 receive cabling, i.e. cable sections 513 and 515, which terminate at the carriage base at point 519. Other sections of this cable extend through an elongated hole or passage within carriage 508.

Receiver 506 and drivable mechanism 526 each comprise enclosed housings supporting a plurality of control elements, such as intercouplable drivewheels and associated pulleys or cams. Inter-engaging gears 540 and 542 are supported respectively in the modules 506 and 526. A pair of cables from bundle 524 engages pulley 544 (see FIG. 45) which, in turn, drives gear 540, and which further, in turn, drives gear 542 for providing rotation of shaft 528. Collar 546 is provided at the terminus of the proximal end of shaft 528 for supporting shaft 528, which is driven by gear 542. Cabling extending through collar 546 and shaft 528 couple mechanical actions from drivable mechanism 526 through the flexible instrument shaft 528 to the distal end thereof.

Figure 46:
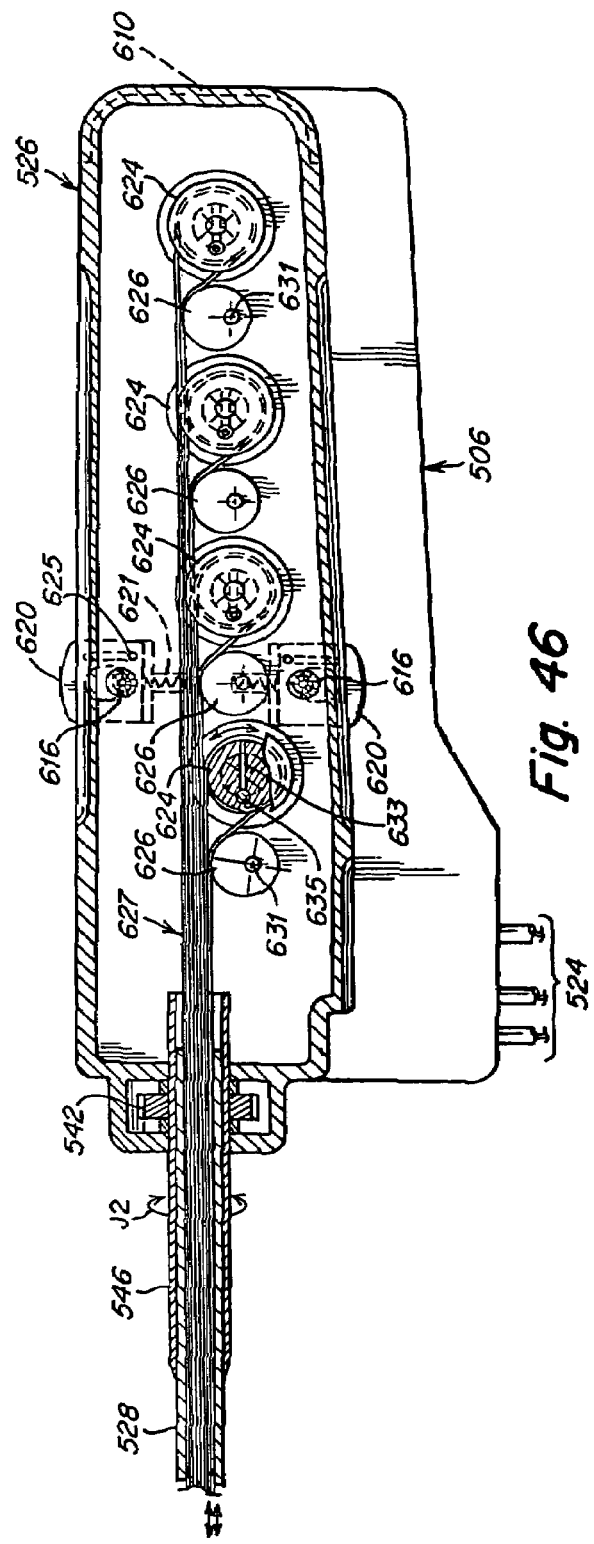
FIG. 46 is a cross-sectional plan view through the instrument module taken along line 46-46 of FIG. 45.

Drivable mechanism 526 interlocks with receiver 506, providing the mechanical connection that allows the drive unit to run cabling in flexible instrument 510. Blades 606, jutting out from the housing of receiver 506, engage with corresponding slots 608 associated with drivable mechanism 526. Projecting from the proximal end of receiver 506 is ridge 610, which is substantially U-shaped and provides another interlocking feature for mating with a similarly shaped slot 614 at the same end of drivable mechanism 526. Posts 616 protruding from the housing of receiver 506 are adapted to releasably mate with holes 618 in drivable mechanism 526. Posts 616 and holes 618 to interlock with each other, but may be released from each other via side-disposed buttons 620, as illustrated in FIG. 46. FIG. 43 also shows the cam locking screws 615.

FIG. 44 is a partial broken away rear elevational view of interlocking interfaces as seen along line 44-44 of FIG. 42. FIG. 44 shows alignment posts 616 each having a groove 617, which is engaged by the corresponding button 620. Button 620 is in the form of a plate member biased to a locked position by means of spring 621. A plate for button 620 has a keyhole slot for receiving and holding post 616 therein. Button 620, however, may be manually depressed to release posts 616 and enable ready detachment of drivable mechanism 526 from receiver 506. A retaining pin 625 may also be used to limit the travel of the button between in and out positions.

Figure 45:
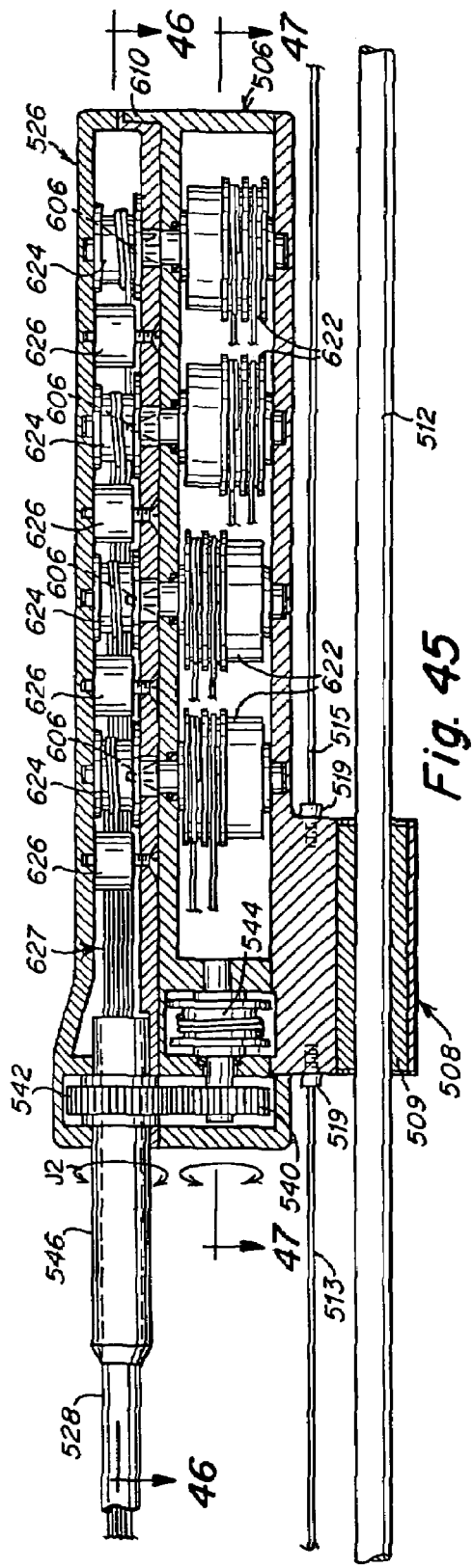
FIG. 45 is a cross-sectional side view through the interconnecting modules and as taken along line 45-45 of FIG. 42.

FIG. 45 is cross-sectional side view through the interconnecting modules taken along line 45-45 of FIG. 42. FIG. 45 shows details of drive wheels (or pulleys) in the modules 506 and 526. Four drive wheels 622 are supported within the housing of receiver 506. Drive wheels 622 receive cabling for controlling the motions of the shaft and the tool, where the cable protrudes from cable bundle 524 in FIG. 43. Each of these pairs of cables is controlled from a corresponding motor, which is part of the drive unit (see discussion of FIG. 49, below).

FIG. 45 also shows output blades 606, previously shown in FIG. 43, which extend into corresponding slots 608. These slots are disposed in respective intergaging drive wheels 624 of the drivable mechanism 526. Blades 606 have a rectangular end construction for engaging with similar rectangular slots 608 associated with the module 526. FIG. 45 also shows the gears 540 and 542 in engagement to allow drive to occur from bundle 524.

FIGS. 45 and 46 show a series of idler cams 626, one associated with each of drive wheels 624. FIG. 46 is a plan cross-sectional plan view through receiver 506 as taken along line 46-46 of FIG. 45. FIG. 46 shows the placement of cams 626. A cable wraps around each of drive wheels 624 and is held in position by its associated cam 626. FIG. 46 also shows all of the cables running parallel to each other at region 627, where the cables run from respective drive wheels 624, through collar 546 and extending down inside shaft 528 to the distal end. With the use of the placement and adjustment of cam 626, the cables are all directed in a manner to easily couple into shaft 528.

Each of cams 626 has an off-center axis 631. As viewed in FIG. 46, cam 626 may be rotated clockwise to tighten its associated cable. Rotation counterclockwise loosens the tension. Cam locking screws 615 secure cam 626 in an adjusted-to position (see FIG. 48, a cross-sectional view taken along line 48-48 of FIG. 47). FIG. 48A is a cross-sectional view taken along line 48A-48A of FIG. 48. As depicted in FIGS. 46 and 48A, the cable associated with each wheel 624 may be secured in a cable clamping hole 633 via a cable clamping screw 635. A similar clamping arrangement is associated with wheels 622. A roll pin fixes each wheel 622 to each spindle 607.

FIG. 47 is a cross sectional plan view taken through receiver 506, as taken along line 47-47 of FIG. 45. The cross-sectional view of FIG. 47 illustrates drive wheels 622 associated with receiver 506. Drive wheels 622 receive cabling from cable bundle 524. Each of a pair of idler pulleys 630 are associated with drive wheels 622. At the very input to receiver 506, idler pulleys 632 are used for directing the cable to idler pulleys 630 and from there to drive wheels 622.

FIG. 48B is a fragmentary plan view of a drive wheel engagement slot by itself as seen along line 48B-48B of FIG. 48A. The cross-sectional views of FIGS. 48A and 48B illustrate drive wheels 622 within receiver 506 having associated end blades 606. End blade 606 is a screwdriver-type blade that engages a slot previously identified as slot 608 in FIG. 43. This slot 608 is in drive wheel 624 of receiver 526. In FIG. 48B, slot 608 displays a tapered portion. The tapered portion allows easy registration of end blade 606 and slot 608, and thus easy registration between drive wheel 622 and drive wheel 624.

As described to this point, the bending or deflection of the shaft can be actuated by mechanical means such as a wire extending along a length of the shaft. Thus, actions at the distal end of shafts may be controlled by mechanical elements, such as cables, wires or other tendons.

Figure 41A:
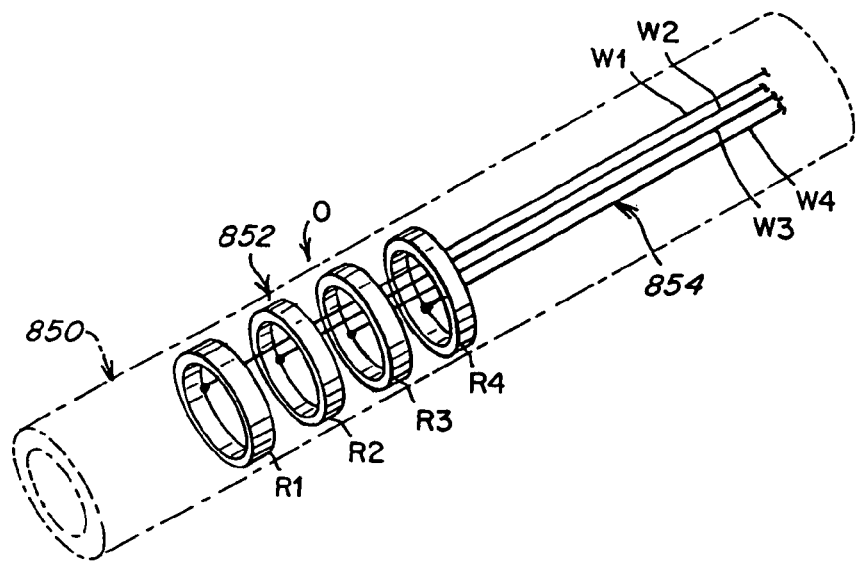
FIGS. 41A-41D depict still another form of catheter in accordance with the present invention.
Figure 41B:
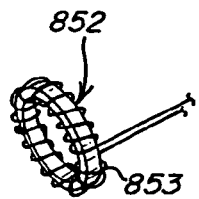
Figure 41C:
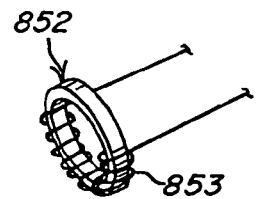
Figure 41D:
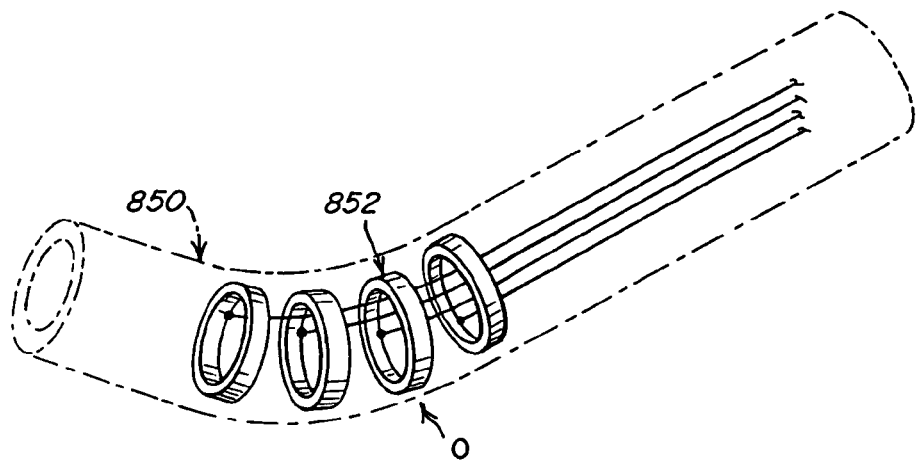

Alternatively, actuation of the controlled bending can occur by other means, such as by remote electromagnetic signal couplings. FIG. 41A illustrates shaft 850 having a central lumen. Residing in the central lumen is an operative or controlled flexible segment O, in the form of a plurality of spaced electromagnetic rings 852, separately labeled as R1, R2, R3 and R4. Each of rings R1-R4 is associated with wires 854, similarly labeled as wires W1, W2, W3 and W4. Rings 852, once energized, provide bending of shaft 850 at flexible segment O. FIGS. 41A and 41D are meant to be schematic, while FIGS. 41B and 41C are actual implementations for actuation of the rings by means of coils or windings 853. As illustrated in FIG. 41B, each ring may be electrically energized via a winding 853 associated therewith. FIG. 41B shows a fully wound winding, while FIG. 41C shows a half wound winding. Ring 852 may also have two separate half wound coils on opposite sides thereof. Wires 854 (in pairs) are selectively energized to energize windings 853 on the rings, which in turn, provide either attraction or repulsion of the rings. FIG. 41D illustrates the results of regions of rings 852 being energized to attract or repel adjacent rings. For example, a certain direction of current flow through windings 853 can create an attraction of the coils at the bottom and a repulsion of coils at the top. This cooperative action causes a bending at the operative or controlled flexible segment O.

The flexible instrument depicted in FIGS. 6 and 7 provides only the distal end as being remotely controlled. It can readily be appreciated that a controlled flexible segment may be provided, not necessarily for action at a target site, but to control certain movements of the catheter to assist in reaching a target site.

Figure 4:
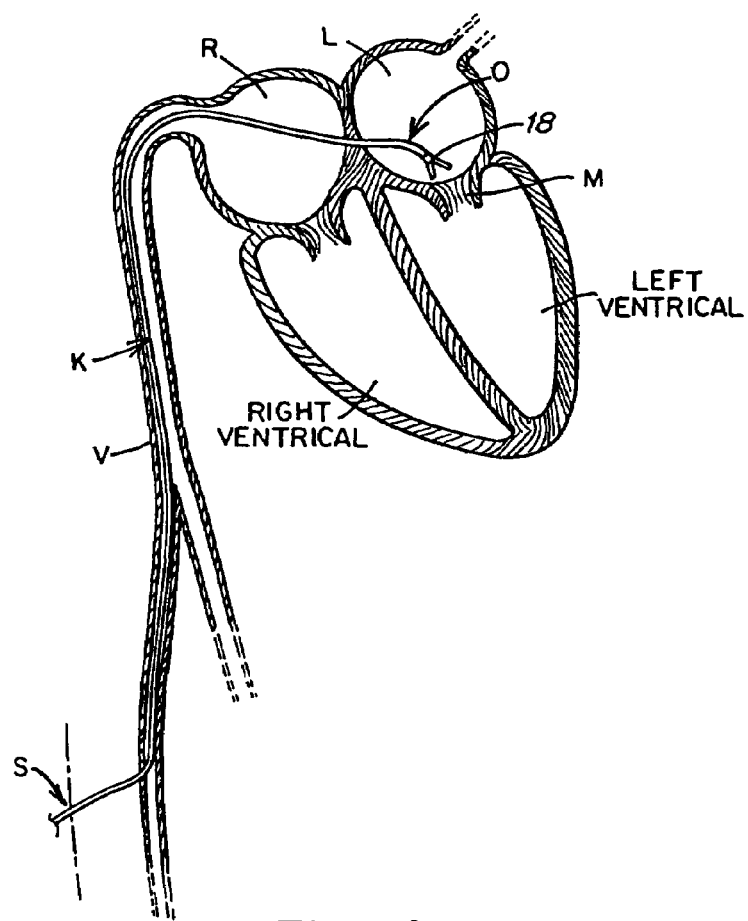
FIG. 4 is an illustrative diagram showing the use of the catheter of the present invention in connection with mitral valve repair.
Figure 5:
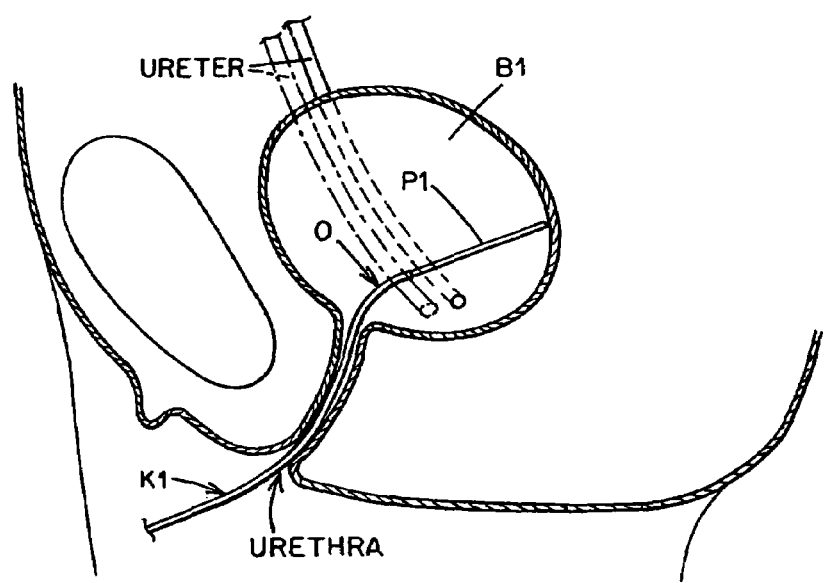
FIG. 5 is schematic diagram of the catheter system of the present invention as deployed through the urethra for a surgical procedure in the bladder.

FIGS. 4 and 5 illustrate the advantages of a flexible instrument, particularly a catheter having controlled flexibility via controlled flexible or operative segments, for use in performing a procedure or for guiding the instrument through a natural body lumen. FIG. 4 provides a schematic cross-sectional diagram, illustrating a catheter K for use in mitral valve repair, to be discussed in more detail below. FIG. 4 also shows catheter K supporting a tool 18 for carrying out certain procedures at the mitral valve annulus, also described in further detail below. In FIG. 4, catheter K is shown entering the femoral vein V by a percutaneous access at S. From the femoral vein V, catheter K must bend prior to entering the right atrium R. Catheter K then passes through a septal wall of the heart to the left atrium L, which is directly above the mitral valve M. In this particular embodiment, the operative segment of the catheter K is illustrated at O and is positioned near the very distal end of the catheter K. Thus, at the sharp, almost 90° bend prior to entering right atrium R, a user can controllably bend catheter K at the operative segment, to perform a procedure with tool 18. Also, the ability to controllably bend catheter K prevents tool 18 from conceivably being trapped within femoral vein V, causing damage to the walls of vein V. In this embodiment, it may be preferable to have at least some length of catheter K constructed of a deformable or flexible material, enabling the catheter to easily pass through the body lumen by essentially conforming to vein configurations, such as that of femoral vein V.

FIG. 5 provides a schematic cross-sectional diagram illustrating a surgical procedure where catheter K1 enters a natural body orifice, such as the urethra for carrying out procedures in, for example, the bladder. In FIG. 5 catheter K1 is shown extending into bladder B1. In this example, the computer controlled segment, identified as operative or flexible segment O in FIG. 5, is positioned at a more proximal section of catheter K1. Bladder B1, being an open cavity, does not have lumens leading from the urethra that would naturally guide a catheter towards any particular operative site. Upon entering bladder B1, catheter K1 can bend in any direction and not necessarily in the direction of the operative site. In this embodiment, because of the more proximal positioning of operative segment O, a surgeon can controllably bend the distal end of catheter K towards the operative site. In the embodiment shown in FIG. 5, the distal end of the catheter, labeled P1, can be rigid or be "passively" flexible, i.e. made of a flexible material and not necessarily controlled for flexure under remote computer control.

In the illustration of FIG. 4, the catheter K may be fed through the femoral vein by direct surgeon manipulation, in which case only the operative segment O is under computer control from a master station. Alternatively, the catheter may translate linearly through the vein under remote master station control, where the catheter can have other operative segments disposed at different locations of catheter K. Each of these operative segments can be controlled from a master station for assistance in the guiding of the catheter to a predetermined target site. Thus, the catheter may be inserted manually and also have remote computer control for at least limited linear translation.

Figure 3A:
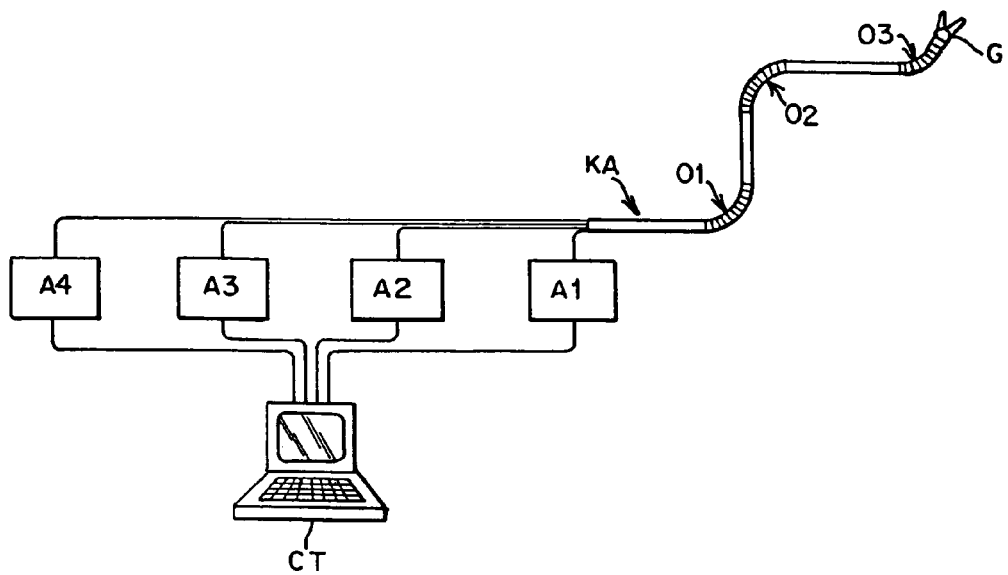
FIGS. 3A-3C illustrate different forms of catheter control in according with aspects of the present invention.
Figure 3B:
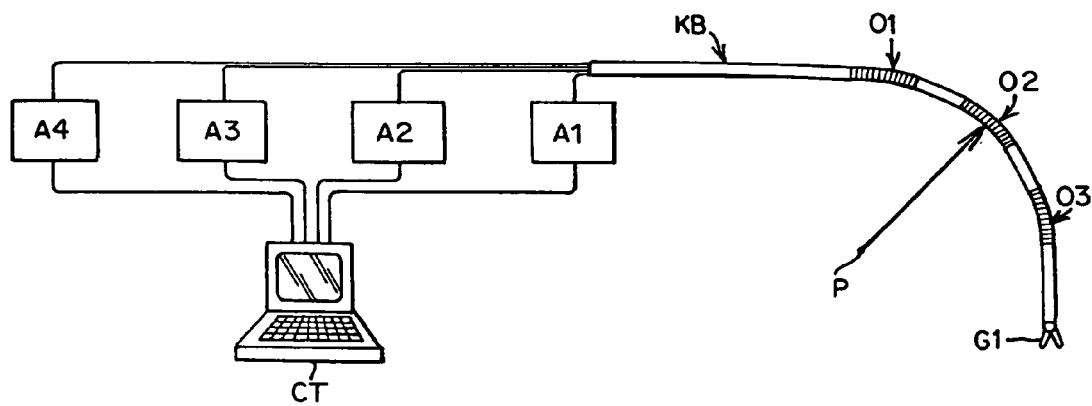
Figure 3C:
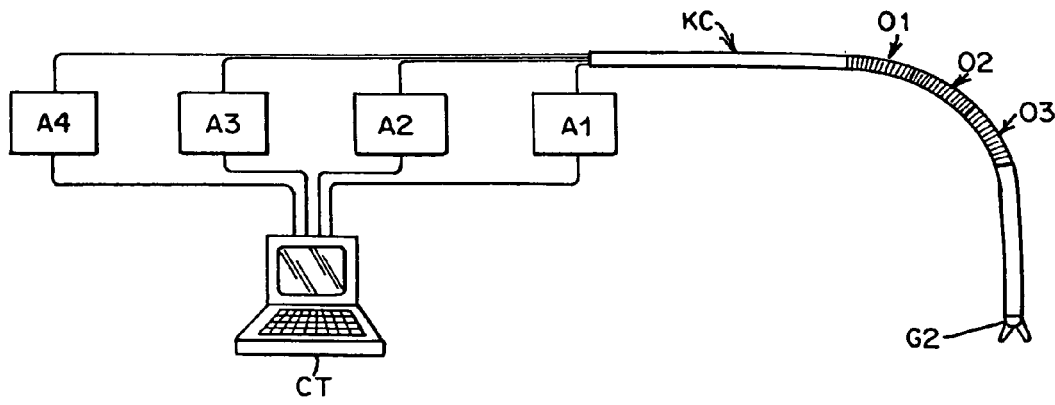

FIGS. 3A-3C show different embodiments of flexible instruments with multiple operative or controllable flexible segments. Shafts having multiple operative segments can be very useful for procedures in a body cavity, as discussed previously, but can also be useful in navigating the shaft through intricate or delicate body lumens. FIGS. 3A-3C schematically illustrate controller CT and a slave portion of the system comprising actuators or drive units A1-A4 and shaft KA, KB or KC having three operative segments O1-O3. In accordance with each of these embodiments, a surgeon inputs commands from a master station to cause certain corresponding movements of the shaft at the slave station. A surgeon's manipulations at the master station are coupled to controller CT where these manipulations are mapped to actions at operative segments O1-O3. Thus, a surgeon, at an appropriate input device, may carry out a first manipulation to control a segment O1, a second different manipulation to control the segment O2 and still a third manipulation to control the segment O3, either simultaneously or sequentially. A fourth manipulation may control the tool G.

FIG. 3A shows shaft KA having three operative segments, O1, O2, and O3, and tool G at its distal end. Actuators A1, A2 and A3 are associated respectively with operative segments O1, O2 and O3. Actuator A4 controls tool G. Each of actuators O1-O3 is controlled from controller CT. Operative segments O1, O2 and O3 are spaced a certain distance apart from each other, allowing shaft KA to simultaneously experience controlled bends. This arrangement may be necessary for lumens with multiple bends, or for hard to reach operative sites.

FIG. 3B, shows catheter KB having tool G1. In this embodiment, three operative segments O1, O2 and O3 are spaced from each other along the length of catheter KB. Segments O1-O3 can be controllably bent to form an arc having an imaginary radius point P. Thus, this arrangement of operative segments can actuate particularly acute bends. In another embodiment, catheter KC in FIG. 3C employs three operative segments O1-O3, which are contiguous. The radius of curvature can be increased.

It is understood that non-operative segments of the catheter in FIGS. 3A-3C can comprise either a flexible or a rigid material. It can be appreciated that one or more controlled flexible segments can be incorporated in the shaft, depending on the particular application.

Another aspect of the present invention provides a remote controlled flexible instrument operable within the sterile field, and disposable after use. The sterility of reusable medical instruments and implements are maintained by well-known methods such as exposure to sterile solutions and/or autoclaving. For some medical implements, it can be more cost effective to manufacture them from low cost materials and dispose them after a single use, or use on a single patient. But for certain other medical instruments, its manufacture from low cost materials still results in a costly product due to the intricate nature of the individual parts and the labor required to manufacture complex components.

It is another feature of the present invention to provide a design for a remote controlled flexible instrument having disposable components, particularly those components that are exposed to the sterile field. The present design allows the use of injection-molded plastic parts. The disposable component can be easily and quickly engaged into and disengaged from a non-disposable, reusable base. The components can be locked onto the base by snapping or interlocking matched parts, without having to thread cable wires or attach any intricate components.

One aspect of the present invention provides a disposable implement comprising a disposable mechanically drivable mechanism, a disposable shaft extending from the drivable mechanism, and optionally a disposable tool supported on a distal end of the shaft. Referring back to FIG. 7, mechanically drivable mechanism 26 comprising gears 60 and 68 and pulleys 64 and 72, can be manufactured from injection molded plastic, as well as shaft 30 extending from drivable mechanism 26. The sides of pulleys 64 and 72 feature a first semicircular planar disc stepped up from a second matching semicircular planar disc. The sides of the pulleys in receiver base 24 correspondingly match the stepped up pattern of pulleys 64 and 72. Engaging drivable mechanism 26 onto receiver 24 requires matching and interlocking the respective pulley discs. Thus, the interlocking feature in effect extends the cabling pathway from the first set of cables running from the drive unit to receiver 24, to a second separate set of disposable cables contained within drivable mechanism 26 and shaft 30. No tying or threading of cables is required to engage the disposable portion onto receiver 24.

Another design for a disposable implement is illustrated in FIG. 42. In FIG. 42, the flexible instrument 510, comprising drive mechanism 526 and shaft 528, can be a single piece disposable unit that is readily engageable and disengageable relative to the base module 506.

Disposable implement 510 may be considered as comprising a disposable, mechanically drivable mechanism such as the coupler or module 526 interconnected to a tool 534 through an elongated disposable flexible shaft or stem 528. This disposable and flexible implement is mounted so that the mechanically drivable mechanism may be connectable to and drivable from a drive mechanism, such as illustrated in FIGS. 6 and 7. In the illustrated embodiment the drive mechanism may be considered as including the coupler or module 506 and the associated drive motors. The disposable elongated flexible instrument is generally inserted into a body vessel or cavity of a subject along a selected length of the disposable elongated instrument with the elongated flexible instrument being disposable together with the disposable mechanically drivable mechanism.

The disposable implement is purely mechanical and can be constructed relatively inexpensively thus lending itself readily to being disposable. It may be difficult to make only the tool disposable, due to the intricate nature of the tool parts, which may require the user to perform intricate maneuvers and cable threading into the base of the slave station. Here, the disposable implement, i.e. the tool, shaft and drivable mechanism are manufactured as a single piece disposable unit, thus eliminating the need for intricate instrument or tool exchange procedures.

Ideally, the base of the slave station, which contacts the disposable implement, is easily cleanable. It is preferred that the disposable implement, which operates within the sterile field, experiences minimal contamination by contacting the slave station. In one embodiment of the present invention, as illustrated in FIG. 43, the interlocking drivable mechanism 526 and receiver 506 features substantially planar surface at the point of contact between the two modules. Regarding receiver 506, the planar surface is easy to clean and the inner intricate pulleys and cabling are protected from contamination by the housing. Regarding mechanically drivable mechanism 526, the housing can be made of injection-molded plastic that is simple to manufacture and is easily disposable.

One advantage of the present invention is the ease of engaging and disengaging the disposable implement. In a particular medical procedure, a multitude of instrument exchanges may be required, and the system of the present invention is readily adapted for quick and easy instrument exchange. Because the receiver is maintained in a fixed position, the surgeon can easily exchange instruments by readily decoupling at the modules 506 and 526. The ease of exchanging instruments lends to the portability of the slave station. This portable nature of the slave unit comes about by virtue of providing a relatively simple flexible instrument in combination with an adaptor (module 506, module 520, carriage 508 and associated components) for supporting the flexible instrument. Overall, the slave station is of a relatively small configuration. Because the slave unit is purely mechanical, and is decouplable from the drive unit, the operator can readily position the slave unit. Once in position, the slave unit is then secured to the support, and the mechanical cabling of the slave unit is then attachable to the drive unit. This makes the slave unit both portable and easy to position in place for use.

FIG. 49 shows an embodiment where pulley 677 is readily manually decouplable from motor 675. For this purpose pulley 677 may be a two-piece pulley arrangement comprising a coupler spindle and a coupler disk with the coupler disk secured to the output shaft of the motor. This enables the entire assembly to be disconnected at the motor so that the flexible instrument system 500 with its flexible instrument 510 may be positioned relative to the patient, independent of any coupling with the drive motors. Once the system illustrated in FIG. 42 is in place, then the coupling of the cables can be made at pulley 677 to provide drive to the flexible instrument system.

Another aspect of the present invention provides a system for repairing a cardiac valve, such as a mitral valve. Current mitral valve repair techniques, either open or minimal access, require the surgeon to place the patient on cardiopulmonary bypass and stop the heart. The left atrium is then opened and exsanguinated to allow the surgeon to perform the repair. This aspect of the present invention provides a minimally invasive mitral valve annuloplasty technique featuring the following advantages: (1) peripheral venous access; (2) the heart can continue to beat during the repair; and (3) assessment of the correction of valve incompetence in real-time using, for example, Doppler ultrasound guidance.

In one embodiment, the present cardiac valve repair system employs a guide shaft extending from a site outside a patient to an area about the cardiac valve. The guide shaft receives a flexible inner shaft for disposing a tool at the area about the cardiac valve, where the tool is supported at the distal end of the guide shaft. Preferably, the inner shaft has a relatively small diameter enabling percutaneous intravascular and endoscopic surgery. Even more preferably, the inner shaft, and optionally the guide shaft, is capable of accessing the mitral valve from the peripheral circulation, eliminating the need for incisions through the chest wall. In one embodiment, the inner shaft can have a diameter ranging from 8 to 15 French (2.5-5.0 mm). The outer catheter may be constructed from a standard 9 French coronary guide catheter, having a diameter of 2.67 mm and a wall thickness of 0.1 mm. In other embodiments, the inner catheter can have an outer diameter of 1.1 mm and an inner diameter of 0.09 mm. In yet another embodiment, the braided stainless steel cables are 0.63 mm in diameter and are capable of transmitting 178 Newtons (40 lbs. approx.).

A feature of this aspect of the present invention is that the percutaneous access to the mitral valve can be accomplished on a beating heart, eliminating the risks associated with cardiopulmonary bypass (CPB). To enable a procedure on the beating heart, preferably the procedure can be performed under physiologic conditions. The physician may monitor the procedure by, for example, transesophageal echocardiography, instead of a video image. This technique enables real-time assessment of the correction of the mitral valve regurgitation (MR) during the procedure, further enabling intra-operative provocative cardiac testing, with preload and afterload challenges and cardiac pacing all under transesophageal echo and trans-thoracic ultrasound guidance to optimize repair.

The tool can be remote controlled, as described herein, and can be designed for use in any procedure of the cardiac valve repair process. For example, a first set of tools is capable of percutaneous mitral valve annuloplasty. This represents a paradigm shift in management of disease from MIS and open surgical to intraluminal interventions. While this catheter-based intervention is described in connection with mitral annuloplasty, the technique can also be applied to other structures such as, by way of example and not limiting, the billiary tree, the genitourinary tract and intraventricular neurosurgery.

The system further includes a retainer at the area of the cardiac valve, where the retainer is attached to an annulus of the cardiac valve. As will be described in greater detail below, the retainer is closeable via the tool to draw the annulus into a smaller diameter.

In one embodiment, a trans-septal guide catheter is used to guide and support an inner catheter. The guide catheter is introduced by percutaneous access, and allows the clinician to access the left atrium via the venous circulation, i.e. through the heart wall (see FIG. 4). The guide catheter may be non-robotic, i.e. simply manipulated manually by the surgeon. Alternatively, the guide catheter may be robotically controlled from surgeon manipulations at an input device of the master station.

Once access to the left atrium is established, the inner catheter is threaded into the left atrium through the guide catheter. The inner catheter contains attachment anchors for deployment at desired points around the mitral valve annulus. A remote controlled 5-degree-of-freedom tool and wrist can be utilized to precisely reach the annulus. Ultrasound may be used to visualize the system and guide the anchor positioning and placement. This ultrasound may be transesophageal ultrasound or trans-thoracic ultrasound, for example. Furthermore, electrophysiologic signals of the heart may be used to aid in precisely locating the position of the tool at the fibrous mitral valve annulus.

There is now described a number of techniques employing the catheter apparatus of the present invention. These techniques are described herein primarily in connection with mitral valve repair.

Figure 19:
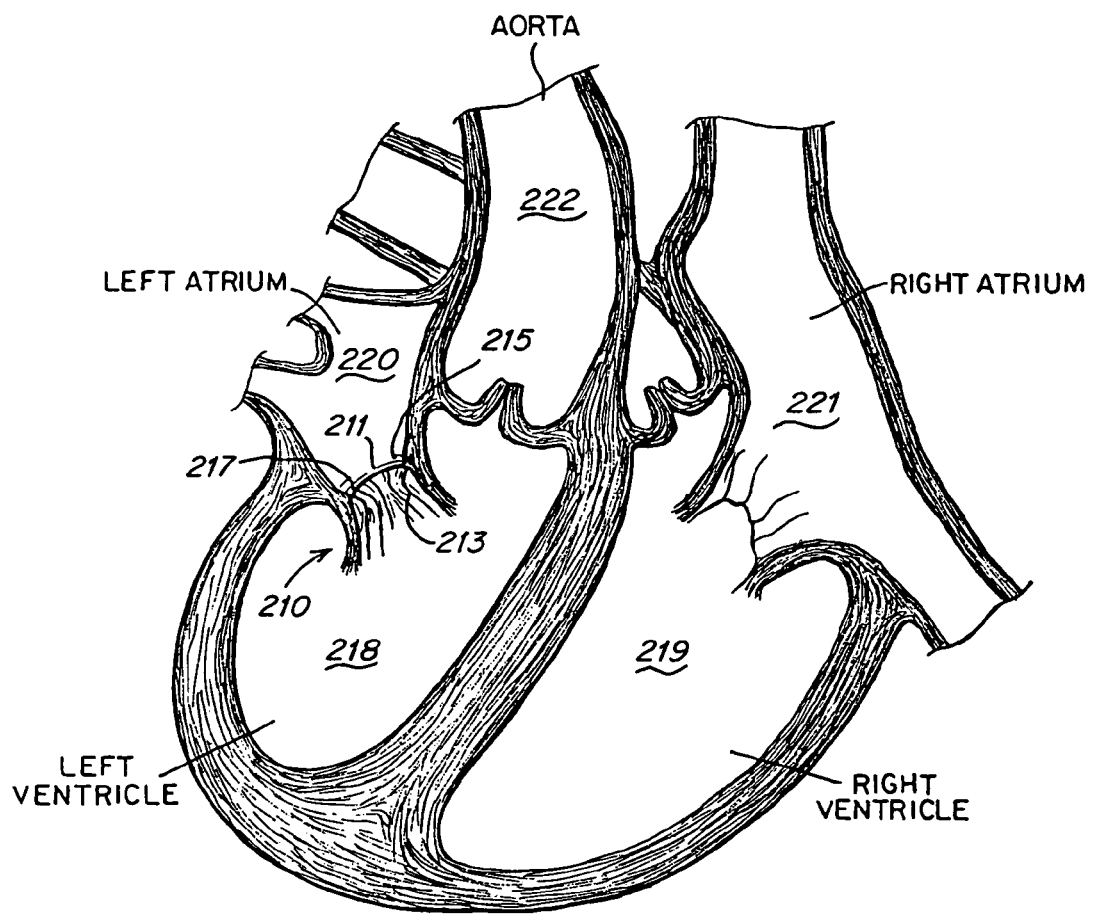
FIG. 19 is a diagram of a heart muscle illustrating the position of the mitral valve.

FIG. 19 is a schematic representation of the heart muscle showing the left ventricle 218, the right ventricle 219, the left atrium 220, the right atrium 221 and the aorta 222. Between the left atrium and the left ventricle, blood flow is from the left atrium through the mitral valve 210 to the left ventricle 218. FIG. 26 illustrates an expanded view of a mitral valve at 210 including annulus 211 and leaflets 213. FIG. 27 illustrates schematically the leaflets 213 of the mitral valve 210 with the mitral valve annulus 211. As a heart muscle ages, it is typical for the annulus of the mitral valve 210, illustrated in FIG. 19 at 211, to expand in diameter causing problems with the leaflets 213. If the leaflets fail to close properly, regurgitation may result, causing leakage by the mitral valve in the reverse direction and resulting in improper blood flow through the heart. Thus, mitral valve repair involves, at least in part, shrinking the diameter of the annulus to allow the leaflets to operate properly.

In one embodiment, threading or sewing a ring about the annulus reduces the annulus diameter, where the ring is closeable. The annulus comprises relatively tough tissue just above the top of leaflets. As viewed in FIG. 19, the opposite end of the annulus at 217 tends to expand outwardly. FIG. 19 illustrates an area at the annulus of the mitral valve (that annulus being at the top in FIG. 19) identified as trigone area 215, where the valve ring is more rigid and remains stationary. Because this area is relatively stable and rigid, it is thus difficult to contract, and most of the expansion of diameter of the ring occurs away from the trigone area. This, again, is illustrated in FIG. 20 by the positions shown in solid and in dotted outline.

Figure 20:
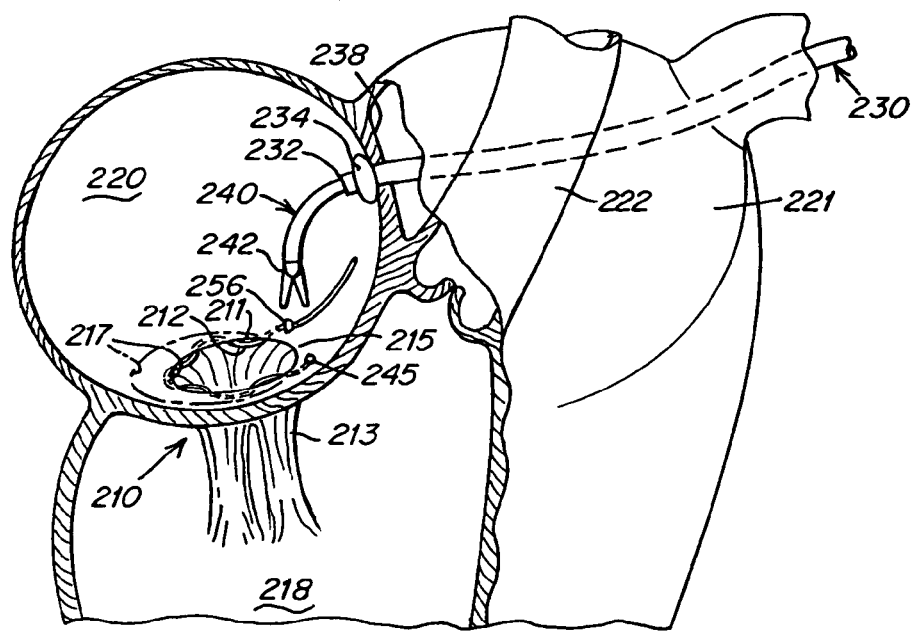
FIG. 20 illustrates further detail of the mitral valve construction as well as the catheter and tool used in the procedure.

FIG. 20 shows schematically parts of the heart such as the left atrium 220 and the left ventricle 218, with the mitral valve 210 disposed therebetween. FIG. 20 illustrates the annulus of the mitral valve in solid position, at a smaller diameter where the leaflets operate properly. The dotted outline 217 represents the expanded diameter of the base of the mitral valve, the state at which mitral valve leakage can occur.

To carry out the technique of the present invention, a guide catheter 230 is employed, such as a transseptal atrial guide catheter. The access for catheter 230 is via the vena cava to the right atrium 221. This access may be from above via the jugular vein or below by way of the femoral vein. A puncture is made in the wall 238 of the right atrium into the left atrium 220, allowing distal end 232 of catheter 230 to pass into the left atrium 220.

Figure 17:
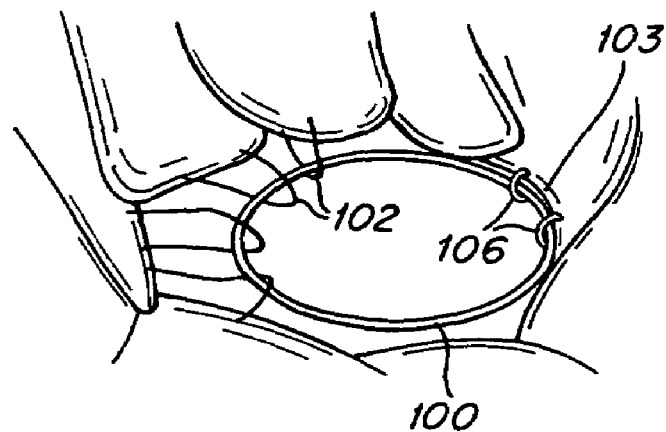
FIG. 17 is a schematic diagram illustrating one mechanism for providing mitral valve repair employing a ring mechanism.

FIG. 17 illustrates one method of shrinking the diameter of the annulus. FIG. 17 shows a metal wire ring 100 in place about the mitral valve annulus. The ring 100 may be initially secured at the trigone area 103 of the mitral valve annulus. The technique illustrated in FIG. 17 may rely upon a catheter apparatus, such as depicted in FIGS. 6 and 7 herein with an operative segment. At least limited linear translation of the catheter may be accomplished with an apparatus similar to that described in FIG. 6, although a guide catheter may also be manually inserted at least partially by the surgeon through percutaneous access via the femoral vein. The ring 100, although depicted in a ring configuration in FIG. 17, can be first inserted through the catheter in a straightened configuration. The metal wire or ring 100 is preferably constructed of a material such as Nitinol. The characteristics of this material include the ability to retain its form or to be stretched to a straight position. Once the material is passed through the catheter, it can spring back to its ring configuration. The surgeon preferably matches the configuration of the ring, particularly as to its size, to provide a proper fit for the particular mitral valve that is being repaired.

Once the straightened wire 100 has passed through the catheter, it assumes the position shown in FIG. 17. The ring, once in place, is secured to the annulus via wire clips 106 and/or sutures 102. By drawing on these sutures with the tool, the diameter of the mitral valve annulus is reduced so that it conforms to the size of the wire loop 100. As with other techniques described herein, the control is supplemented by visual considerations such as with the use of ultrasound or electrophysiological feedback.

Figure 18:
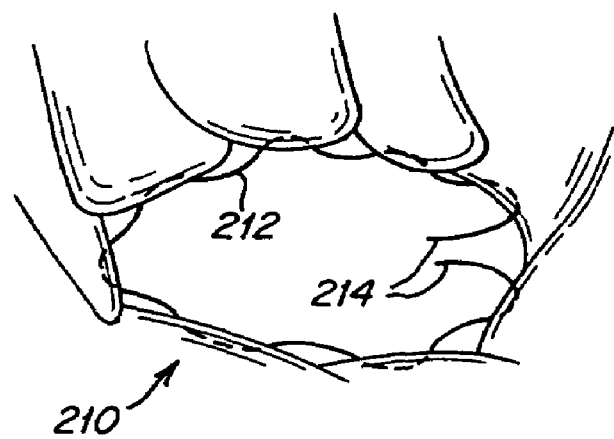
FIG. 18 illustrates schematically the concept of the present invention in connection with mitral valve repair.

FIG. 18 provides another embodiment of the present invention employing a catheter system for mitral valve repair. FIG. 18 provides a schematic representation of a ring 210 of a cardiac valve, such as a mitral valve. Fiber 212 is looped about or sewn around the annulus (base) of the valve. A number of different types of stitches may be used. The fiber may be a thread or a wire. In the embodiment of FIG. 18, the fiber is actually sewn through the annulus of the valve. After the fiber is sewn in this manner, tension is applied to ends 214 of the fiber. The tightening reduces the diameter of the ring, brings the valve leaflets into their proper position so as to avoid valve regurgitation.

FIG. 20 also illustrates a balloon 234 that may be supported at the distal end 232 of the catheter 230. Once the catheter 230 is in place, balloon 234 is inflated to further support the guide catheter in place with the end 232 extending slightly into left atrium 220. Once balloon 234 is inflated or opened, it can be snugged back against the septal wall 238 between left atrium 220 and right atrium 221. The inner diameter of the catheter 230 may be on the order of approximately 5 mm in diameter. FIG. 24 shows an enlarged view of catheter 230, with its end 232 and the associated balloon 234 holding catheter 230 in place.

As an alternate to the use of a balloon 234, a malecot 236 may be used. This is a mechanical device with expandable wings, as illustrated in FIG. 25 and associated with catheter 230 so as to hold the end 232 of the catheter in place relative to the septal wall 238.

FIG. 20 also illustrates a flexible catheter 240 with its associated tool 242 extending from the guide catheter 230. Tool 242 may be a pair of jaws operable for threading or sewing fiber. These jaws can be controlled externally at a user interface by a surgeon. With regard to flexible catheter 240, reference is made to co-pending provisional application, U.S. Ser. No. 60/269,200, as well as pending application PCT Ser. No. PCT/US00/12553, filed Nov. 16, 2000, both documents of which are hereby incorporated by reference herein.

In FIG. 23 reference is also made to the fiber 212 and an end piece 245 that is secured to one end of the fiber 212. Fiber 212 is shown sewn through wall 247. FIG. 23 also schematically illustrates the tool 242 engaging the fiber 212.

After guide catheter 230 is in place with the balloon 234 inflated to secure it in position, flexible catheter 240 is threaded through guide catheter 230 to a position just about the mitral valve, as illustrated in FIG. 20. Fiber 212 may also, at the same time, be threaded through the catheter member 230 with end piece 245 being accessible for being secured to the valve ring. As illustrated in FIG. 20, the beginning position of the threading or sewing of the fiber 212 is at a position close to or at the trigone area 215 of mitral valve 210.

After a single threading or sewing has occurred, such as in FIG. 23, then the jaws of tool 242 loop stitch the fiber 212, which may be a small but rigid wire, about the mitral valve in the manner illustrated in FIG. 18. Staples 249 may also be employed for holding the wire in place.

FIGS. 21 and 22 illustrate another embodiment to secure an end of fiber 212. In this embodiment, the end of fiber 212 is pulled so as to close the diameter of the base ring of the mitral valve. FIG. 21 illustrates guide catheter member 230 at its end 232, being held in place against the septal wall 238 by balloon 234. Flexible catheter 240 with its tool 242 has been withdrawn from catheter member 230. Double-walled structure 250 comprises coaxially arranged inner and outer tubes 252 and 254. Fiber 212 extends through these tubes and carries therealong a securing piece 256 and a retaining button 258. The inner tube 252 is adapted to engage the retaining button 258 and the outer tube 254 is adapted to engage the securing piece 256. FIG. 22 shows securing piece 256 and retaining button 258, along with the fiber 212.

Initially, once the threading through the base of the valve ring is completed, the outer tube 254 engages securing piece 256 moving it downwardly in the view of FIG. 21 while the fiber 212 is held in position. This tightens the securing piece 256 against the other side of the trigone area 215, of FIG. 20. Once the diameter of the ring has been tightened, inner tube 252 is moved downwardly to engage retaining button 258. Button 258 grabs fiber or wire 212 and at the same time retaining button 258 engages and interlocks with the securing piece 256. In this way, both ends of the threaded fiber or wire 212 are secured roughly at the positions illustrated in FIG. 20. The pulled fiber 212 causes the mitral valve ring to draw into a smaller diameter such as the position shown in solid, rather than the in-dotted position of FIG. 20.

Once the securing piece and the retaining button are firmly held to the wire 212, then the member 250 may be withdrawn through the guide catheter 230. The flexible catheter member 240 may then be reinserted with a different tool such as a pair of scissors for cutting the exposed end of the fiber 212.

Another possible technique for reducing the annular diameter involves a loop of cable that extends through hooks or anchors placed in the annulus, as illustrated in FIG. 29. FIG. 29 shows the cable or wire 120 and schematically illustrates the anchors at 125. In this technique the valve is reduced through a "lasso" technique, in which the cable exerts an equal force on all of the anchors. This technique uses an articulate catheter preferably inserted through a guide catheter, such as illustrated hereinbefore, to place the anchors one at a time into the mitral valve annulus. The cable onto which the anchors are suspended provides the closing force when tensioned by the operator.

In one embodiment, the flexible instrument comprises a guide catheter 150, as illustrated in the diagram of FIG. 30. Inner catheter 155 houses an anchor and cable system depicted generally at 160, including tensioning cable 162 and anchors 164. Five degrees-of-freedom are provided: (1) rotary, (2) linear, (3) flexure motion with regard to the guide catheter 150 as well as (4) linear and (5) rotary motion with regard to the inner catheter 155.

Guide catheter 150 may be approximately 8 French in diameter with a computer controlled flexible end portion, illustrated in FIG. 30 as operative segment O. A computer controls three degrees-of-freedom with regard to the guide catheter 150, along with two degrees-of-freedom of inner catheter 155. Refer to FIG. 30 and the corresponding motions F1-F5.

FIG. 30 depicts anchors 164 as having a loop and two legs, although other anchor designs can be readily contemplated. The legs of each anchor 164 may curl outwards. Once anchors 164 are deployed from the constraint of the inner catheter, they curl outwardly. The curling motion of the anchor legs secures them to the fibrous tissue of the mitral valve annulus. Preferably the anchors are fabricated from a super-elastic material such as Nitinol.

A tensioning cable, such as the cable or wire 162 illustrated in FIG. 30 may pass through each of the loops of the anchor. This allows an equal force to be placed on each anchor and prevents the anchors from becoming loose in the bloodstream. The tensioning cable passes back through the robot inner catheter and out of the patient. The final tension is adjusted manually by the surgeon (or by computer) to optimize the annular size under direct visualization. Also, within the inner catheter is preferably disposed a deployment wire used to advance and fire the anchors into the annulus wall.

FIGS. 30A and 30B depict a cable termination tool set. This set comprises two catheters used to: (1) crimp the end of the tether cable once the tension is placed on the annulus; and (2) cut off the remaining cable at the end of the procedure. Both of these catheters may use a four-bar linkage or other system.

FIG. 30A shows a crimp tool 172 having a pair of jaws 174 that can be used to crimp member 176 about the tether cable 170. Thus, the first catheter 172, which may be referred to as a cable crimper, holds the crimp element 176 in the jaws 174 with the tether cable 170 pre-threaded through the crimp element and catheter shaft. The tensioning of the cable may be performed under ultrasound guidance. Although one tether cable 170 is shown in FIG. 30A, opposite ends of the tether that come from the mitral valve site preferably extend through the crimp element 176. Once the tether cable is tensioned, so as to bring the mitral valve into its proper diameter, then the crimp element 176 is actuated by the cable crimper 172 illustrated in FIG. 30A. Once the proper tension is achieved, the crimper is actuated by applying tension on the push-pull drive cable 175 and by closing the crimp element at the jaws 174 so that the crimp element crimps the tether cable 170 in the proper position and at the proper tension.

After the crimping or securing step, then the cable crimper is removed and the cutting catheter 182 is introduced as also illustrated in FIG. 30B. This catheter is also introduced over the tether cable 170 and through the guide catheter. It is advanced up to the crimp, and severs the cable with its jaws 184 by tensioning the push-pull drive cable 185. The procedure is now completed and the system catheters are then removed.

As indicated previously, the proximal end of the catheter is comprised of a disposable coupling mechanism that engages a drive mechanism, such as is shown in FIGS. 6 and 7. For this purpose, the coupler, identified in FIGS. 6 and 7 as couplers 24 and 26 are adapted for disengagement therebetween. One coupler section may be considered as transmitting motion to the guide catheter while the other coupler section may be considered as transmitting motion to the inner catheter and the drive cable. This involves the mechanical coupling of the guide catheter with the coupler so that actions of the guide catheter are controllable from the mechanical control elements of the coupler.

In one embodiment, a drive unit is coupled with the inner shaft and the guide shaft independently, the drive unit capable of independently effecting movement of each shaft to at least one degree of freedom.

For each coupler element, rotary disks transmit motion from the remotely controlled drive system to the catheter articulations. By way of example, in a first coupler element, a horizontal disk may drive the distal flexure. Another element may include disks, which control the axial and/or rotary positions of the inner catheter and, for example, the advance of the anchors. All of the coupling elements are mounted on a slider or sliders, which allows independent control of the linear advance of the outer and inner catheters. Again, refer to FIGS. 6 and 7. The catheter system including the inner and outer portions, as well as the proximal coupling element are disposable and mount removably to the drive member.

In accordance with the technique, such as described in FIG. 29, when the last anchor is in place, the inner robot catheter and deployment wire are removed. The physician can manually (or under computer control) adjust the tension in the cable and thus the diameter of the mitral valve after the first element of the cable termination system is threaded over the cable and through the robot guide catheter. Since this procedure is performed on a beating heart, the annular size can be optimized under direct ultrasound guidance. Once the mitral valve annulus has been precisely adjusted, a cable termination system, such as the one depicted in FIGS. 30A and 30B, clamps and cuts the cable. This completes the mitral valve repair procedure.

Another feature of the present invention provides a system for closing the base of a cardiac valve, such as a mitral valve. The closing can occur primarily by a stapling technique in which staples are attached to the valve ring or annulus to draw the annulus into a smaller diameter. In this way the leaflets are then more appropriately positioned for opening and closing.

Figure 31:
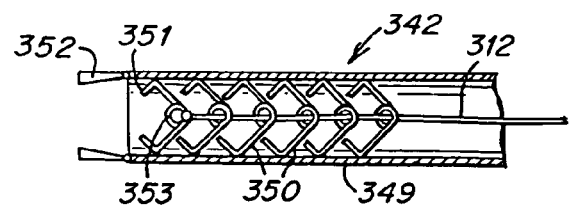
FIG. 31 illustrates a staple array of the present invention.

FIG. 31 illustrates a staple array comprising delivery system 342 including storage housing 349 for a plurality of staples 350. Each of staples 350 is a surgical staple movably mounted within housing 349. Cable or wire 312 interconnects and loops through each of staples 350. Each staple 350 includes a pair of pointed ends 351 and center loop 353. The staple 350 at the most distal end of housing 351 (i.e. nearest the exit of housing 351) has cable 312 attached fixedly at loop 353, to prevent losing staples in the subject. For the remaining staples, cable or wire 312 freely loops through center loop 353. A release mechanism, not illustrated in FIG. 31, but which may be a standard design, can be used to move staples 350, one at a time, out of the housing 349. FIG. 31 also schematically illustrates a clamping mechanism 352 at the distal end of housing 349, for closing each of staples 350 as they exit housing 349.

Figure 32:
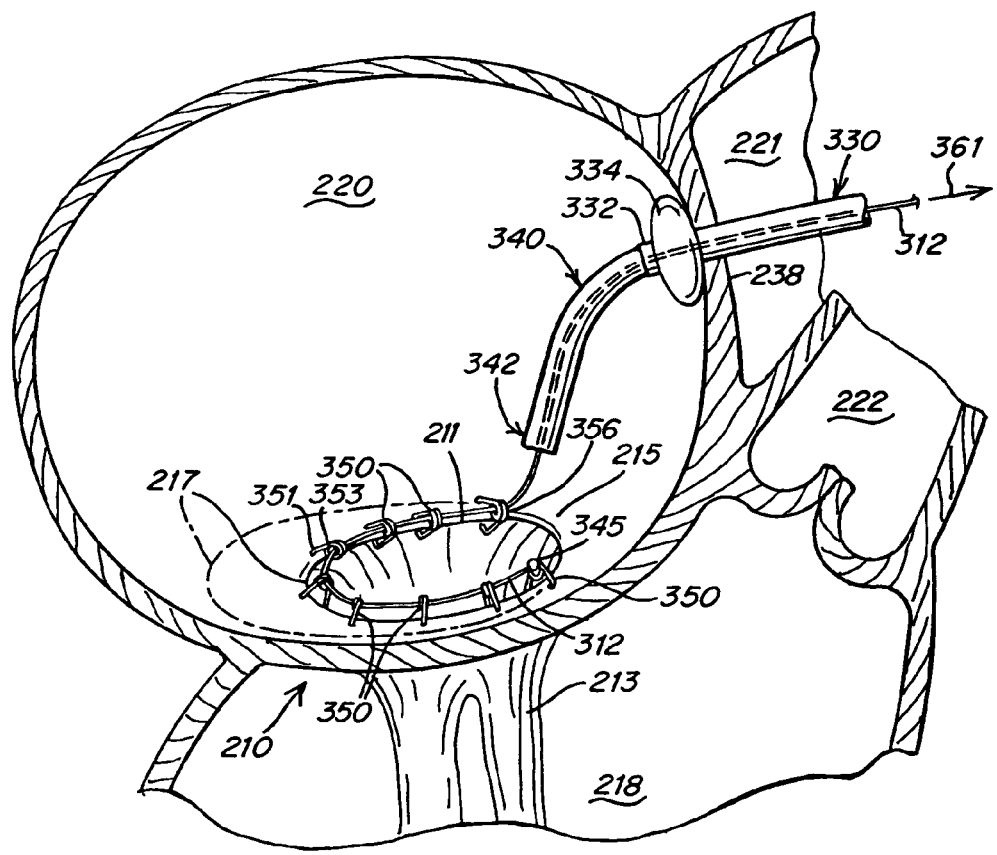
FIG. 32 illustrates the mitral valve construction as well as the staple apparatus and technique of the present invention.

FIG. 32 illustrates another method for repairing a mitral valve, featuring the use of staples to secure a ring to the mitral valve annulus. As will be described in further detail, a tether cable or filament is threaded through an array of staples or anchors via a first inner catheter. Once the attachment anchors are placed around the annulus, the first inner catheter is removed and a second inner catheter is disposed in the guide catheter. This second inner catheter allows the clinician to apply tension to the cable to reduce the mitral valve annulus circumference, in effect, pulling on a lasso. The annuloplasty is monitored by real-time echocardiographic quantitation of regurgitant flow attenuation, with and without after-load reduction. The clinician monitors the cardiac physiology for resolution of regurgitation. When the hemodynamics are optimized, still a further inner catheter device may be used so as to place a stop or crimp on the cable. Still another inner catheter device may be used to cut the cable. These latter two inner catheter devices may be robotic or non-robotic catheters.

FIG. 32 features mitral valve 210 with trigone area 215. Guide catheter 330 accesses the vena cava and passes to the right atrium 221. This access may be from above via the jugular vein or below by way of the femoral vein. A puncture is made in septal wall 238 separating right atrium 221 from left atrium 220, allowing distal end 332 of guide catheter 330 to access left atrium 220.

Balloon 334 may be supported at distal end 332 of guide catheter 330. Once guide catheter 330 is positioned at a desired location, balloon 334 is inflated to secure guide catheter 330 to the wall with end 332 extending into the left atrium. Once balloon 334 is inflated, it can be snugged back against the septal wall between left atrium 220 and right atrium 221. The inner diameter of the catheter 330 may be on the order of approximately 5 mm in diameter. As an alternative to balloon 334, a malecot may be used, i.e. a mechanical device having expandable wings capable of securing catheter 330 against septal wall 238.

Guide catheter 330 coaxially nests flexible catheter 340 and its associated staple delivery system 342. With regard to this catheter construction, reference is made to a co-pending provisional application Ser. No. 60/269,200 filed Feb. 15, 2001, as well as pending application PCT serial number PCT/US00/12553, filed Nov. 16, 2000, both of which are incorporated by reference herein in their entirety.

After balloon 334 is inflated to secure guide catheter 330 in position, flexible inner catheter 340 is threaded through guide catheter 330 to a position just above mitral valve 210, as illustrated in FIG. 32. Delivery system 342, associated with inner catheter 340, also passes through catheter 330, holding fiber 312 and staples 350 to an area about the mitral valve.

FIG. 32 also illustrates fiber 312 tracing a circumference about annulus 211, terminating at two end locations 345 and 356. The area traced by fiber 312 and where the stapling occurs is at a ring of relatively tough tissue just above the top of leaflet 213. The area not traced by fiber 312 is valve trigone area 215, which is relatively fixed and not easily contracted. Thus, the repair of the mitral valve, involving decreasing diameter 217 from dotted line to solid line, occurs away from trigone area 215.

Flexible catheter 340 is manipulated to cause a stapling about annulus 211 of mitral valve 210. The releasing of each staple is controlled by a mechanism preferably within flexible catheter 340 and operable from a user interface station remote from the subject. Once all of the stapling has occurred, wire 312 is pulled in the direction of arrow 361 in FIG. 32. This pulling causes a closure of valve annulus 211, as desired. Once the clinician is satisfied that the repair is complete, the cable 312 is then locked off with a crimp, such as illustrated at 365 in FIG. 33. This crimp may be facilitated by the insertion of a different catheter member 340 within the catheter 330, all while the cable 312 is held in the proper cinched-down position.

A plurality of staples 350 having loops 353 encircling fiber 312, secures fiber 312 to the annulus of the mitral valve, terminating at points 345 and 356. The procedure of looping fiber 312 and stapling can be performed via remote control from a master station under surgeon control with multiple degrees-of-freedom of the tool so as to accurately locate the implant fiber 312 and staples 350.

Fiber 312 is fixedly secured to end staple 350 at point 345. The remaining staples are free to glide along fiber 312. When all the staples are secured about the annulus, fiber 312 may be cinched down under ultrasonic guidance, watching for a reduction or elimination of the valve regurgitation. Once adequate tension has been placed on the cable 312, tension can be maintained without disengaging the closure system. This allows the clinician to monitor the patient for some period of time to confirm that the repair has taken place. Once the clinician is satisfied with the repair, the cable can be locked off with a crimp or by some other technique and the cable may then be cut.

Another feature of the present invention is that the technique can be performed under physiologic conditions. The physician can monitor the procedure by, for example, transesophageal echocardiography, instead of a video image. The aforementioned "lasso" technique enables real-time assessment of the correction of the mitral valve regurgitation (MR) as the "lasso" is tightened. This enables performance of intra-operative provocative cardiac testing, with preload and afterload challenges and cardiac pacing all under trans-esophageal echo and trans-thoracic ultrasound guidance to optimize repair.

Figure 33:
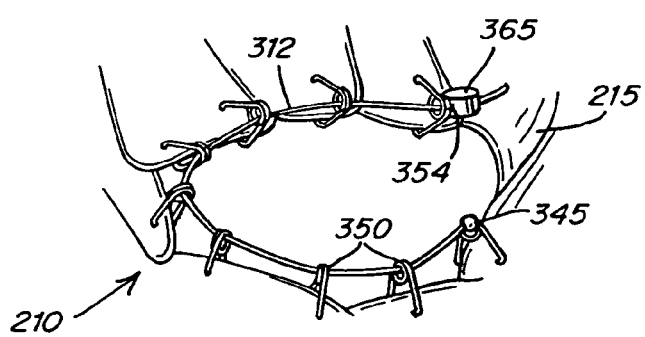
FIG. 33 is an illustration of the staple array when applied and secured to the valve annulus.

FIG. 33 illustrates an expanded view of the finished repair region. A staple 350 is fixedly attached to fiber 312 at position 345. Pulling cable 312 through various loops 353 of staples 350 causes pulling of the annulus into a smaller diameter, thus closing the valve from an initially larger diameter, dotted outline 217, to a smaller diameter, solid outline in FIG. 32 at 217.

Figure 34:
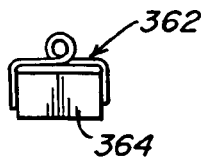
FIG. 34 is a schematic illustration of an alternate embodiment for the staple array.

An alternate embodiment of a staple is illustrated in FIG. 34. Staple 362 may be an elastic-like staple, such as a nitinol staple. Staple 362 is normally biased to a closed position. A delivery system employs rod 364, or the like, to hold staple 362 open. As the rod is moved longitudinally to the array, each staple in sequence is sprung closed. Such an arrangement would avoid the necessity of a clamping mechanism 352 as illustrated in FIG. 31.

Figure 35A:
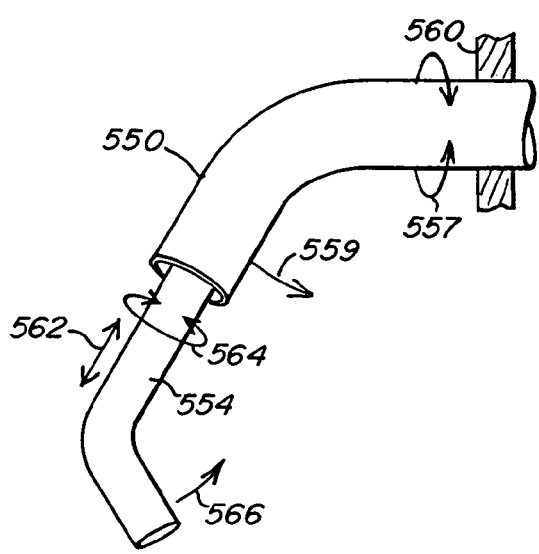
FIGS. 35A and 35B illustrate another version of the invention wherein the guide catheter is robotic.
Figure 35B:
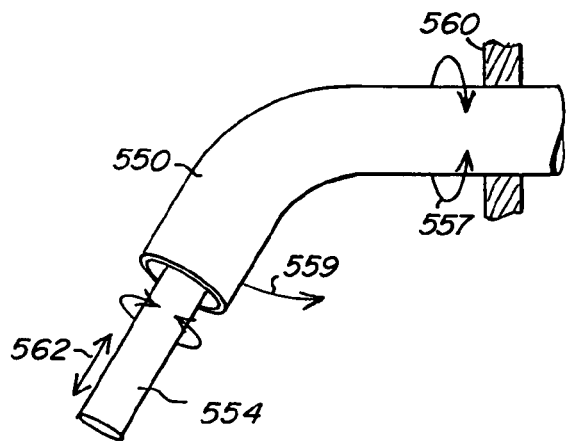

FIGS. 35A and 35B illustrate other embodiments of an outer catheter 550 and an inner catheter 554 extending through septal wall 560. These embodiments illustrate the outer (guide) catheter as a robotic catheter. It is understood that the instrument embodiments of FIGS. 20 and 32 may also encompass systems where the guide shaft is robotic. In FIG. 30, the guide catheter is also robotic. In FIGS. 35A and 35B, arrow 557 indicates rotation of outer catheter 550, and arrow 559 indicates flexing of outer catheter 550. In FIGS. 35A and 35B, inner catheter 554 can experience linear motion along the co-axis (arrow 562) and rotational motion (arrow 564). The outer catheter 550 may also be capable of independent linear translation. FIG. 35A illustrates inner catheter 554 as being capable of a controlled flex or bend, i.e. inner catheter 554 has a controlled flexible segment. Thus, the inner catheter of FIG. 35A is capable of deflecting in the direction of arrow 566.

Figure 38:
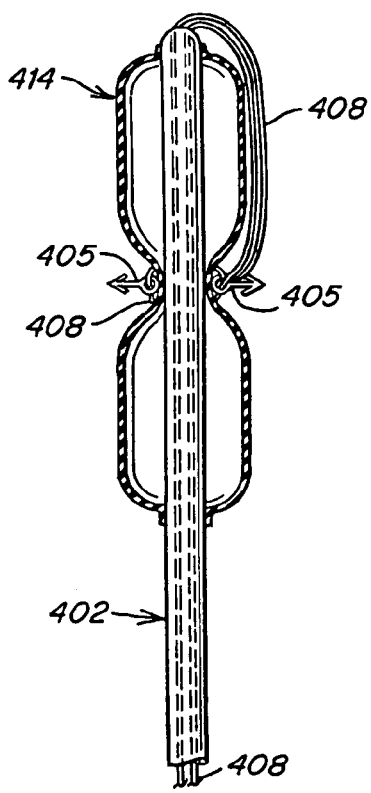
FIG. 38 illustrates another version in accordance with the invention employing a balloon with the balloon in a deflated state.
Figure 39:
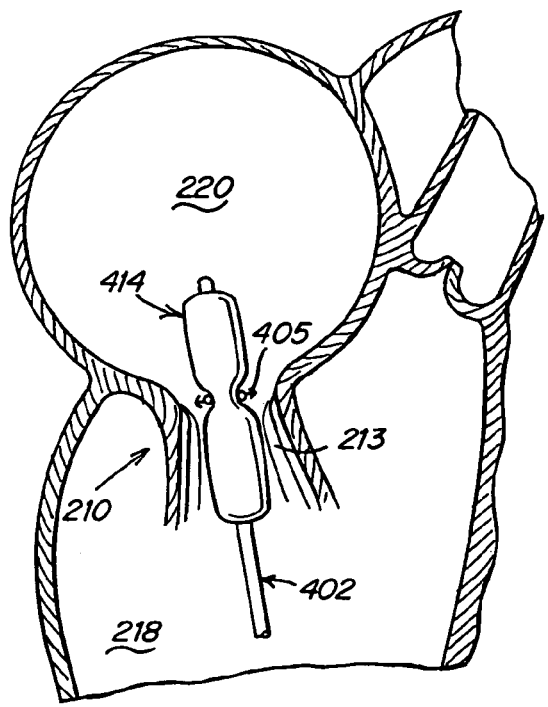
FIG. 39 schematically represents portions of the heart muscle and the positioning of the balloon relative to the mitral valve.

FIG. 38 illustrates another embodiment of a catheter. Catheter 402 supports dumbbell-shaped balloon 414. As illustrated in FIG. 39, catheter 402 can be introduced into the left ventricle 218 directed upwardly with balloon 414 disposed at mitral valve 210. The mitral valve 210 separates the left ventricle 218 from the left atrium 220. As shown in FIG. 39, associated with the mitral valve is a ring of relatively tough tissue (the annulus) just above the top of valve leaflets 213.

Figure 36:
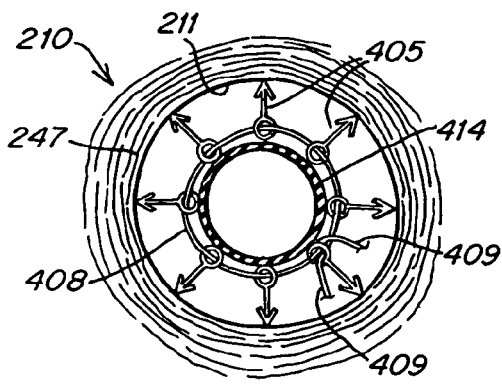
FIG. 36 schematically represents a system of the present invention for repairing a mitral valve.
Figure 36A:
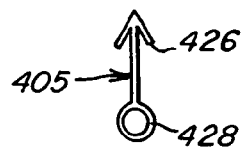
FIG. 36A shows a pin for anchoring.

FIG. 36 shows a cross-sectional view of the use of catheter 402 and balloon 414 for mitral valve repair. FIG. 36 shows the plurality of peripherally disposed anchor pins 405. FIG. 36A shows each anchor pin comprising a piercing end 426 and a loop end 428. A fiber or tether 408, as illustrated in FIGS. 36 and 37 extends through each of the loop ends 428 and has its ends at 409 free to extend through the catheter 402 to an external site where the tether can be tightened, as will be described in further detail hereinafter.

Figure 37:
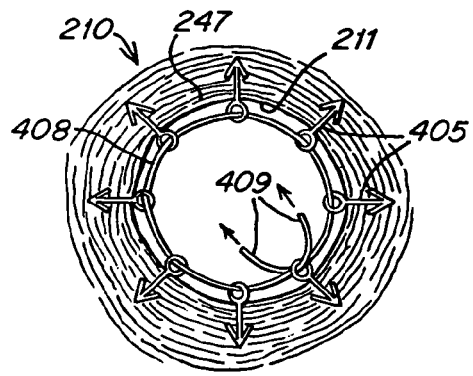
FIG. 37 illustrates the anchoring system engaged with the mitral valve.

FIG. 37 also shows the position wherein pins 405 have been inserted into wall 247, which is a section of the ring of the mitral valve just above the leaflets. Pulling tether ends 409 together can close the ring, thus pulling loop ends 428 into a smaller diameter. This smaller diameter reduces the diameter of the ring of the mitral valve so as to minimize or prevent valve regurgitation.

Initially, FIGS. 38 and 39 illustrates balloon 314 positioned at a desired location and in a deflated state. FIG. 38 illustrates pins 405 disposed about a center section of balloon 414. In the rest or deflated position as illustrated in FIG. 38, the pins disposed at their most inner diameter. This innermost diameter state is also represented in the cross-sectional view of FIG. 36. Tether 408 may extend by way of catheter 402 to an external site where it can be operated, e.g. outside the body.

Figure 40:
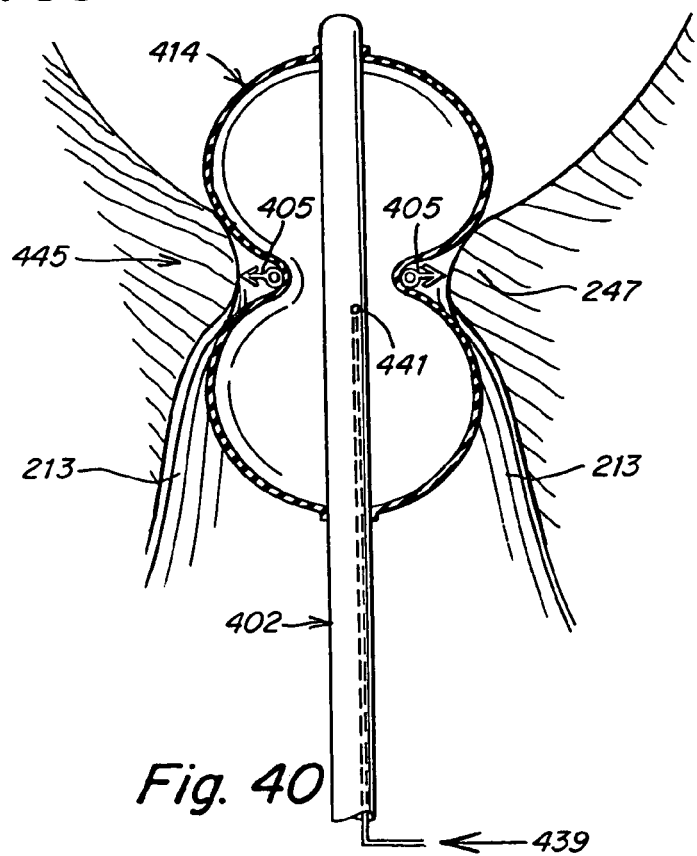
FIG. 40 illustrates the balloon in its inflated state positioned at the mitral valve.

Once the catheter and balloon are in place, such as illustrated in FIG. 39, the balloon is inflated by a balloon inflation lumen in the direction of arrow 439 in FIG. 40. Arrangements for inflating balloons are well known and are practiced, for example, in the angioplasty field. Inflation pressure may be coupled by way of the port 441 to the interior of balloon 414 causing the balloon to expand. In FIG. 40 the balloon is shown only partially expanded. When fully expanded, the anchor pins 405 extend to the ring just above the leaflets as indicted at 445 in FIG. 40. The corresponding cross-sectional view is shown in FIG. 37, depicting the anchor pins 405 penetrating and anchoring the tissue. FIG. 37 illustrates a placement of tether ends 409. As the trigone portion of the base ring of the mitral valve is the most stable portion of the ring, it is preferred that tether ends 409 leave the loop at approximately the trigone area. In this way the drawing in of the diameter of the ring is more effective.

After the anchors are seated, as illustrated in FIG. 37, tether 408 can be tightened, thereby pulling the tissue together so as to repair the mitral valve and reduce or eliminate valve regurgitation.

Several different techniques may be used for guiding the catheter 402. For example, transesophageal ultrasound or transthorasic ultrasound may be employed. Also, radiopaque dye fluoroscopy or electrophysiologic techniques may be employed for positioning of the catheter. The tether can be placed about the mitral valve and tightened by using coaxial inner and outer catheters. The concepts illustrated in FIGS. 39 and 40 may be practiced either with or without robotic control.

The aforementioned techniques for guiding the catheter may also be used for monitoring the effectiveness of the technique of the present invention. By monitoring the positioning of the balloon, one can assure that the ends of the tether are preferably at the trigone area. Also, as the tether is tightened, the surgeon may monitor the mitral valve activity to determine whether the valve base ring has closed properly so as to reduce or eliminate valve regurgitation. Tether ends may be secured by knotting the ends thereof so as to hold the tether in a closed position.

The techniques described herein may also be applied in other medical procedures involving repair of other anatomic body members. For example, the techniques described in FIGS. 17-40 may be used in closing, tightening, or constricting other anatomic conduits including, but not limited to, lumens, valves, or sphincters. One example is in connection with drawing the sphincter into a smaller diameter. This smaller diameter is particularly useful in controlling "acid reflux" by constricting an expanded sphincter that couples between the stomach and esophagus. By tightening the sphincter, stomach acids are restricted to the stomach and don't pass back toward the esophagus. Access for such a technique may be via the patient's mouth. Of course, the techniques of the invention may also be applied in virtually any other medical procedures performed internally on the patient.

The present invention provides a relatively simple system, both in the construction and in its use. The capability to decouple components at the drive unit and the receiver results in a readily portable and readily manually insertable flexible instrument system that can be handled quite effectively by the surgeon or assistant when it is to be engaged with the patient. Only a minimal number of components are positioned within the sterile field, enabling facile manipulation about the surgical site. An advantage of the system of the present invention is the decoupling nature of the system. In the system of the present invention, the instrument, drive unit and controller are inherently decoupled (attachable and detachable). The decouplable design enables the slave station to be readily portable. The instrument can be maintained as sterile but the drive unit need not be sterilized.

The instrument of the present invention is relatively small because the actuators are not housed in any articulating structure in the system of this invention. Because the actuators are remote, they may be placed under the operating table or in another convenient location and out of the sterile field. Because the drive unit is fixed and stationary, the motors may be arbitrary in size and configuration. Finally, the design allows multiple, specialized instruments to be coupled to the drive unit, allowing a user to design the instrument for particular surgical disciplines.

Having now described a limited number of embodiments of the present invention, it should now be apparent to those skilled in the art that numerous other embodiments and modifications thereof are contemplated as falling within the scope of the present invention.

The invention claimed is:

1. A medical device comprising:
   a flexible guide shaft for being disposed through a vascular lumen and having a distal end for being disposed at a predetermined location in a subject;
   a single flexible inner shaft having a proximal end and a distal end supporting at its distal end an articulating tool, the inner shaft being insertable into the guide shaft so as to dispose the tool at an operative site; and
   a drive unit coupled with the inner shaft for providing controlled actuation of tool, the drive unit being remote controllably drivable by a user via an electrical controller form a manually controllable device.

2. The device of claim 1, wherein the flexible inner shaft includes at its proximal end a mechanically drivable mechanism drivably coupled to the tool via at least a first mechanical cabling and at least a second mechanical cable intercoupling the drive unit and the mechanically drivable mechanism.

3. A medical device comprising:
   a flexible guide shaft having a distal end for being disposed at a predetermined location in a subject;
   a flexible inner shaft having a proximal end and a distal end supporting at its distal end a tool, the inner shaft being insertable into the guide shaft so as to dispose the tool at an operative site;
   a drive unit coupled with the inner shaft for providing controlled actuation of the tool, the drive unit being remote controllably drivable by a user via a manually controllable device;
   wherein the flexible inner shaft includes at its proximal end a mechanically drivable mechanism drivably coupled to the tool; and
   a mounting mechanism drivably intercoupled with the drive unit, the mechanically drivable mechanism being readily mountable on the mounting mechanism to enable drivable intercoupling from the drive unit through the mounting mechanism to the mechanically drivable mechanism.

4. The device of claim 3, wherein the drive unit is disposed at a first location remote from a second location at which the mounting mechanism is disposed, and further including at least a first tendon intercoupling the drive unit and the mounting mechanism and at least a second tendon intercoupling the mechanically drivable mechanism and the tool.

5. The device of claim 3, wherein the drive unit comprises a plurality of motors, each motor being readily drivably interconnected to and disconnected from the mechanically drivable mechanism.

6. The device of claim 5, wherein the drive unit is readily manually portable.

7. The device of claim 3, wherein the mounting mechanism is readily engageable with the disengageable from the mechanically drivable mechanism.

8. The device of claim 7, wherein the flexible shafts extend to the mechanically drivable mechanism, the flexible shafts and mechanically drivable mechanism being readily manually portable.

9. A medical device comprising:
a flexible guide having a distal end for being disposed at a predetermined location in a subject;
a flexible inner shaft having a proximal end and a distal end supporting at its distal end a tool, the inner shaft being insertable into the guide shaft so as to dispose the tool at an operative site;
a drive unit coupled with the inner shaft for providing controlled actuation of the tool, the drive unit being remote controllably drivable by a user via an electrical controller from a remote manually controllable device;
wherein the guide shaft supports an inflatable balloon, for holding the distal end of the flexible guide shaft at the predetermined location against an anatomic wall of the subject.

10. The device of claim 1, wherein the flexible inner shaft has a controlled flexible segment controlled from the drive unit for controlling a bending action thereat.

11. A medical device comprising:
flexible guide shaft having a distal end for being disposed at a predetermined location in a subject;
a flexible inner shaft having a proximal end and a distal end supporting at its distal end a tool, the inner shaft being insertable into the guide shaft so as to dispose the tool at an operative site; and
a drive unit coupled with the inner shaft for providing controlled actuation of the tool, the drive unit being remote controllably drivable by a user from an electrical controller via a manually controllable device;
wherein the flexible inner shaft has a controlled flexible segment controlled from the drive unit for controlling a bending action thereat;
wherein the flexible guide shaft has a controlled flexible segment controlled from the drive unit for controlling a bending action thereat.

12. The device of claim 11, wherein the inner shaft and the tool is constructed and arranged as a single piece disposable unit, and the controlled bending action is controlled from the manually controllable device via an electrical controller.

13. The device of claim 12, wherein the flexible guide shaft is disposable.

14. A medical device comprising:
a flexible guide shaft having a distal end for being disposed at a predetermined location in a subject;
a flexible inner shaft having a proximal end and a distal end that is connected to a tool used in performing a medical procedure, the inner shaft being insertable into the guide shaft so as to dispose the tool at an operative site; and
a drive unit coupled with the inner shaft for providing controlled movement thereof and actuation of the tool, the drive unit being remote controllably drivable by a user from an electrical controller via a manually controllable device;
wherein the drive unit also intercouples with the flexible guide shaft for controlled movement thereof;
whereby user initiated independent control of movement of both the flexible guide shaft and the flexible inner shaft is a via the drive unit from the remote manually controllable device.

15. The device of claim 14, wherein the flexible guide shaft has at least one controlled flexible segment and the drive unit controls bending at the flexible segment of the flexible guide shaft.

16. The device of claim 15, wherein the flexible inner shaft has at least one controlled flexible segment and the drive unit controls bending at the flexible segment of the flexible inner shaft, and wherein the flexible segments of both shafts are positioned about their distal ends.

17. The device of claim 14, further comprising cabling extending along the inner shaft, controlled from the drive unit, and for actuation of the tool and cabling extending between the drive unit and the proximal end of the flexible inner shaft.

18. The device of claim 1, further comprising an input device and an electrical computation system coupled to the drive unit, the computation system capable of receiving commands from the input device thereby operating the drive unit.

19. A medical device comprising:
a flexible inner shaft inserted within a flexible guide shaft, a tool being disposed at a distal end of the inner shaft for insertion into a subject;
a drive unit coupled with the inner shaft and the guide shaft separately, the drive unit capable of independently effecting movement of each shaft to at least one degree of freedom for the flexible guide shaft and at least two degrees of freedom for the flexible inner shaft; and
a user input interface including an electrical controller remote from the drive unit, for remote controllable manipulating the inner and guide shafts;
wherein at least one of said flexible inner shaft and said flexible guide shaft has a controlled flexible segment controlled from the user input interface via the drive unit for controlling a bending action thereat.

20. A medical device comprising:
a flexible guide shaft having a distal end for being disposed at a predetermined location in a subject;
a flexible disposable inner shaft having a proximal end and a distal end supporting at its distal end a tool, the inner shaft being insertable through the guide shaft so as to dispose the tool at an operative site;
a drive unit coupled with the inner shaft for providing controlled actuation of the tool and controlled deformation of one or more flexible portions of the inner shaft, the drive unit being remote controllable drivable by a user via a manually controllable device;
wherein the proximal end of the inner shaft includes a mechanically drivable mechanism drivably couplable to the drive unit, the mechanically drivable mechanism being disposable together with the tool as a unit; and
a mounting mechanism drivably intercoupled with the drive unit, the mechanically drivable mechanism being removably mountable on the mounting mechanism to enable drivable intercoupling from the drive unit through the mounting mechanism to the mechanically drivable mechanism.

21. The device of claim 20 wherein the drive unit couples with the flexible guide shaft for providing controlled deformation of one or more flexible portions of the flexible guide shaft.

22. The device of claim 20, wherein the drive unit is disposed at a first location remoter from a second location at which the mounting mechanism is disposed and the drive unit is controlled from the manually controllable device via an electrical controller.

23. The device of claim 20, wherein the drive unit comprised couples with the flexible guide shaft for providing controlled deformation of one or more flexible portions of the flexible guide shaft.

24. The device of claim 20, wherein the flexible guide shaft is inserted through a body lumen to reach the operative site.

25. The device of claim 20, wherein the drive unit is disposed in a stationary position.

26. The device of claim 20, wherein the drive unit is disposed remotely from the sterile field.

27. The device of claim 20, wherein at least said flexible guide shaft is constructed and arranged so that its physical properties mat at least some length thereof inherently and sufficiently deformable so as to enable it to readily pass atraumatically into a body lumen.

28. A remotely controllable flexible instrument system for performing a medical procedure on a subject, comprising:
a flexible instrument shaft having proximal and distal ends, carrying a tool at the distal end thereof, and insertable into the subject so as to dispose the tool at an internal target site where the medical procedure is to be performed;
a flexible guide shaft constructed and arranged so that at least some length thereof is inherently and sufficiently deformable so to readily flex and pass atraumatically through an anatomic lumen of the subject;
said flexible instrument shaft nested in a receiving passage of the flexible guide shaft and adapted to pass and be guided therethrough for positioning the tool at the internal target site;
a drive unit coupled with the flexible instrument shaft for providing controlled movement of the flexible instrument shaft with at least two degree of freedom, one of which is tool actuation and coupled with the flexible guide shaft for providing at least one degree of freedom of movement thereof; and
a user input interface controlled by a medical practitioner, remote from the drive unit, and coupled via an electrical controller which receives commands from the interface and transmit signals to the drive unit in accordance with manipulations of the medical practitioner for controlling with movement of the flexible shafts.

29. The system of claim 28 wherein said flexible instrument shaft is controlled with at least three degrees of freedom and has a controllably flexible section that is remotely controlled from said user input interface for selective bending of the flexible instrument shaft.

30. The system of claim 29 wherein said flexible guide shaft is controlled with at least two degrees of freedom and has a controllably flexible section that is remotely controlled from said user input interface for selective bending of the flexible guide shaft.

31. The system of claim 28 including a third shaft nested with the instrument and guide shafts, and remotely controllable from the user input interface.

32. The system of claim 28 wherein the drive unit comprises a plurality of control motors for controlling respective degrees of freedom of movement of the flexible instrument shaft.

33. The system of claim 32 wherein all of the plurality of motors are maintained in a stationary position even as the flexible instrument shaft is moved.

34. The system of claim 28 wherein the flexible instrument shaft is disposable.

35. The system of claim 28 further including a mechanically drivable mechanism at the proximal end of the flexible instrument shaft and drivably coupled to the tool, and a mounting mechanism drivably intercoupled with the drive unit, the mechanically drivable mechanism being removably mountable on the mounting mechanism for drivable intercoupling with the drive unit.

36. The system of claim 35 including a coupling member for enabling ready engagement with and disengagement between the mechanically drivable mechanism and the mounting mechanism.

37. A remotely controllable flexible instrument system for performing a medical procedure on a subject, comprising:
a flexible guide shaft having a distal end for being disposed at a predetermined location in the subject;
a flexible working shaft having a proximal end and a distal end, supporting at its distal end a tool, the flexible working shaft being insertable through the flexible guide shaft so as to be nested therewith and to dispose the tool at an internal operative site of the subject;
an electrically driven drive unit mechanically coupled with the flexible working shaft for providing controlled actuation of the tool; and
a user input interface controlled by a medical practitioner, remote from the drive unit, and coupled via an electrical controller which receives commands from the interface and transmits signals to the drive unit in accordance with manipulations of the medical practitioner for controlling the movement of the flexible working shaft;
said drive unit comprising one or more stationary motors mechanically, removably and drivably interconnected to the proximal end of the flexible working shaft.

38. The system of claim 37 wherein the majority of motors are maintained in a stationary position.

39. The system of claim 37 wherein at least the motor that controls the tool is maintained in a stationary position.

40. The system of claim 37 wherein two or more of said motors are maintained in a stationary position.

41. The system of claim 37 wherein said flexible working shaft has a controllably flexible section that is remotely controlled from said user input interface for selective bending of the flexible working shaft.

42. The system of claim 41 wherein said flexible guide shaft has a controllably flexible section that is remotely controlled from said user input interface for selective bending of the flexible guide shaft.

43. The system of claim 37 including a third shaft nested with the working and guide shafts, and remotely controllable from the user input interface.

44. A method of remotely controlling a flexible instrument system, comprising:
providing a flexible instrument shaft having a distal end that interconnects with a tool, the shaft further including at a proximal end thereof a mechanically drivable mechanism for controlling the tool at an operative site of a patient;

providing a flexible guide shaft having a distal end directed to said operative site;

inserting the flexible guide shaft into an anatomic vascular lumen, the flexible guide shaft adapted to conform to the configuration of the anatomic lumen;

inserting the flexible instrument shaft into and through the flexible guide shaft so as to dispose the tool at the operative site;

mechanically controlling the tool, via a drive unit and an electrical controller, and from an user input interface; and independently activating the flexible instrument shaft and the flexible guide shaft by operating the drive unit at a location remote from the shaft, so as to thereby effect positioning of the tool at the operative site.

45. The method of claim 44 wherein the flexible instrument shaft carries an articulating tool that can pivot outside of a longitudinal axis of the shaft.

46. The method of claim 44, wherein the step of inserting of the flexible guide shaft comprises providing a percutaneous access.

47. The method of claim 44, wherein said step of inserting the flexible guide shaft comprises providing access through a natural body orifice.

48. The method of claim 44, including providing at least one controlled flexible segment about the distal end of the instrument shaft capable of bending and controlled from the user input device for positioning the tool at the operative site.

49. The method of claim 48, including providing at least one controlled flexible segment about the distal end of the guide shaft capable of bending and controlled from the user input device.

50. A method of remotely controlling a flexible instrument, comprising:

providing a flexible guide shaft;

providing a flexible inner shaft having a working distal end adapted for insertion into a subject to an operative site;

inserting the flexible guide shaft into the subject;

inserting the flexible inner shaft into and through the flexible guide shaft so as to dispose the working end at the operative site;

activating movement of the flexible inner shaft with at least three degrees of freedom including activation of the working distal end;

activating the flexible guide shaft, independently from the flexible inner shaft, and with at least one degree of freedom; and controlling the activating from a user input interface remote from the shafts, for remote controllably manipulating the flexible inner and guide shafts.

51. The method of claim 50 wherein the step of activating the flexible guide shaft includes operating a tool at the working end whereby the tool can turn to a position outside of a longitudinal axis of the shaft.

52. The method of claim 50 including providing a remote controllable segment of both the flexible guide shaft and the flexible instrument shaft, and the activating step includes remote controlling the segments from the input interface via an electrical computation means.

53. A method of remotely controlling a flexible instrument, comprising:

providing a flexible guide shaft;

providing a flexible inner shaft carrying a tool that is actuable, disposed at a distal end of the flexible inner shaft and adapted for insertion into a subject to an operative site;

inserting the flexible guide shaft into the subject through a vascular lumen;

inserting the flexible inner shaft into and through the flexible guide shaft so as to dispose the tool at the operative site;

controlling operation of said tool;

activating the flexible guide shaft with at least one degree of freedom to, in turn, control disposition of said flexible inner shaft; and controlling the activating of said flexible guide shaft from a user input interface having a manually operable input device via an electrical interface for remote controllably manipulating the flexible guide shaft.

54. The method of claim 53 wherein the step of activation the flexible guide shaft includes operating a flexible segment of the flexible guide shaft.

55. The method of claim 53 including operating the flexible inner shaft via a remote controllable flexible segment thereof.

56. The method of claim 55 including operating the flexible guide shaft via a remote controllable flexible segment thereof.

57. A remotely controllable flexible instrument, comprising:

a flexible guide shaft; and a flexible inner shaft having a working distal end adapted for insertion into a subject to an operative site;

said flexible guide shaft being inserted into the subject and receiving therethough the flexible guide shaft so as to dispose the working end at the operative site;

said flexible inner shaft being controlled with at least two degrees of freedom, one of which is activation of the working distal end;

said flexible guide shaft being controlled, independently from the flexible inner shaft, and with at least one degree of freedom;

said shafts being controlled from a user input interface remote from the shaft, for remote controllably manipulating the flexible inner and guide shafts.

58. The instrument of claim 57 wherein said working distal end includes an articulating tool having a pivot for moving the tool away from a longitudinal axis of the inner shaft.

59. The instrument of claim 58 including a wrist coupled between the shaft and tool.

60. The instrument of claim 59 wherein the flexible inner shaft is controlled with at least three degrees of freedom.

61. The instrument of claim 57 wherein said working distal end comprises a medical procedure mechanism that is actuated by at least one cable.

62. The instrument of claim 57 wherein the shafts are controlled via an electrical controller.

63. A method of remotely controlling a flexible instrument, comprising:

providing a flexible guide shaft having at least one remotely controllable bendable segment disposed therealong;

providing a flexible inner shaft carrying a tool disposed at a distal end of the flexible inner shaft and adapted for insertion into a subject to an operative site;

inserting the flexible guide shaft into the subject through a vascular lumen;

inserting the flexible inner shaft into and through the flexible guide shaft so as to dispose the tool at the operative site;

activating the flexible guide shaft with at least one degree of freedom to, in turn, control disposition of said flexible inner shaft; and controlling the activating of said flexible guide shaft from a user input interface having a manually operable input device via an electrical controller for remote controllably manipulating the flexible guide shaft.

64. The method of claim 63 including controlling the activating of the flexible guide shaft by controlling the bending of a flexible segment of the flexible guide shaft.

65. The method of claim 64 including controlling an activating of the flexible inner shaft by controlling a bending of a flexible segment of the flexible inner shaft.

66. The method of claim 65 including controlling the tool and the flexible segments from the manually operable input device, and via the electrical controller.

67. A medical device for performing a medical procedure at an operative site of a patient, said medical device comprising:

a flexible guide shaft having a proximal end for being disposed outside the patient and a distal end for being disposed adjacent the operative site;

said flexible guide shaft positioned for passage through a vascular lumen to the operative site;

a flexible inner shaft having a proximal end and a distal end, said distal end supporting a tool used in performing the medical procedure;

said flexible inner shaft nested in a receiving passage of the flexible guide shaft and adapted to be received in and threaded through the flexible guide shaft for positioning the tool at the internal target site;

said flexible guide shaft having a flexible segment that is remotely controlled for controlling a bending action thereat so as to direct the location of the flexible inner shaft;

said flexible guide shaft having at its proximal end a mechanically drivable mechanism for controlling said flexible segment.

68. The medical device of claim 67 wherein said inner shaft comprises an inner instrument tube, and further having at least one cable extending through said inner instrument tube for actuating said tool.

69. The medical device of claim 67 including a mounting mechanism drivably intercoupled with a drive unit, the mechanically drivable mechanism being readily mountable on the mounting mechanism to enable drivable intercoupling from the drive unit through the mounting mechanism to the mechanically drivable mechanism.

70. The medical device of claim 69, wherein the drive unit is disposed at a first location remote from a second location at which the mounting mechanism is disposed, and further including at least a first tendon intercoupling the drive unit and the mounting mechanism and at least a second tendon intercoupling the mechanically drivable mechanism and the tool.

71. A medical device for performing a medical procedure at an operative site of a patient, said medical device comprising:

a flexible guide shaft having a proximal end for being disposed outside the patient and a distal end for being disposed adjacent the operative site;

a flexible inner shaft having a proximal end and a distal end supporting at its distal end a tool;

said flexible inner shaft nested in a receiving message passage of the flexible guide shaft and adapted to be received in and threaded through the flexible guide shaft for positioning the tool at the internal target size;

said flexible guide shaft having a flexible segment that is remotely controlled for controlling a bending action thereat so as to direct the location of the flexible inner shaft;

said flexible guide shaft having at its proximal end a mechanically drivable mechanism drivably coupled to said flexible segment;

said mechanically drivable mechanism being removably mountable on a mounting mechanism to enable drivable intercoupling from an external drive through the mounting mechanism to the mechanically drivable mechanism.

72. The medical device of claim 71 including at least one stationary motor for providing mechanical drive to the mechanically drivable mechanism.

73. The medical device of claim 71 wherein said flexible guide shaft is positioned for passage through a vascular lumen to the operative site.

74. A method of remotely controlling a flexible instrument, comprising:

providing a flexible guide shaft;

providing a flexible inner shaft carrying a tool that is cable actuated, disposed at a distal end of the flexible inner shaft and adapted for insertion into a subject to an operative site;

inserting the flexible guide shaft into the subject through a vascular lumen;

threading the flexible inner shaft into and through the flexible guide shaft so as to dispose the tool at the operative site;

activating the flexible guide shaft with at least one degree of freedom to, in turn, control disposition of said flexible inner shaft; and controlling the operation of said tool.

75. The method of claim 74 wherein the step of activating the flexible guide shaft with at least one degree of freedom includes providing a flexible segment of the flexible guide shaft that is remotely controlled for controlling a bending action thereat so as to direct the location of the flexible inner shaft.

76. The method of claim 75 wherein the activating step include activating said flexible guide shaft from a user input interface having a manually operable input device via an electrical controller for remote controllably manipulating the flexible guide shaft.

77. A remotely controllable flexible instrument system for performing a medical procedure on a subject, comprising:

a flexible instrument shaft having proximal and distal ends, and insertable into the subject so as to dispose the distal end at an internal target site where the medical procedure is to be performed;

a flexible guide shaft constructed and arranged so that at least some length thereof is inherently and sufficiently deformable so to readily flex and pass atraumatically through an anatomic vascular lumen of the subject;

said flexible instrument shaft nested in a receiving passage of the flexible guide shaft and adapted to pass and be threaded therethrough for positioning the distal end at the internal target site;

a drive unit coupled with the flexible guide shaft for providing at least one degree of freedom of movement thereof; and a user input interface controlled by a medical practitioner, remote from the drive unit, and coupled via an electrical controller which receives commands from the interface and transmits signals to the drive unit in accordance with manipulations of the medical practitioner for controlling the movement of the flexible guide shaft.

78. The system of claim 77 wherein said flexible guide shaft has a controllably flexible section that is remotely controlled from said user input interface for selective bending of the flexible instrument shaft.

79. The system of claim 77 wherein the drive unit comprises at least one stationary motor.

80. The system of claim 78 wherein the flexible guide shaft has at its proximal end a mechanically drivable mechanism for controlling said flexible section.

81. The system of claim 80 including a mounting mechanism drivably intercoupled with the drive unit, the mechanically drivable mechanism being removably mountable on the mounting mechanism to enable drivable intercoupling from the drive unit though the mounting mechanism to the mechanically drivable mechanism.

82. A method of remotely controlling a flexible instrument system, comprising:
providing a flexible instrument shaft having a working distal end;
providing a flexible guide shaft having a distal end directed to said operative site, the flexible guide shaft further including at a proximal end thereof a mechanically drivable mechanism for controlling the position of the flexible guide shaft;
inserting the flexible guide shaft into an anatomic lumen;
threading the flexible instrument shaft into and through the flexible guide shaft so as to dispose the working end at the operative site;
mechanically controlling the working end; and
activating a controllable flexible section of the flexible guide shaft by operating a stationary drive unit form a user interface input device that is remote from the shaft via an electrical controller, so as to thereby effect positioning of the flexible instrument shaft.

83. A medical device of performing a medical procedure at an internal operative site of a patient, said medical device comprising:
a flexible guide shaft having a proximal end for being disposed outside the patient and a distal end for being disposed adjacent the operative site;
said flexible guide shaft positioned for passage through an anatomic lumen to the operative site;
a flexible inner shaft having a proximal end and a working distal end used in performing the medical procedure;
said flexible inner shaft nested in a receiving passage of the flexible guide shaft and adapted to be received in and threaded through the flexible guide shaft for positioning the working distal end at the operative site;
said flexible guide shaft having a flexible segment that is remotely controlled for controlling a bending action thereat so as to direct the location of the flexible inner shaft;
said flexible guide shaft having at its proximal end a mechanically drivable mechanism for controlling said flexible segment;
said mechanically drivable mechanism comprising at least one rotatable body from which a tendon controls said flexible segment.

84. The medical device of claim 83 including an electromechanical drive unit coupled with the inner shaft being remote controllably drivable by a user via an electrical controller from a manually controllable user input device.

85. The medical device of claim 84 including at least one interlocking rotatable element engageable with said rotatable body for transferring mechanical motion from the drive unit to the flexible guide shaft.

86. The medical device of claim 85 including a plurality of rotatable bodies and corresponding rotatable elements for controlling multiple degrees of freedom.

* * * * *